(12) United States Patent
Ochiai

(10) Patent No.: US 9,163,291 B2
(45) Date of Patent: Oct. 20, 2015

(54) GLYCEROL 3-PHOSPHATE ACYLTRANSFERASE HOMOLOGUE AND USE THEREOF

(75) Inventor: Misa Ochiai, Osaka (JP)

(73) Assignee: SUNTORY HOLDINGS LIMITED, Osaka (JP)

( * ) Notice: Subject to any disclaimer, the term of this patent is extended or adjusted under 35 U.S.C. 154(b) by 279 days.

(21) Appl. No.: 13/575,700

(22) PCT Filed: Feb. 3, 2011

(86) PCT No.: PCT/JP2011/052258
§ 371 (c)(1),
(2), (4) Date: Jul. 27, 2012

(87) PCT Pub. No.: WO2011/096481
PCT Pub. Date: Aug. 11, 2011

(65) Prior Publication Data
US 2012/0302777 A1 Nov. 29, 2012

(30) Foreign Application Priority Data

Feb. 3, 2010 (JP) ................................. 2010-022125

(51) Int. Cl.
| C11B 1/10 | (2006.01) |
| A23L 1/30 | (2006.01) |
| C12N 9/10 | (2006.01) |
| A23D 9/00 | (2006.01) |
| C12P 7/64 | (2006.01) |

(52) U.S. Cl.
CPC ........... *C12Y 203/01015* (2013.01); *A23D 9/00* (2013.01); *A23L 1/30* (2013.01); *A23L 1/3008* (2013.01); *C11B 1/10* (2013.01); *C12N 9/1029* (2013.01); *C12P 7/6463* (2013.01); *C12P 7/6472* (2013.01)

(58) Field of Classification Search
None
See application file for complete search history.

(56) References Cited

U.S. PATENT DOCUMENTS

| 7,855,321 | B2 | 12/2010 | Renz et al. |
| 8,110,388 | B2 | 2/2012 | Ochiai et al. |
| 8,247,209 | B2 | 8/2012 | Ochiai et al. |
| 2006/0094091 | A1* | 5/2006 | Macool et al. ................. 435/134 |
| 2006/0094092 | A1 | 5/2006 | Damude et al. |
| 2006/0110806 | A1 | 5/2006 | Damude et al. |
| 2006/0115881 | A1 | 6/2006 | Damude et al. |
| 2006/0174376 | A1 | 8/2006 | Renz et al. |
| 2009/0311380 | A1 | 12/2009 | Damude et al. |
| 2010/0022647 | A1 | 1/2010 | Damude et al. |
| 2010/0159110 | A1 | 6/2010 | Ochiai et al. |
| 2010/0323085 | A1 | 12/2010 | Ochiai |
| 2011/0023185 | A1 | 1/2011 | Renz et al. |
| 2011/0086919 | A1 | 4/2011 | Damude et al. |
| 2012/0115231 | A1 | 5/2012 | Ochiai |
| 2012/0277451 | A1 | 11/2012 | Ochiai |
| 2013/0123361 | A1 | 5/2013 | Damude et al. |

FOREIGN PATENT DOCUMENTS

| EP | 2 479 271 | 7/2012 |
| WO | 2004/087902 | 10/2004 |
| WO | 2006/052824 | 5/2006 |
| WO | 2008/156026 | 12/2008 |

OTHER PUBLICATIONS

Extended European Search Report issued with respect to European App. No. 11739829.7, dated Jun. 28, 2013.
U.S. Appl. No. 13/496,081 to Misa Ochiai, filed Mar. 14, 2012.
International Search Report for PCT/JP2011/052258, mailed Apr. 26, 2011.
Calder, "n-3 Fatty Acids, Inflammation, and Immunity—Relevance to Postsurgical and Critically Ill Patients" *Lipids*, vol. 39, No. 12, pp. 1147-1161 (2004).
Dircks et al., "Mammalian Mitochondrial Glycerol-3-Phosphate Acyltransferase" *Biochimica et Biophysica Acta*, vol. 1348, pp. 17-26 (1997).
Murata et al., "Glycerol-3-Phosphate Acyltransferase in Plants" *Biochimica et Biophysica Acta*, vol. 1348, pp. 10-16 (1997).
Zheng et al., "The Initial Step of the Glycerolipid Pathway" *The Journal of Biological Chemistry*, vol. 276, No. 45, pp. 41710-41716 (2001).
Mishra et al., "Purification and Characterization of Thiol-Reagent-Sensitive Glycerol-3-Phosphate Acyltransferase from the Membrane Fraction of an Oleaginous Fungus" *Biochem. J.*, vol. 355, pp. 315-322 (2001).
Chatrattanakunchai et al., "Oil Biosynthesis in Microsomal Membrane Preparations from *Mortierella alpina*" *Biochemical Society Transactions*, vol. 28, No. 6, pp. 707-709 (2000).

* cited by examiner

*Primary Examiner* — Michele K Joike
*Assistant Examiner* — Mindy G Brown
(74) *Attorney, Agent, or Firm* — Greenblum & Bernstein, P.L.C.

(57) ABSTRACT

The present invention provides a novel glycerol 3-phosphateacyltransferase gene and use thereof. The object of the present invention can be solved by providing a nucleic acid having a nucleotide sequence set forth in SEQ ID NO: 1, 4, or 8, SEQ ID NO: 3, 6, or 11, or SEQ ID NO: 7 or 12 and a mutant thereof. The present invention also provides a protein having an amino acid sequence set forth in SEQ ID NO: 2, 5, or 9 and a mutant thereof.

8 Claims, 13 Drawing Sheets

Figure 1-1

```
            1                                                                                                  100
genome      GTTGACATAGTCTTTTTGGTAGCAGTAGCATTGTTGTAGTTTCTCTTACTCAACGGACAGCAGCAGCACGACCGCCGAGGTAAAGCGGTGGATCCCATAG
CDS         ----------------------------------------------------------------------------------------------------

101                                                                                                200
genome      AGACTCTTTTGCCCTCGTCTCCACTGTCGCTCTCCCCACAGAAAAACATTTTTATTTCCTTTCCCGCATTTTTTTCTTCTTTTTTTCCTGCCTCTCTTGT
CDS         ----------------------------------------------------------------------------------------------------

201                                                                                                300
genome      CTCTCCTCCCCTAAGCACCACCTAACCCGCTCTATCGCCCAACCACTTCAACTCAGCACCCTCACGGAGCCTGCCAACCAACGTTGCAAGAAGGAAAAAA
CDS         ----------------------------------------------------------------------------------------------------

301                                                                                                400
genome      AGTACAGCGCATCTTGTAGTCCAGCGCGGAGCAGTGGAAAAAACCTCTCCATTCCGACCTAACAGATCACGCAGTCTGATCAGCTAGTTTGCCCCACAGTT
CDS         ----------------------------------------------------------------------------------------------------

401                                                                                                500
genome      ATTGCATCACCCTTTCAACCAGTCCACATGACAACCGGCGACAGTACCGCTGCTGACGGTAGCAGCAGCAGTAGCAGCAACAACAGCACCAACATTGCCA
CDS         ----------------------------------------------------------------------------------------------------

501                                                                                                600
genome      GTACTAGTAACGGCAAGGCTGCTCCCCACCCACTCCAAGGGGGATCACCCGCTCCTGTAGCTCCAGTTTTGGAATTGAAGCCTCTCAAGAATGTTATGCC
CDS                                                                                                      ATGCC 601                                                                                                700
genome      CATCGTTCCAGCTCAGCAAGTCGACTCCTCCTCGTGCCCTCCCTCTGGTGAATCTAGCCCGTTGATTCCCAGTTTGGGCGAAGGAGTGCATTCGGGTCAT
CDS         CATCGTTCCAGCTCAGCAAGTCGACTCCTCCTCGTGCCCTCCCTCTGGTGAATCTAGCCCGTTGATTCCCAGTTTGGGCGAAGGAGTGCATTCGGGTCAT 701                                                                                                800
genome      GGACACGTTGTCGACAATGACGAGTCCGGCGTGGAGAACATTACGCAAGTTCAAATTGAATATTCCAGCGGCTATGAACGAGTTTGGATGCTTGTTTAGT
CDS         GGACACGTTGTCGACAATGACGAGTCCGGCGTGGAGAACATTAC--------------------------------------------------------

801                                                                                                900
genome      TTTGTATTAACACGAACTTTCGCTCTTGTTATTGTTGTTATCAATGCAGCAAAAAGCACGCAGGACGAATTAGAGAAGATCCGGTCGGCTTCGTGGTGCA
CDS                                                         CAAAAAGCACGCAGGACGAATTAGAGAAGATCCGGTCGGCTTCGTGGTGCA 901                                                                                                1000
genome      GACTGCAGCTTTCTATCAGGGCACGGTACGTTCAATATCTGACATCACTGCTTTAGTGGAGCCGCAGAGGAAAGCACTTCTTAACGACAACTGCAGCTGG
CDS         GACTGCAGCTTTCTATCAGGGCAC----------------------------------------------------------------------------

1001                                                                                               1100
genome      ATCGGTCGGTACCTCCTGCTCAACGAGCTATCAGCCCTTCTCCGCCGCCATTGTGAGGGTGATTTGTCTCATACCAGGAACAGCAGAAGAAAAAGAGGAA
CDS         ----------------------------------------------------------------------------------------------------

1101                                                                                               1200
genome      TCGTGTTCACAAAGCATCGCTTCGGGGTTGCGCTCACGCTCGGTCCTCTTGATTGCTCCCTGGAAGTCTCCCTTCTGCAAACTGTCACTCTCCCACGTTC
CDS         ----------------------------------------------------------------------------------------------------

1201                                                                                               1300
genome      CCTTTTTTTTTTTTTTTACTATCCTCCCATCCCCTGCCTCTCGTCATGCTTGAGCTGAATAATGCTAAATTCTTATCCGCATATCGTCTTTGCTTTTT
CDS         ----------------------------------------------------------------------------------------------------

1301                                                                                               1400
genome      AGGGTTGGAGAAGCTACAGCAACTATGTTGGAACGCGCCATTCTTTACGAAGGCTTCTCTGCAACCTTCAAGGAGCCGAATTCTCGCCAGTTCAAAAGGTAA
CDS         -GGGTTGGAGAAGCTACAGCAACTATGTTGGAACGCGCCATTCTTTACGAAGGCTTCTCTGCAACCTTCAAGGAGCCGAATTCTCGCCAGTTCAAAAG---

1401                                                                                               1500
genome      CACAAGATAGGGTGCTGTCTGTACTTCAACACGATTCGTCAAAATGGCATGATCTAACGAACCCTACCTTGACCTCCTAGTGAATGATCTCATCAAGGAC
CDS                                                                                               TGAATGATCTCATCAAGGAC
```

Figure 1-2

```
          1501                                                                        1600
genome    ATGGCCAACAAGCAGTTGGATGTCCTGATCAAGCAAAGACAAGATGCGTATGACGCAGAGAGGACTGCAAATGCAGGAAAAAGAACTTCAAGCCCAAAG
CDS       ATGGCCAACAAGCAGTTGGATGTCCTGATCAAGCAAAGACAAGATGCGTATGACGCAGAGAGGACTGCAAATGCAGGAAAAAGAACTTCAAGCCCAAAG 1601                                                                        1700
genome    TTCGACTCCTTCGCCCAGAAGATATCGAGGCTCGTCGCAAAACATTAGAAGCCGAGCTTGTTGCCGGTGGCAAAGTCAAATATGGACAAACTTGTTTGTGA
CDS       TTCGACTCCTTCGCCCAGAAGATATCGAGGCTCGTCGCAAAACATTAGAAGCCGAGCTTGTTGCCGGTGGCAAAGTCAAATATGGACAAACTTGTTTGTGA 1701                                                                        1800
genome    TATGAACAGTATCAAATTCATCAGGTATGGACCAACACGAGAATAACGCAGCGTGGAACTGAACAGTGTGGCAGAAGAGGGATGGCGAGATATATTTGTT
CDS       TATGAACAGTATCAAATTCATCAGGT---------------------------------------------------------------------

1801                                                                        1900
genome    GTTTGCTAGACACCAGATGTTAACAACTTTCCTCCTTGGCTGATGTGTTAGGTTCTTCGGCTTCCTCATCAACAAGATCGTTGTGAGAATGTACCATCAA
CDS       ----------------------------------------------------TCTTCGGCTTCCTCATCAACAAGATCGTTGTGAGAATGTACCATCAA 1901                                                                        2000
genome    GGAATTCAGATCAAGCAGTCCGAGTTCTTGGAGCTGCGGAGGATAGCTGAGTACTGCGCAGAGAAAAAGTATTCGATGGTGGTGTTGCCATGCCACAAGT
CDS       GGAATTCAGATCAAGCAGTCCGAGTTCTTGGAGCTGCGGAGGATAGCTGAGTACTGCGCAGAGAAAAAGTATTCGATGGTGGTGTTGCCATGCCACAAGT 2001                                                                        2100
genome    CACACATCGACTACCTCGTCGTCTCGTACATTTTCTTCCCGCATGGGATTAGCTTTACCTCACATTGCTGCTGGCGATAACCTGGACATCCCCATTGTCGG
CDS       CACACATCGACTACCTCGTCGTCTCGTACATTTTCTTCCCGCATGGGATTAGCTTTACCTCACATTGCTGCTGGCGATAACCTGGACATCCCCATTGTCGG 2101                                                                        2200
genome    AAAGGCACTCAAAGGCAGCAGGCGCGTTCTTCATTGGCCGTTCTTGGGCTGACGATCAACTTTACACCAGCATTGTTCAGGAATATGTTCAGCAGCTTTTG
CDS       AAAGGCACTCAAAGGCAGCAGGCGCGTTCTTCATTGGCCGTTCTTGGGCTGACGATCAACTTTACACCAGCATTGTTCAGGAATATGTTCAGCAGCTTTTG 2201                                                                        2300
genome    GAGCGAGGATACAATATCGAGTGCTTCATCGAGGGCACCCGAAGCAGAACAGGAAAACTTTTGCCACCAAAGCTGGGAGGTTCGTTCACAGCTTTGGTCT
CDS       GAGCGAGGATACAATATCGAGTGCTTCATCGAGGGCACCCGAAGCAGAACAGGAAAACTTTTGCCACCAAAGCTGGGAG------------------

2301                                                                        2400
genome    TGTTTTTGCTACTGGGCACGCTGGCGATCTCTTTGGGTATTAACCTTCACACCAATCCACCTTTACTAGTCCTAAAGATTATCATGGATGCTATCCTTTC
CDS       ----------------------------------------------------------------------TCCTAAAGATTATCATGGATGCTATCCTTTC 2401                                                                        2500
genome    GAACCGGCATCCAAGACTGCTACATCGTGCCCATCTCTATCGGTTATGACAAGGTCATCGAAACCGAGACTTATATCAATGAGCTTCTCGGAATCCCCAAG
CDS       GAACCGGCATCCAAGACTGCTACATCGTGCCCATCTCTATCGGTTATGACAAGGTCATCGAAACCGAGACTTATATCAATGAGCTTCTCGGAATCCCCAAG 2501                                                                        2600
genome    GAAAAGGAGAGTTTGTCGGGTGTTATTACGAATTCGAGGCTGCTCGAGCTCAACATGGGCCGCATTGATGTCGGATTTGCAAAGCCGTACAGTTTGCGAA
CDS       GAAAAGGAGAGTTTGTCGGGTGTTATTACGAATTCGAGGCTGCTCGAGCTCAACATGGGCCGCATTGATGTCGGATTTGCAAAGCCGTACAGTTTGCGAA 2601                                                                        2700
genome    ACTTTATGAATCATGAGATCGAGCGCAGAGAGTAAGCAGAACCTGTGTTTTGTTGTGCAAGACGTTTTCAAAACTGGAGAGGAATTATGTTGACCCAGGG
CDS       ACTTTATGAATCATGAGATCGAGCGCAGAGAG-------------------------------------------------------------------

2701                                                                        2800
genome    CTATTTGTTTTTCTGCATTTAGGATCATCAATAAGCGGGAAGACACCGATAGTCTGGCGAAATCTCAGCTGCTAAAGGCATTGGGCTACAAGGTCTTGGC
CDS       -----------------------ATCATCAATAAGCGGGAAGACACCGATAGTCTGGCGAAATCTCAGCTGCTAAAGGCATTGGGCTACAAGGTCTTGGC 2801                                                                        2900
genome    AGACATCAACTCGGTCTCTGTAGTAATGCCGACGGCCCTCGTGGGTACTGTCATCGTTACACTCCGAGGACGAGGTGTTGGCCGTAATCAGCTGATCCGT
CDS       AGACATCAACTCGGTCTCTGTAGTAATGCCGACGGCCCTCGTGGGTACTGTCATCGTTACACTCCGAGGACGAGGTGTTGGCCGTAATCAGCTGATCCGT
```

Figure 1-3

```
         2901                                                                           3000
genome   CGTGTTGAGTGGCTGAAGCGCGAGATTCTTTCCAAGGGTGGTCGCGTTGCCAACTTTAGCGGGATGGAAACTGGCGAGCTTGTAGATCGAGCATTGGGCG
CDS      CGTGTTGAGTGGCTGAAGCGCGAGATTCTTTCCAAGGGTGGTCGCGTTGCCAACTTTAGCGGGATGGAAACTGGCGAGCTTGTAGATCGAGCATTGGGCG 3001                                                                           3100
genome   TTCTTAAGGACCTTGTGGCGCTGCAGAAGAATTTGCTCGAGCCCGTCTTCTATGCGGTCAAGCGCTTCGAGCTTTCGTTCTACAGGAATCAGCTCATCCA
CDS      TTCTTAAGGACCTTGTGGCGCTGCAGAAGAATTTGCTCGAGCCCGTCTTCTATGCGGTCAAGCGCTTCGAGCTTTCGTTCTACAGGAATCAGCTCATCCA 3101                                                                           3200
genome   CCTCTTTGTCCATGAGGCCATCATCGCCCTGACGATGTACAGCCGGCATCAAGATTGGTGGCGCCAAGTCTACACAACACATTAGTCAGAATGAGCTGCTG
CDS      CCTCTTTGTCCATGAGGCCATCATCGCCCTGACGATGTACAGCCGGCATCAAGATTGGTGGCGCCAAGTCTACACAACACATTAGTCAGAATGAGCTGCTG 3201                                                                           3300
genome   AAGGAGGTCACCTTCCTGAGCCGCCTGCTCAAGACCGACTTTATCTACAACCCTGGCGATATTGAGAGTAACTTGGAGCATACATTGGATTACCTCAAGG
CDS      AAGGAGGTCACCTTCCTGAGCCGCCTGCTCAAGACCGACTTTATCTACAACCCTGGCGATATTGAGAGTAACTTGGAGCATACATTGGATTACCTCAAG- 3301                                                                           3400
genome   TGAGTTATCTCGCACAGGAATAAGGGACAGCTGCAATTCGCTGAAAGTAGACCTGAGCGCAACGGTCTAACATTATCGTTCTTTTCTAGAAATCCAATGT
CDS      ------------------------------------------------------------------------------------AAATCCAATGT 3401                                                                           3500
genome   GATCGAGCTTGACAGTGAAGGATATGTCGGACTCTCTGATGCTGAACGCAGCAAGGGCCCGAGAGAACTATGGTAATGGGCTATTCTATTTGTACTCACTA
CDS      GATCGAGCTTGACAGTGAAGGATATGTCGGACTCTCTGATGCTGAACGCAGCAAGGGCCCGAGAGAACTATG------------------------

3501                                                                           3600
genome   CAGACGTGATGTGCATGTTGTATCGGCCGAGAAAGTCGTTTCTGACTGAACCTCTCATTTTATCATTACTCTAGACTTTTATTGTTTCCTGCTCTGGCCC
CDS      ---------------------------------------------------------------------ACTTTTATTGTTTCCTGCTCTGGCCC 3601                                                                           3700
genome   TTCCTGGAGACATACTGGCTCGCAGCCGTGTCCCTGTATACCCTGATTCCCACCGCCAAAGAGTTGACTCAGCAGTTGCACAGCAACGGAGAGCCTCAGG
CDS      TTCCTGGAGACATACTGGCTCGCAGCCGTGTCCCTGTATACCCTGATTCCCACCGCCAAAGAGTTGACTCAGCAGTTGCACAGCAACGGAGAGCCTCAGG 3701                                                                           3800
genome   TTCACTGGGTTGAGGAGCGCGTGTTCATGGAGAAGACGCAAATGTTCGGAAAGACGCTTTACTACCAGGGAGACCTCTCCTACTTTGAGTCTGTCAACAT
CDS      TTCACTGGGTTGAGGAGCGCGTGTTCATGGAGAAGACGCAAATGTTCGGAAAGACGCTTTACTACCAGGGAGACCTCTCCTACTTTGAGTCTGTCAACAT 3801                                                                           3900
genome   GGAGACGCTCAAGAATGGTTTTAATCGTCTGTGCGATTATGGCATCCTTATGATGAAGGGACCCACCAATGCCAAGGACAAGACAAAGGTTGCTCTCCAC
CDS      GGAGACGCTCAAGAATGGTTTTAATCGTCTGTGCGATTATGGCATCCTTATGATGAAGGGACCCACCAATGCCAAGGACAAGACAAAGGTTGCTCTCCAC 3901                                                                           4000
genome   CCTGATTTTATGCCAAGCCGAGGTGCTGACGGTCATGTCATTGGCAGCGGCCACTTTGGGATATGGTGGAACATATCCGCACGTTCAGACGTGAAGGCA
CDS      CCTGATTTTATGCCAAGCCGAGGTGCTGACGGTCATGTCATTGGCAGCGGCCACTTTGGGATATGGTGGAACATATCCGCACGTTCAGACGTGAAGGCA 4001                                                                           4100
genome   AGAATCGTCGTGATAACGCCCACAGGTAAGGAACATGTGTCTTGACATTGCTCGAAACGAAATTTGTTGCTCTGTATGCTTTGTCACCAGGGGTACTAATG
CDS      AGAATCGTCGTGATAACGCCCACAG---------------------------------------------------------------------

4101                                                                           4200
genome   GCTTGTGCTCTTGCTTACACTTTCCAACCTAGTTTCCTCCCGTGTCCTGCGGTTTGCAGAGGTCGTCGCGAACGCTCCAGCTCGGTTAAGGTACCCTTG
CDS      ----------------------------------TTTCCTCCCGTGTCCTGCGGTTTGCAGAGGTCGTCGCGAACGCTCCAGCTCGGTTAAGGTACCCTTG 4201                     4248
genome   CCCAATCCGGCACCCAAAAGGACAGGCGATGGCGCCCCGAAATTATAA
CDS      CCCAATCCGGCACCCAAAAGGACAGGCGATGGCGCCCCGAAATTATAA
```

Figure 2-1

```
   1  ATGGCCAACAAGCAGTTGGATGTCCTGATCAAGCAAAGACAAGATGCGTATGACGCAGAGAGGACTGCAAATGCAGGAAAAAAGAACTTCAAGCCCAAAG
       M  A  N  K  Q  L  D  V  L  I  K  Q  R  Q  D  A  Y  D  A  E  R  T  A  N  A  G  K  K  N  F  K  P  K  V·

101  TTCGACTCCTTCGCCCAGAAGATATCGAGGCTCGTCGCAAAACATTAGAAGCCGAGCTTGTTGCGGTGGCAAAGTCAAATATCGACAAACTTGTTTGTGA
       ·  R  L  L  R  P  E  D  I  E  A  R  R  K  T  L  E  A  E  L  V  A  V  A  K  S  N  I  D  K  L  V  C  D·

201  TATGAACAGTATGAAATTCATCAGGTTCTTCGCCTTCCTCATCAACAACATCCTTGTGAGAATGTACCATCAAGGAATTCACATCAAGGAGTCCGAGTTC
       ·  M  N  S  M  K  F  I  R  F  F  A  F  L  I  N  N  I  L  V  R  M  Y  H  Q  G  I  H  I  K  E  S  E  F

301  TTGGAGCTGCGGAGGATAGCTGAGTACTGCGCAGAGAAAAAGTATTCGATGGTGGTGTTGCCATGCCACAAGTCACACATCGACTACCTCGTCGTCTCGT
       L  E  L  R  R  I  A  E  Y  C  A  E  K  K  Y  S  M  V  V  L  P  C  H  K  S  H  I  D  Y  L  V  V  S  Y·

401  ACATTTTCTTCCGCATGGGATTAGCTTTACCTCACATTGCTGCTGGCGATAACCTGGACATGCCCATTGTCGGAAAGGCACTCAAAGGAGCAGGCGCGTT
       ·  I  F  F  R  M  G  L  A  L  P  H  I  A  A  G  D  N  L  D  M  P  I  V  G  K  A  L  K  G  A  G  A  F·

501  CTTCATTCGCCGTTCTTGGGCTGACGATCAACTTTACACCAGCATTGTTCAGGAATATGTTCAGGAGCTTTTGGAGGGAGGATACAATATCGAGTGCTTC
       ·  F  I  R  R  S  W  A  D  D  Q  L  Y  T  S  I  V  Q  E  Y  V  Q  E  L  L  E  G  G  Y  N  I  E  C  F

601  ATCGAGGGCACCCGAAGCAGAACAGGAAAAACTTTTGCCACCAAAGCTGGGAGTCCTAAAGATTATCATGGATGCTATGCTTTCGAACCGCATCCAAGACT
       I  E  G  T  R  S  R  T  G  K  L  L  P  P  K  L  G  V  L  K  I  I  M  D  A  M  L  S  N  R  I  Q  D  C·

701  GCTACATCGTGCCCATCTCTATCGGTTATGACAAGGTCATCGAAACCGAGACTTATATCAATGAGCTTCTCGGAATCCCCAAGGAAAAGGAGAGTTTGTG
       ·  Y  I  V  P  I  S  I  G  Y  D  K  V  I  E  T  E  T  Y  I  N  E  L  L  G  I  P  K  E  K  E  S  L  W·

801  GGGTGTTATTACGAATTCGAGGCTGCTCCAGCTCAAGATGGGCCGCATTGATGTCCGATTTGCAAAGCCGTACAGTTTGCGAAACTTTATGAATCATGAG
       ·  G  V  I  T  N  S  R  L  L  Q  L  K  M  G  R  I  D  V  R  F  A  K  P  Y  S  L  R  N  F  M  N  H  E

901  ATCGAGCGCAGAGAGATCATCAATAAGCGGGAAGACACCGATAGTGTGGCGAAATCTCAGCTGCTAAAGGCATTGGGCTACAAGGTCTTGGCAGACATCA
       I  E  R  R  E  I  I  N  K  R  E  D  T  D  S  V  A  K  S  Q  L  L  K  A  L  G  Y  K  V  L  A  D  I  N·

1001  ACTCGGTCTCTGTAGTAATGCCCACGGCCCTCGTGGGTACTGTCATCCTTACACTCCGAGGACGAGGTGTTGGCCGTAATGAGCTGATCCGTCGTGTTGA
       ·  S  V  S  V  V  M  P  T  A  L  V  G  T  V  I  L  T  L  R  G  R  G  V  G  R  N  E  L  I  R  R  V  E·

1101  GTGGCTGAAGCGCGAGATTCTTTCCAAGGGTGGTCGCGTTGCCAACTTTAGCGGGATGGAAACTGGCGAGGTTGTAGATCGAGCATTGGGCGTTCTTAAG
       ·  W  L  K  R  E  I  L  S  K  G  G  R  V  A  N  F  S  G  M  E  T  G  E  V  V  D  R  A  L  G  V  L  K

1201  GACCTTGTGGCGCTGCAGAAGAATTTGCTCGAGCCCGTCTTCTATGCGGTCAAGCGCTTCGAGCTTTCGTTCTACAGGAATCAGCTCATCCACCTCTTTG
       D  L  V  A  L  Q  K  N  L  L  E  P  V  F  Y  A  V  K  R  F  E  L  S  F  Y  R  N  Q  L  I  H  L  F  V·

1301  TCCATGAGGCCATCATCGCCGTGACGATGTACACCCGCATCAAGATTGGTGGCGCCAAGTCTACACAACACATTAGTCAGAATGAGCTGCTGAACGAGGT
       ·  H  E  A  I  I  A  V  T  M  Y  T  R  I  K  I  G  G  A  K  S  T  Q  H  I  S  Q  N  E  L  L  N  E  V·
```

Figure 2-2

```
1401    CACCTTCCTGAGCCGCCTGCTCAAGACCGACTTTATCTACAACCCTGGCGATATTGAGAGTAACTTGGAGCATACATTGGATTACCTCAAGAAATCCAAT
         T  F  L  S  R  L  L  K  T  D  F  I  Y  N  P  G  D  I  E  S  N  L  E  H  T  L  D  Y  L  K  K  S  N

1501    GTGATCGAGGTTGACAGTGAAGGATATGTCGGACTCTCTGATGCTGAACGCAGCAAGGGCCGAGAGAACTATGACTTTTATTGTTTCCTGCTCTGGCCCT
         V  I  E  V  D  S  E  G  Y  V  G  L  S  D  A  E  R  S  K  G  R  E  N  Y  D  F  Y  C  F  L  L  W  P  F·

1601    TCGTGGAGACATACTGGCTCGCAGCCGTGTCCCTGTATACCCTGATTCCCACCGCCAAAGAGTTGACTCAGCAGTTGGACAGCAACGGAGAGCCTCAGGT
          V  E  T  Y  W  L  A  A  V  S  L  Y  T  L  I  P  T  A  K  E  L  T  Q  Q  L  D  S  N  G  E  P  Q  V

1701    TCACTGGGTTGAGGAGCGCGTGTTCATGGAGAAGACGCAAATGTTCGGAAAGACGCTTTACTACCAGGGAGACCTCTCCTACTTTGAGTCTGTCAACATG
         H  W  V  E  E  R  V  F  M  E  K  T  Q  M  F  G  K  T  L  Y  Y  Q  G  D  L  S  Y  F  E  S  V  N  M

1801    GAGACGCTCAAGAATGGTTTTAATCGTCTGTGCGATTATGGCATCCTTATGATGAAGCGACCCACCAATGCCAAGGAGAAGACAAAGGTTGCTCTCCACC
         E  T  L  K  N  G  F  N  R  L  C  D  Y  G  I  L  M  M  K  R  P  T  N  A  K  E  K  T  K  V  A  L  H  P

1901    CTGATTTTATGCCAAGCCGAGGTGCTGACGGTCATGTCATTGCCAGCGGCGCACTTTGGGATATGGTCGAACATATCGGCACGTTCAGACGTGAAGGCAA
          D  F  M  P  S  R  G  A  D  G  H  V  I  A  S  G  A  L  W  D  M  V  E  H  I  G  T  F  R  R  E  G  K

2001    GAATCGTCGTGATAACGCCACAGTTTCCTCCCGTGTCCTGCGGTTTGCAGAGGTCGTCGCGAACGCTCCAGCTCCGGTTAAGGTACCCTTGCCCAATCCG
         N  R  R  D  N  A  T  V  S  S  R  V  L  R  F  A  E  V  V  A  N  A  P  A  P  V  K  V  P  L  P  N  P

2101    GCACCCAAAAGGACAGGCGATGGCGCCCCGAAATTATAA
         A  P  K  R  T  G  D  G  A  P  K  L
```

Figure 3-1

```
        1                                                                                                100
genome  ATGGAAGGAGACGCAGTACGGCCTGCTTTGCCCAGAAAGATCCCTGGTCTCTACAGCTTCATCAAACTCCTTTGCAGGACGCCTTTTTCACATCTTCTTCA
CDS     ATGGAAGGAGACGCAGTACGGCCTGCTTTGCCCAGAAAGATCCCTGGTCTCTACAGCTTCATCAAACTCCTTTGCAGGACGCCTTTTTCACATCTTCTTCA 101                                                                                              200
genome  GGGATTACGAGGCCTTTCATACCCAGTTTGTTCCACAGGACGAACCATTGCTAGTTATCTCCAACCATGGCAACTACCTTCTGGATGGCCTCGCCTTGTT
CDS     GGGATTACGAGGCCTTTCATACCCAGTTTGTTCCACAGGACGAACCATTGCTAGTTATCTCCAACCATGGCAACTACCTTCTGGATGGCCTCGCCTTGTT 201                                                                                              300
genome  GGCCACCTTTCCAGGCCAGATCTCCTTTTTCATGGCACAGCCCAATTTCAAGACTCCAATTGGTGGCATCGCCAGGAAGATTCGTGCCATTCCAGTACTG
CDS     GGCCACCTTTCCAGGCCAGATCTCCTTTTTCATGGCACAGCCCAATTTCAAGACTCCAATTGGTGGCATCGCCAGGAAGATTCGTGCCATTCCAGTACTG 301                                                                                              400
genome  AGGCAAGTCTTTGAAAAACCACAAAATACAGAGCGAAATAGTGACCATAGGCTCGACATATGGGGTGGCGTGATCTGCGCATCCTGTCTTTTCGTCAACC
CDS     AG------------------------------------------------------------------------------------------------

401                                                                                              500
genome  CTTTTTGCTTTGCCCACTTGCTGACCCTGTGATTATGCTCTTTGTCCAATCTATAGACCACAGGACGCGGCCAGATATGACGCTGCGAGTATGGTCACAA
CDS     ------------------------------------------------------ACCACAGGACGCGGCCAGATATGACGCTGCGAGTATGGTCACAA 501                                                                                              600
genome  TCGCTCACGATGGCAACTCAGTGCTCGGTCAGGGGATTGGCAAGCAGCTGACTTTCGGCGATACTGTCTATATCGAGTCTGGGACGTTCCAGGACGCTGG
CDS     TCGCTCACGATGGCAACTCAGTGCTCGGTCAGGGGATTGGCAAGCAGCTGACTTTCGGCGATACTGTCTATATCGAGTCTGGGACGTTCCAGGACGCTGG 601                                                                                              700
genome  CAGGGACAATGGCGTCACGCAATGTTATGGCGTGGTCAGTGCGATCGTCAGTGACAACGAGGTGTTGTTCAAGGCTCCCGGTTTGAAATGGATTCCCGCA
CDS     CAGGGACAATGGCGTCACGCAATGTTATGGCGTGGTCAGTGCGATCGTCAGTGACAACGAGGTGTTGTTCAAGGCTCCCGGTTTGAAATGGATTCCCGCA 701                                                                                              800
genome  TCCTTCACATCGGAACGCGACATTGCCTATATCAAATCGGGAAAGATTGTTCGGCATGGGTCACTGAAGATCAGAGTGGAACCTGGCAACACCTGGGTCG
CDS     TCCTTCACATCGGAACGCGACATTGCCTATATCAAATCGGGAAAGATTGTTCGGCATGGGTCACTGAAGATCAGAGTGGAACCTGGCAACACCTGGGTCG 801                                                                                              900
genome  GAATCAATGAGGCGCTTAAAGCACAGGAGCAGCAGAACAATGGCTCGTTGGCAAGCAGCGCAACGGGACGATCGGCAAGTTTGTTCACAAGATATTTTC
CDS     GAATCAATGAGGCGCTTAAAGCACAGGAGCAGCAGAACAATGGCTCGTTGGCAAGCAGCGCAACGGGACGATCGGCAAGTTTGTTCACAAGATATTTTC 901                                                                                              1000
genome  AAAGTCGCCGGATGCAGACGCAAGATCAGATGATGTGCATTTGGCCGAGAATGGGTATTCCGGAGCAGATATCCCCGGGTCCTTGACCGCTCCAGCCAAC
CDS     AAAGTCGCCGGATGCAGACGCAAGATCAGATGATGTGCATTTGGCCGAGAATGGGTATTCCGGAGCAGATATCCCCGGGTCCTTGACCGCTCCAGCCAAC 1001                                                                                             1100
genome  TTCACACAACTGAGACTACAGCACTACTCAAAAAGGCGCGGCTCGTGAAACAGCTCCAGTCATCCTATATACACAGTACCAAAGCGCGCAGACTGGAACG
CDS     TTCACACAACTGAGACTACAGCACTACTCAAAAAGGCGCGGCTCGTGAAACAGCTCCAGTCATCCTATATACACAGTACCAAAGCGCGCAGACTGGAACG 1101                                                                                             1200
genome  CGAGGCTTTCATCATACTCTACCACTGACAGGACAAATGCAGTGGCCGATGCGACAACGACGACGAGACCACGCGCCGTGCAAATGGACTTAGGAACGC
CDS     CGAGGCTTTCATCATACTCTACCACTGACAGGACAAATGCAGTGGCCGATGCGACAACGACGACGAGACCACGCGCCGTGCAAATGGACTTAGGAACGC 1201                                                                                             1300
genome  GCAAGCCGGACACAACCCCGCTGGAACCAATGGCGTTGTCAATGGAGGCGCATCCACATCCATGAGCCCACGAAGCACTCCATTGACCTCCCCTACACTT
CDS     GCAAGCCGGACACAACCCCGCTGGAACCAATGGCGTTGTCAATGGAGGCGCATCCACATCCATGAGCCCACGAAGCACTCCATTGACCTCCCCTACACTT 1301                                                                                             1400
genome  CACAGCTCCACATCGGCCGTGTCACACTTCCCCTCGCGACCCTGCCGCTTCCAGTTCTCACACCCAATCGACCATTCTGTGATCTACGAGAGCGTCTGGA
CDS     CACAGCTCCACATCGGCCGTGTCACACTTCCCCTCGCGACCCTGCCGCTTCCAGTTCTCACACCCAATCGACCATTCTGTGATCTACGAGAGCGTCTGGA 1401                                                                                             1500
genome  AGAACTTTGAGGATGGTCGCACCGTTGCTGTATTCCCTGAAGGCGTATCGAGCGACGATTATCACTTGCTCGACTTCAAATATGGCTGCACCATCATGGT
CDS     AGAACTTTGAGGATGGTCGCACCGTTGCTGTATTCCCTGAAGGCGTATCGAGCGACGATTATCACTTGCTCGACTTCAAATATGGCTGCACCATCATGGT
```

Figure 3-2

```
              1501                                                                                    1600
   genome  TCTTGGATACCTGGCTCAGCATCGCTCTAAGACTCTAAGGATTATACCATGCGGACTGAACTTCTTTAATCGCCATCGATTTCGATCCCGGTTCTACGCC
      CDS  TCTTGGATACCTGGCTCAGCATCGCTCTAAGACTCTAAGGATTATACCATGCGGACTGAACTTCTTTAATCGCCATCGATTTCGATCCCGGTTCTACGCC 1601                                                                                    1700
   genome  GACTACTCCGATCCGCTCACCGTCCCCGACCACCTTGTAGAGATGTATCGCGAAGGAGGAGAAGCCAAGAAGCAAGGTAAGGAAGACCAAAACTGCCTCC
      CDS  GACTACTCCGATCCGCTCACCGTCCCCGACCACCTTGTAGAGATGTATCGCGAAGGAGGAGAAGCCAAGAAGCAAG---------------------

1701                                                                                    1800
   genome  CTCACATATCGCAGTCTGTCGAAGTTTTTCTCACATATCTCTTTTTCTCTTAGCCTGTACTGAGCTTCTGCAGATGATTCACTCGGCTGTGGAGGGGCTG
      CDS  -----------------------------------------------------CCTGTACTGAGCTTCTGCAGATGATTCACTCGGCTGTGGAGGGGCTG 1801                                                                                    1900
   genome  ACTCTTAACGCACCAAAACTACGACGAGCTGCGACTTTACAAGGCAACGCGACGACTCTACAGCACTGGGAAGAAGCTTACGGTGCCACAGAAATTGGAGC
      CDS  ACTCTTAACGCACCAAAACTACGACGAGCTGCGACTTTACAAGGCAACGCGACGACTCTACAGCACTGGGAAGAAGCTTACGGTGCCACAGAAATTGGAGC 1901                                                                                    2000
   genome  TAACTCGCCGTTTTGCGAAAGGTTATCAAAATCTGGTCATGACGCCGAGCATGGCTGCATTGAAACGCGACATTGATGCTTATGACAAGCATCTCTCCAG
      CDS  TAACTCGCCGTTTTGCGAAAGGTTATCAAAATCTGGTCATGACGCCGAGCATGGCTGCATTGAAACGCGACATTGATGCTTATGACAAGCATCTCTCCAG 2001                                                                                    2100
   genome  CAGCGGCGTCCGAGACGCACAACTGACCGCAAACCCAAGCATTCTGGCTGCCCTTGTATTCATATTGCCGGCGTTATTCCTCTTGCCAGTGCTGTTCCTG
      CDS  CAGCGGCGTCCGAGACGCACAACTGACCGCAAACCCAAGCATTCTGGCTGCCCTTGTATTCATATTGCCGGCGTTATTCCTCTTGCCAGTGCTGTTCCTG 2101                                                                                    2200
   genome  CTTTCGTTAGCCGGGACCTTGCTCTTCGGACCTGTTGGACTTTTGGCCGTCCTGGGCGGCAAAGCAGAAAGGACACGCAGGCCATGCTTGCCTTTCAGTCTT
      CDS  CTTTCGTTAGCCGGGACCTTGCTCTTCGGACCTGTTGGACTTTTGGCCGTCCTGGGCGGCAAAGCAGAAAGGACACGCAGGCCATGCTTGCCTTTCAGTCTT 2201                                                                                    2300
   genome  ATCTCCCAGTTTCACGTTGGCCTGGCCCGAGATGTGATCGCCACCTGGAAGATCGTGGTGTCCTTGGCGGTTGATGCCCGTCTGCTTTATTCTGGACGCAAC
      CDS  ATCTCCCAGTTTCACGTTGGCCTGGCCCGAGATGTGATCGCCACCTGGAAGATCGTGGTGTCCTTGGCGGTTGATGCCCGTCTGCTTTATTCTGGACGCAAC 2301                                                                                    2400
   genome  ACTGCTCACGATCCTAGCACACCATTGGGAAGCACTGCAGGAGTACTGGACTATGGGTCGTCTAGTTGCGTTCTGGCTGCTGTCAACATTTGTGATTTTT
      CDS  ACTGCTCACGATCCTAGCACACCATTGGGAAGCACTGCAGGAGTACTGGACTATGGGTCGTCTAGTTGCGTTCTGGCTGCTGTCAACATTTGTGATTTTT 2401                                                                                    2500
   genome  CCAACGATGGCGTATGGTACGGTCTGGCTTTGGGAGTGGCAGATTGATTTGAAGATGCAGATCTATGTATGGTCGTGGAAGCTCTGCCGGAGGCAATGCAG
      CDS  CCAACGATGGCGTATGGTACGGTCTGGCTTTGGGAGTGGCAGATTGATTTGAAGATGCAGATCTATGTATGGTCGTGGAAGCTCTGCCGGAGGCAATGCAG 2501                                                                                2598
   genome  AGATGAAGCGCTGGAGACAGGATCTTCTCGAGAGAATGGATGCACTTGTCCAAACGATGGGCCGGTAGAAGGGTCTTTGATGTATCGGGCTATTATTGA
      CDS  AGATGAAGCGCTGGAGACAGGATCTTCTCGAGAGAATGGATGCACTTGTCCAAACGATGGGCCGGTAGAAGGGTCTTTGATGTATCGGGCTATTATTGA
```

Figure 4-1

```
   1   GTTTGTCTCTCGACCTTTCGTCATCACTCTCTCGTCGTCATCCCAGCCAGCCTTTTGCTTCTTTTTCATTTCTTTGCCGCATGGACTAACGGCTGACACT

101   CTCACGCCCTCTCCTCCATCGCAAAGTATTTCTTGCACTGCTTGCCCTGTTTTTAATCGACTCCTCGTCAAGCAATCACCTCCAGCGGATCCCAGGTGGC

201   CGCAGCCCTATACCCCAACTGCCAATGGAAGGAGACGCAGTACGGCCTGCTTTGGCCAGAAAGATCCCTGGTCTCTACAGCTTCATCAAACTCCTTTGCA
                                     M  E  G  D  A  V  R  P  A  L  A  R  K  I  P  G  L  Y  S  F  I  K  L  L  C  R ·

301   GGACGCTTTTTCACATCTTCTTCAGGGATTACGACGCCTTTCATACCCAGTTTGTTCCACAGGACGAACCATTGCTAGTTATCTCCAACCATGGCAACTA
       · T  L  F  H  I  F  F  R  D  Y  D  A  F  H  T  Q  F  V  P  Q  D  E  P  L  L  V  I  S  N  H  G  N  Y ·

401   CCTTCTGGATGGCCTCGCCTTGTTGGCCACCTTTCCAGGCCAGATCTCCTTTTTGATGGCACAGCCCAATTTCAAGACTGCAATTGGTGGCATCGCCAGG
       · L  L  D  G  L  A  L  L  A  T  F  P  G  Q  I  S  F  L  M  A  Q  P  N  F  K  T  A  I  G  G  I  A  R

501   AAGATTGGTGCCATTCCAGTACTGAGACCACAGGACGCGGCCAGATATGACGGTGCCAGTATGGTCACAATCGCTCAGGATGGCAACTCAGTCCTCGGTC
         K  I  G  A  I  P  V  L  R  P  Q  D  A  A  R  Y  D  G  A  S  M  V  T  I  A  Q  D  G  N  S  V  L  G  Q ·

601   AGGGGATTGGCAAGCAGCTGACTTTGGGCGATACTGTCTATATCGAGTGTGGGACGTTCCAGGACGCTGGCAGGGACAATCGCGTCACGCAATGTTATGG
       · G  I  G  K  Q  L  T  L  G  D  T  V  Y  I  E  C  G  T  F  Q  D  A  G  R  D  N  R  V  T  Q  C  Y  G ·

701   CGTGGTCAGTGCGATCGTCAGTGACAACGAGGTGTTGTTCAAGGCTCCCGGTTTGAAATGGATTCCCGCATCCTTGACATCGGAACGCGACATTGCCTAT
       · V  V  S  A  I  V  S  D  N  E  V  L  F  K  A  P  G  L  K  W  I  P  A  S  L  T  S  E  R  D  I  A  Y

801   ATCAAATCGCGAAAGATTGTTCGGCATGGGTCACTCAAGATCAGAGTGGAACGTGGCAACACCTGGGTCGGAATCAATGAGGCGCTTAAAGCACAGGAGC
         I  K  S  R  K  I  V  R  H  G  S  L  K  I  R  V  E  R  G  N  T  W  V  G  I  N  E  A  L  K  A  Q  E  Q ·

901   AGCAGAACAATGGCTCGTTGGCAAGCAGCGCAACGGGGACGATCGGCAAGTTTGTTCACAAGATATTTTCAAAGTCGCCGGATGCAGACGCAAGATCAGA
       · Q  N  N  G  S  L  A  S  S  A  T  G  T  I  G  K  F  V  H  K  I  F  S  K  S  P  D  A  D  A  R  S  D ·

1001   TGATGTGCATTTGGCCGAGAATGGGTATTCCGGAGCAGATATCCCCGGGTCCTTGACCGCTCCAGCCAACTTTCACACAACTGAGACTACACCACTACTC
       · D  V  H  L  A  E  N  G  Y  S  G  A  D  I  P  G  S  L  T  A  P  A  N  F  H  T  T  E  T  T  P  L  L

1101   AAAAAGGCGCGCTCGTCAAACAGCTCCAGTCATCCTATATACACAGTACCAAAGCGCGCAGACTCGAACGCGAGGCTTTCATCATACTCTACCACTCACA
         K  K  A  R  S  S  N  S  S  S  H  P  I  Y  T  V  P  K  R  A  D  S  N  A  R  L  S  S  Y  S  T  T  H  S ·

1201   GCACAAATGCAGTGGCCGATGCCGACAACGACGACGAGACCACGCGCCCTGCAAATGGACTTAGGAACGCGCAAGGCGGACACAACCCCGCTGGAACCAA
       · T  N  A  V  A  D  A  D  N  D  D  E  T  T  R  P  A  N  G  L  R  N  A  Q  G  G  H  N  P  A  G  T  N ·

1301   TGGCGTTGTCAATGGAGGCGCATCCACATCCATGAGCCCACGAAGCACTCCATTGACCTCCCCTACACTTCACAGCTCCACATCGGCCGTGTCACACTTC
       · G  V  V  N  G  G  A  S  T  S  M  S  P  R  S  T  P  L  T  S  P  T  L  H  S  S  T  S  A  V  S  H  F

1401   CCCTCGCGACCCTGCCCCTTCCAGTTCTCACACCCAATCGACCATTCTGTGATCTACGAGAGCGTCTGGAAGAACTTTGAGGATGGTCGCACCGTTGCTG
         P  S  R  P  C  P  F  Q  F  S  H  P  I  D  H  S  V  I  Y  E  S  V  W  K  N  F  E  D  G  R  T  V  A  V ·

1501   TATTCCCTGAAGGCGTATCGAGCGACGATTATCACTTGCTCGACTTCAAATATGGCTGCACCATCATGGTTCTTGGATACCTGGCTCAGCATCGCTCTAA
       · F  P  E  G  V  S  S  D  D  Y  H  L  L  D  F  K  Y  G  C  T  I  M  V  L  G  Y  L  A  Q  H  R  S  K ·

1601   GACTCTAAGGATTATACCATGCGGACTGAACTTCTTTAATCGCCATCGATTTCGATCCCGGTTCTACGCCGACTACTCCCATCCGCTCACCGTCCCCGAC
       · T  L  R  I  I  P  C  G  L  N  F  F  N  R  H  R  F  R  S  R  F  Y  A  D  Y  S  H  P  L  T  V  P  D

1701   CACCTTGTAGAGATGTATCGCGAAGGAGGAGAAGCCAAGAAGCAAGCCTGTACTGAGCTTCTGCAGATGATTCACTCGGCTGTGGAGGGGCTGACTCTTA
         H  L  V  E  M  Y  R  E  G  G  E  A  K  K  Q  A  C  T  E  L  L  Q  M  I  H  S  A  V  E  G  L  T  L  N ·

1801   ACGCACCCAAACTACGACGAGCTGCGACTTTACAAGGCAACGCGACGACTCTACAGCACTGGGAAGAAGCTTACCGTGCCACAGAAATTGGAGCTAACTCG
       · A  P  N  Y  D  E  L  R  L  Y  K  A  T  R  R  L  Y  S  T  G  K  K  L  T  V  P  Q  K  L  E  L  T  R ·

1901   CCGTTTTGCGAAAGGTTATCAAAATCTGGTCATGACGCCGAGCATGGCTGCATTGAAACGCGACATTGATGCTTATGACAAGCATCTCTCCAGCAGCGGC
       · R  F  A  K  G  Y  Q  N  L  V  M  T  P  S  M  A  A  L  K  R  D  I  D  A  Y  D  K  H  L  S  S  S  G
```

Figure 4-2

```
2001    GTCCGAGACGCACAACTGACCGCAAACCCAAGCATTCTGGCTGCCCTTGTATTCATATTGCCCGCGTTATTCCTCTTGCCAGTGCTGTTCCTGCTTTCGT
         V  R  D  A  Q  L  T  A  N  P  S  I  L  A  A  L  V  F  I  L  P  A  L  F  L  L  P  V  L  F  L  L  S  L ·

2101    TACCCGGGACGTTGCTCTTCGGACCTGTTGGACTTTTGGCGTCGTGGGCGGCAAAGCAGAAAGGACAGCAGGCCATGCTTGCCTTTCAGTCTTATCTCCC
         ·  P  G  T  L  L  F  G  P  V  G  L  L  A  S  W  A  A  K  Q  K  G  Q  Q  A  M  L  A  F  Q  S  Y  L  P ·

2201    AGTTTCACGTTGGCCTGGCCGAGATGTGATCGCCACCTGGAAGATCGTGGTGTCCTTGGCGTTGATGCCCGTCTGCTTTATTCTGGACGCAACACTGCTC
         ·  V  S  R  W  P  G  R  D  V  I  A  T  W  K  I  V  V  S  L  A  L  M  P  V  C  F  I  L  D  A  T  L  L

2301    ACGATCCTAGCACACCATTGGGAAGCACTGCAGGAGTACTGGACTATGGGTCGTCTAGTTGCGTTCTGGCTGCTGTCAACATTTGTGATTTTTCCAACGA
         T  I  L  A  H  H  W  E  A  L  Q  E  Y  W  T  M  G  R  L  V  A  F  W  L  L  S  T  F  V  I  F  P  T  M ·

2401    TGGCGTATGGTACGGTCTGGCTTTGGGAGTGGCAGATTGATTTGAAGATGCAGATCTATGTATGGTGGTGGAAGCTCTGCGGAGGCAATGCAGAGATGAA
         ·  A  Y  G  T  V  W  L  W  E  W  Q  I  D  L  K  M  Q  I  Y  V  W  W  W  K  L  C  G  G  N  A  E  M  K ·

2501    GCGCTGGAGACAGGATCTTGTCGAGAGAATGGATGCACTTGTCGAAAGGATGGGCGGTAGAAGGGTGTTTGATGTATCGGGCTATTATTGAGCAACGTTC
         ·  R  W  R  Q  D  L  V  E  R  M  D  A  L  V  E  R  M  G  G  R  R  V  F  D  V  S  G  Y  Y

2601    ATGTATAAAGTCATTTGGCCCAATTCTTCTCCAAAAAAAAAAAAAAAAAAAAAAAAAAAAAAAAAA
```

```
             1                                                                                                    100
MaGPAT5     MEGDAVRPALARKIPGLYSFIKLLCRTLFHIFFRDYDAFHTQFVPQDEPLLVISNHGNYLLDGLALLATFPGQISFLMAQPNFKTAIGGIARKIGAIPVL
UMO3369     MTGTSNLPAASSQDSAVITTLSSPSEAHLSTASHPSAAASSTASAQHPPTIDTHPTRLSSNDPLKKHPNTAIAKGTAAEVGSKQKEFQRRAQHLSLTSKP
ScSCT1      ----------------------------------------------------------------------------------------------------
ScGPT2      ----------------------------------------------------------------------------------------------------

101                                                                                                  200
MaGPAT5     RPQDAARYDGASMVTIAQDGNSVLGQGIGKQLTLGDTVYIECGTFQDAGRDNRVTQCYGVVSAIVSDNEVLFKAPGLKWIPASLTSERDIAYIKSRKIVR
UMO3369     IPYARQGDSPRLLVVLKDFDRLLR--------------SLPIPLHHIVPTIVARFICRVFRSQNIMASNIAFDIALFFWRIIINLFFREIRPRSSWRIPR
ScSCT1      --------MPAPKLTEKFASSKSTQK-----------TTNYSSIEAKSVKTSADQAYIYQEP-SATKKILYSIATWLLYNIFHCFFREIRGRGSFKVPQ
ScGPT2      ------MSAPAADHNAAKP-------------------IPHVPQASRRYKNSYNGFVYN-----IHTWLYDVSVFLFNILFTIFFREIKVRGAYNVPE 201                                                                                                  300
MaGPAT5     HGSLKIRVERGNTWVGINEALKAQEQQNNGSLASSATGTIGKFVHKIFSKSPDADARSDDVHLAENGYSGAGIPGSLTAPANFHTIETTPLLKKARS-SN
UMO3369     EG-PVIFVAAPHHNQFLDPLLLAS-------EVRRASGRRVAFLIAEKSIKRRFVGAAARIMQSIPVARAABSAKAGKGYISLHPSGDPLLIQGHG----
ScSCT1      QG-PVIFVAAPHANQFVDPVILMG-------EVKKSVNRRVSFLIAESSLKQPPIGFLASFFMAIGVVRPQDNLKPAEGTIRVDPTDYKRVIGHD----
ScGPT2      VAVPTIELVCAPHANQFIDPALVMSQTRLLKTSAGKSRSRMPCFVTAESSFKKRFISFFGHAMGGIPVPRIQDNLKPVDENLEIYAPDLKNHPEIIKGRSK 301                                                                                                  400
MaGPAT5     SSSHPIYTVPKRADSNARLSSYSTTHSTNAVADADNDDETTRPANGLRNAQGGHNPAGTNGVVNGGASTSMSPRSTPLTSPTLHSSTSAVSHFPSRPCPF
UMO3369     -------TAFKSQLQLKGQIMLPKACGHATVEVVEVISDTELKIKKEFKDPRALDMLRGKVPQPEPTKSDKKPSK----SSSSKALEKVAADLFENQGCRY
ScSCT1      ---------THFLTDCMPKGLIGLPKSMGFG-EIQSIESDTSLTLRKEFKMA---------------------------KPEIKTALLTGTTY
ScGPT2      NPQTTPVNFTKRFSAKSLLGLPDYLSNA--QIKEIPDDETIILSSPFRTS--------------------------KSKVVELLTNGTNF 401                                                                                                  500
MaGPAT5     QFSHPIBHSVIYESFWKNFEDGRTVAVFPEGVSSDDYHLLDFKYSCTIMVLGYLAQHRSKTLRIIPCGLNFENRHRFRSRFYADYSHPLTYPDHLVEMYR
UMO3369     SCLPFVBQTQMYAKYYDKLAEGGCLGIFPEGGSHDRTDLLPLKAGVVIMALGAMSANRDLNVRIVFVGLSYFHPHKFRSRAVVEFGAPIDVPRQLVGQFD
ScSCT1      KYAAKVBQSCVYHRVFEHLAHNNCIGIFPEGGSHDRTNLLPLKAGVAIMALGCMDKHPDVNVKIVPCGMNYFHPHKFRSRAVVEFGDPIEIPKELVAKYH
ScGPT2      KYAEKIBNTETFQSVFDHLHTKGCVGIFPEGGSHDRPSLLPIKAGVAIMALGAVAADPTMKVAVVFCGLHYFHRNKFRSRAVLEYGEPIVVDGKYGEMYK
                                  * +                                *
             501                                                                                                  600
MaGPAT5     EGGEAKKQACTELLQMIHSAVEGLILNAPNYDELRLYKATRRLYST--GKKETVPQKLELTRRFAKGYQNLVMTPSMAALKRDIDAYDKHESSSGVRBAQ
UMO3369     EGGEGKRKAVGQMMDIVYDGLKGVILRAPDYETLMVVQAGRRLYRA-PGQSLSLGQTVALNRKFIMGYLQFKDEPRVVKLRDEVLRYNKKLRYAGLRDHQ
ScSCT1      NPETN-RDAVKELLDTISKGLQSVFVTCSDYETLMVVQTIRRLYMTQFSTKLPLPLIVEMNRRMVKGYEFYRNDPKIADLTKDIMAYNAALRHYNLPDHL
ScGPT2      DSP----RETVSKLLKKITNSLFSVIENAPDYDTLMVIQAARRLYQP-VKVRLPLPAIVEINRRLLFGYSKFKDDPRIIHLKKLVYDYNRKLDSVGLKDHQ 601                                                                                                  700
MaGPAT5     LTANPSILAALVF----ILPALFLLPVLFLISLPGTLLFGPVGLLASWAAKQKGQQAMLAFQSYLPVSRWPGRDVIATMKIVVSLALMPVCFILDATELT
UMO3369     VERATRAGWRSLG---LLAYRLGLLGLWGGLALPGAVLNSPIIILAKIISHKKAKEALAASQ----VKVAGRDVLATMKVLVSLGVAPILYSFYAALAT
ScSCT1      VEEAKVNFAKNLG---LVFFRSIGLCILFSLAMPGIIMFSPVFILAKRISQEKARTALSKST----VKIKANDVIATMKILIGMGFAPLLYIFWSVEIT
ScGPT2      VMQLKTTKLEALRCFVTLIVRLIKFSVFAILSLPGSILFTPIFIICRVYSEKKAKEGLKKSL----VKIKGTDLLATMKLIVAELIILAPILYVTYSILI 701                                                                                                  800
MaGPAT5     ILAHHWEALQEYWTMGRLVAFWLLSTFVIFPTMAYGTVWLWEWQIDLKMQIYVWWWKLCGGN----AEMKRWHQDLVERMDALVERMGGRRVFBVSGYY-
UMO3369     YLAHRLELSPRTRALMP------LY-TLIVLPTMSYSALKFAEVGIDIYKSLPPLFISLIPGNHKVILDLQQTHTKISADMHALIDELAPQVWEBFAENRM
ScSCT1      YYLRHKPWNKIYVFSG---------SYISCVIVTYSALIVGDIGMDGFKSLRPLVLSLTSP--KGLQKLQKDRRNLAERIIEVVNNFGSELFPBFDSAAL
ScGPT2      ILARKQHYCRIWVPSNNAFIQFVY-FYALLVFTTISSLKTGEIGVDLFKSLRPLFVSIVYPG--KKIEEIQTTRKNLSLELTAVCNDLGPLVFPBYDKLAT 801                                                                                                  900
MaGPAT5     ----------------------------------------------------------------------------------------------------
UMO3369     LPSASAPPTPSREALVWKDKKQSSSAASDALSHPLQWMDERLFGWGRRRHSSTRRSLTAEEIKHLRSPSLTRGSAKDENSVLDDEDGARFEGEGDGSLDD
ScSCT1      REEFDVIDE----------EEEDRKTSELN--------------RRKMLRKQKIKRQEKDSSSPIISQRDNHDAYEHHNQDSDGVSLVNSDNSLSN
ScGPT2      EIFSKRDGY----------DVSSDAESSIS-----------RMSVQSRS------RSSS---------IHSIGSLASNALSRVNSRGSLTD 901                                                                                                 1000
MaGPAT5     ----------------------------------------------------------------------------------------------------
UMO3369     VSEGSSSFIESGEEDEGDYEAVFSMLNPQNLLNGLRNGGLSPGTPGSGGRRSRTHSRSRSGSRGSIGGVASGETFAEKRNRSSQDLRALMREGGAMSPTT
ScSCT1      IPLFSSTFH--------------------------------------RKSESSLASTSVAPSSSSEFEVENEILE--------
ScGPT2      IPIFSDAKQ----------------------------------------GQWKS---------EGETSEDEDEFDE--------
```

GLYCEROL 3-PHOSPHATE ACYLTRANSFERASE HOMOLOGUE AND USE THEREOF

TECHNICAL FIELD

The present invention relates to a novel acyltransferase gene and use thereof. The acyltransferase gene of the present invention may be a glycerol 3-phosphate acyltransferase (GPAT) gene and/or a glycerone phosphate O-acyltransferase (GNPAT) gene.

BACKGROUND ART

Fatty acids are important components constituting lipids such as phospholipid and triacylglycerol. Fatty acids having two or more unsaturated bond sites are collectively called polyunsaturated fatty acids (PUFAs). Specifically, for example, arachidonic acid, dihomo-γ-linolenic acid, eicosapentaenoic acid, and docosahexaenoic acid are known, and various bioactivities thereof have been reported (Non-Patent Literature 1). Some of the polyunsaturated fatty acids cannot be synthesized in animal bodies, and such polyunsaturated fatty acids should be ingested from foods as essential fatty acids.

In animal bodies, the polyunsaturated fatty acids are contained in various organs and tissues. For example, arachidonic acid is isolated from lipids extracted from suprarenal gland and liver of animals. The amounts of these polyunsaturated fatty acids contained in animal organs are, however, small, and the polyunsaturated fatty acids extracted and isolated from animal organs only are insufficient for a large amount of supply thereof. Thus, microbial techniques have been developed for obtaining polyunsaturated fatty acids by culturing various microorganisms. In particular, microorganisms in the genera *Mortierella* are known to efficiently produce lipids containing polyunsaturated fatty acids such as arachidonic acid. Other attempts have also been made to produce polyunsaturated fatty acids in plants. Polyunsaturated fatty acids are known to constitute reserve lipids such as triacylglycerol and accumulate within microorganism cells or plant seeds.

Triacylglycerol as a reserve lipid is generated in living bodies as follows: An acyl group is transferred to glycerol 3-phosphate by glycerol 3-phosphate acyltransferase to generate lysophosphatidic acid. Another acyl group is transferred to the lysophosphatidic acid by lysophosphatidic acid acyltransferase to generate phosphatidic acid. The phosphatidic acid is dephosphorylated by phosphatidic acid phosphatase to generate diacylglycerol. A further acyl group is transferred to the diacylglycerol by diacylglycerol acyltransferase to ultimately generate triacylglycerol.

It is known that in the triacylglycerol biosynthetic pathway or the phospholipid biosynthetic pathway mentioned above, glycerol 3-phosphate acyltransferase (hereinafter, also referred to as "GPAT": EC 2.3.1.15) involves a reaction generating lysophosphatidic acid through acylation of glycerol 3-phosphate.

Existence of a GPAT gene has been reported in some organisms. As GPAT genes derived from mammals, two types of GPAT genes, i.e., a microsomal type (membrane-bound form) and a mitochondrial type (membrane-bound form), have been cloned (Non-Patent Literature 2). As GPAT genes derived from plants, three types of GPAT genes, i.e., a microsomal type (membrane-bound form), a mitochondrial type (membrane-bound form), and a chloroplast type (free form), have been cloned (Non-Patent Literature 3).

As GPAT genes derived from fungi, *Saccharomyces cerevisiae*, two types of GPAT genes, i.e., microsomal type (membrane-bound form) GPT2/GAT1 (YKR067w) and SCT1/GAT2 (YBL011w), have been cloned, and it is known that simultaneous deletion of these types of GPAT genes results in death (Non-Patent Literature 4). It has been shown that GPT2 has an activity showing broad substrate specificity to fatty acids from palmitic acid (16:0) to oleic acid (18:1), whereas SCT1 shows high substrate selectivity to fatty acids having 16 carbon atoms such as palmitic acid (16:0) and palmitoleic acid (16:1) (Non-Patent Literature 4).

In addition, the GPAT gene has been cloned from various biological species. In particular, GPAT derived from a lipid-producing fungus, the genera *Mortierella*, is reported as follows.

Regarding GPAT derived from *Mortierella ramanniana*, a microsomal type GPAT has been isolated, and it has been shown that this GPAT preferentially uses oleic acid (18:1) as an acyl donor with a selectivity as 5.4 times high as that to palmitic acid (16:0) (Non-Patent Literature 5). Regarding GPAT derived from *Mortierella alpina* (hereinafter, also referred to as "*M. alpina*"), it has been reported that a glycerol 3-phosphate acyltransferase activity resides in a microsomal fraction (Non-Patent Literature 6).

It has been shown that, when GPAT (membrane-bound form) present in microsome of *M. alpina* is reacted with various acyl-CoAs in vitro, the GPAT uses a broad range of polyunsaturated fatty acids, such as oleic acid (18:1), linoleic acid (18:2), dihomo-γ-linolenic acid (DGLA) (20:3), and arachidonic acid (20:4), as substrates, with maitaining its high activity (Patent Literature 1).

It has been shown that GPAT cloned from *M. alpina* (ATCC No. 16266) (hereinafter, referred to as MaGPAT1 (ATCC No. 16266)) was expressed in *Yarrowia lipolytica* that had been transformed such that eicosapentaenoic acid (EPA) can be biosynthesized, and as a result, a proportion of dihomo-γ-linolenic acid (DGLA) (20:3) increased, whereas a proportion of oleic acid (18:1) decreased, among the total fatty acids. This demonstrated that a polyunsaturated fatty acid having a longer chain and a higher degree of unsaturation was selectively incorporated (Patent Literature 2).

In recent studies, a GPAT homolog, MaGPAT2, was isolated from *M. alpina* (strain 1S-4), and it has been reported that the homolog has a substrate specificity different from that of MaGPAT1 (Patent Literature 3). That is, when they are expressed in yeast, MaGPAT1 increases the content of palmitic acid in the lipid produced by the yeast, whereas MaGPAT2 increases the content of oleic acid in the lipid produced by the yeast.

CITATION LIST

Patent Literature

Patent Literature 1: International Publication No. WO2004/087902
Patent Literature 2: U.S. Patent Publication No. 2006/0094091
Patent Literature 3: International Publication No. WO2008/156026

Non-Patent Literature

Non-Patent Literature 1: Lipids, 39, 1147-1161, 2004
Non-Patent Literature 2: Biochimica et Biophysica Acta, 1348, 17-26, 1997

Non-Patent Literature 3: Biochimica et Biophysica Acta, 1348, 10-16, 1997

Non-Patent Literature 4: The Journal of Biological Chemistry, 276 (45), 41710-41716, 2001

Non-Patent Literature 5: The Biochemical Journal, 355, 315-322, 2001

Non-Patent Literature 6: Biochemical Society Transactions, 28, 707-709, 2000

SUMMARY OF INVENTION

Technical Problem

When the previously reported GPAT genes are introduced into host cells and are expressed therein, a fatty acid composition produced by the host is restricted by their substrate specificity. Identification of a novel gene that can produce an intended fatty acid composition by introduction or expression in a host cell is required.

It is an object of the present invention to provide a protein and a nucleic acid that can achieve production of a fat having an intended compositional ratio of fatty acids, can increase the content of an intended fatty acid, or can increase the amount of a reserve lipid, triacylglycerol (TG), through expression or introduction in the host cells.

Solution to Problem

The present inventor has diligently studied to solve the above-mentioned problems. First, the inventor has analyzed the genome of a lipid-producing fungus, Mortierella alpina, and extracted sequences having a high ddgree of homology with known glycerol 3-phosphate acyltransferase (GPAT) genes from the genome. Further, in order to obtain a full-length of the open reading frame (ORF) encoding GPAT, a full-length cDNA was cloned by screening or PCR of a cDNA library. The present inventor has tried producing a fatty acid composition by introducing the gene into host cells having high proliferative ability, such as yeast, and as a result, the inventor has successfully cloned a gene related to a novel GPAT that has a different substrate specificity and can generate a fatty acid composition different from the fatty acid composition produced by the host cells expressing conventional GPAT, and the present invention has been accomplished. That is, the present invention is as follows.

(1) A nucleic acid according to any one selected from (a) to (g) below:

(a) a nucleic acid comprising a nucleotide sequence encoding a protein that consists of an amino acid sequence having deletion, substitution, or addition of one or more amino acids in the amino acid sequence set forth in SEQ ID NO: 2, SEQ ID NO: 5, or SEQ ID NO: 9 and has a glycerol 3-phosphate acyltransferase activity and/or a glycerone phosphate acyltransferase activity;

(b) a nucleic acid comprising a nucleotide sequence that is hybridizable with a nucleic acid consisting of a nucleotide sequence complementary to the nucleotide sequence set forth in SEQ ID NO: 1, SEQ ID NO: 4, or SEQ ID NO: 8 under stringent conditions and encodes a protein having a glycerol 3-phosphate acyltransferase activity and/or a glycerone phosphate acyltransferase activity;

(c) a nucleic acid comprising a nucleotide sequence that consists of a nucleotide sequence having an identity of 70% or more with the nucleotide sequence set forth in SEQ ID NO: 1, SEQ ID NO: 4, or SEQ ID NO: 8 and encodes a protein having a glycerol 3-phosphate acyltransferase activity and/or a glycerone phosphate acyltransferase activity;

(d) a nucleic acid comprising a nucleotide sequence encoding a protein that consists of an amino acid sequence having an identity of 70% or more with the amino acid sequence set forth in SEQ ID NO: 2, SEQ ID NO: 5, or SEQ ID NO: 9 and has a glycerol 3-phosphate acyltransferase activity and/or a glycerone phosphate acyltransferase activity;

(e) a nucleic acid comprising a nucleotide sequence that is hybridizable with a nucleic acid consisting of a nucleotide sequence complementary to a nucleotide sequence encoding a protein consisting of the amino acid sequence set forth in SEQ ID NO: 2, SEQ ID NO: 5, or SEQ ID NO: 9 under stringent conditions and encodes a protein having a glycerol 3-phosphate acyltransferase activity and/or a glycerone phosphate acyltransferase activity;

(f) a nucleic acid comprising a nucleotide sequence that is hybridizable with a nucleic acid consisting of a nucleotide sequence complementary to the nucleotide sequence set forth in SEQ ID NO: 7 or SEQ ID NO: 12 under stringent conditions and includes an exon encoding a protein having a glycerol 3-phosphate acyltransferase activity and/or a glycerone phosphate acyltransferase activity; and (g) a nucleic acid comprising a nucleotide sequence that consists of a nucleotide sequence having an identity of 70% or more with the nucleotide sequence set forth in SEQ ID NO: 7 or SEQ ID NO: 12 and includes an exon encoding a protein having a glycerol 3-phosphate acyltransferase activity and/or a glycerone phosphate acyltransferase activity.

(2) The nucleic acid according to aspect (1), wherein the nucleic acid is any one selected from (a) to (g) below:

(a) a nucleic acid comprising a nucleotide sequence encoding a protein that consists of an amino acid sequence having deletion, substitution, or addition of 1 to 80 amino acids in the amino acid sequence set forth in SEQ ID NO: 2, SEQ ID NO: 5, or SEQ ID NO: 9 and has a glycerol 3-phosphate acyltransferase activity and/or a glycerone phosphate acyltransferase activity;

(b) a nucleic acid comprising a nucleotide sequence that is hybridizable with a nucleic acid consisting of a nucleotide sequence complementary to the nucleotide sequence set forth in SEQ ID NO: 1, SEQ ID NO: 4, or SEQ ID NO: 8 under conditions of 2×SSC at 50° C. and encodes a protein having a glycerol 3-phosphate acyltransferase activity and/or a glycerone phosphate acyltransferase activity;

(c) a nucleic acid comprising a nucleotide sequence that consists of a nucleotide sequence having an identity of 90% or more with the nucleotide sequence set forth in SEQ ID NO: 1, SEQ ID NO: 4, or SEQ ID NO: 8 and encodes a protein having a glycerol 3-phosphate acyltransferase activity and/or a glycerone phosphate acyltransferase activity;

(d) a nucleic acid comprising a nucleotide sequence encoding a protein that consists of an amino acid sequence having an identity of 90% or more with the amino acid sequence set forth in SEQ ID NO: 2, SEQ ID NO: 5, or SEQ ID NO: 9 and has a glycerol 3-phosphate acyltransferase activity and/or a glycerone phosphate acyltransferase activity;

(e) a nucleic acid comprising a nucleotide sequence that is hybridizable with a nucleic acid consisting of a nucleotide sequence complementary to a nucleotide sequence encoding a protein consisting of the amino acid sequence set forth in SEQ ID NO: 2, SEQ ID NO: 5, or SEQ ID NO: 9 under conditions of 2×SSC at 50° C. and encodes a protein having a glycerol 3-phosphate acyltransferase activity and/or a glycerone phosphate acyltransferase activity;

(f) a nucleic acid comprising a nucleotide sequence that is hybridizable with a nucleic acid consisting of a nucleotide sequence complementary to the nucleotide sequence set forth in SEQ ID NO: 7 or SEQ ID NO: 12 under conditions of 2×SSC at 50° C. and includes an exon encoding a protein having a glycerol 3-phosphate acyltransferase activity and/or a glycerone phosphate acyltransferase activity; and (g) a nucleic acid comprising a nucleotide sequence that consists of a nucleotide sequence having an identity of 90% or more with the nucleotide sequence set forth in SEQ ID NO: 7 or SEQ ID NO: 12 and includes an exon encoding a protein having a glycerol 3-phosphate acyltransferase activity and/or a glycerone phosphate acyltransferase activity.

(3) A nucleic acid according to any one selected from (a) to (d) below:

(a) a nucleic acid comprising the nucleotide sequence set forth in SEQ ID NO: 1, SEQ ID NO: 4, or SEQ ID NO: 8 or a fragment thereof;

(b) a nucleic acid comprising a nucleotide sequence encoding a protein consisting of the amino acid sequence set forth in SEQ ID NO: 2, SEQ ID NO: 5, or SEQ ID NO: 9 or a fragment thereof;

(c) a nucleic acid comprising the nucleotide sequence set forth in SEQ ID NO: 3, SEQ ID NO: 6, or SEQ ID NO: 11 or a fragment thereof; and (d) a nucleic acid comprising the nucleotide sequence set forth in SEQ ID NO: 7 or SEQ ID NO: 12 or a fragment thereof.

(4) A nucleic acid according to any one selected from (a) to (g) below:

(a) a nucleic acid comprising a nucleotide sequence encoding a protein that consists of an amino acid sequence having deletion, substitution, or addition of one or more amino acids in the amino acid sequence set forth in SEQ ID NO: 2, SEQ ID NO: 5, or SEQ ID NO: 9 and has any one of the following activities i) to v):

i) an activity to develop a fatty acid composition containing palmitic acid at a higher proportion and palmitoleic acid at a lower proportion in yeast expressing the protein compared with those in a fatty acid composition in a host not expressing the protein;

ii) an activity to generate higher contents of fatty acids in yeast expressing the protein compared with those in a host not expressing the protein;

iii) an activity to generate a higher amount of triacylglycerol (TG) in yeast expressing the protein compared with TG in a host not expressing the protein;

iv) an activity to complement glycerol 3-phosphate acyltransferase deficiency (hereinafter, also referred to as "GPAT deficiency") of yeast (*S. cerevisiae*); and v) an activity to increase production of arachidonic acid in a host transformed with a recombinant vector containing a nucleic acid encoding the protein compared with that in a host not transformed with the vector;

(b) a nucleic acid comprising a nucleotide sequence that is hybridizable with a nucleic acid consisting of a nucleotide sequence complementary to the nucleotide sequence set forth in SEQ ID NO: 1, SEQ ID NO: 4, or SEQ ID NO: 8 under stringent conditions and encodes a protein having any one of the following activities i) to v):

i) an activity to develop a fatty acid composition containing palmitic acid at a higher proportion and palmitoleic acid at a lower proportion in yeast expressing the protein compared with those in a fatty acid composition in a host not expressing the protein;

ii) an activity to generate higher contents of fatty acids in yeast expressing the protein compared with those in a host not expressing the protein;

iii) an activity to generate a higher amount of triacylglycerol (TG) in yeast expressing the protein compared with TG in a host not expressing the protein;

iv) an activity to complement GPAT deficiency of yeast (*S. cerevisiae*); and v) an activity to increase production of arachidonic acid in a host transformed with a recombinant vector containing a nucleic acid encoding the protein compared with that in a host not transformed with the vector;

(c) a nucleic acid comprising a nucleotide sequence that consists of a nucleotide sequence having an identity of 70% or more with the nucleotide sequence set forth in SEQ ID NO: 1, SEQ ID NO: 4, or SEQ ID NO: 8 and encodes a protein having any one of the following activities i) to v):

i) an activity to develop a fatty acid composition containing palmitic acid at a higher proportion and palmitoleic acid at a lower proportion in yeast expressing the protein compared with those in a fatty acid composition in a host not expressing the protein;

ii) an activity to generate higher contents of fatty acids in yeast expressing the protein compared with those in a host not expressing the protein;

iii) an activity to generate a higher amount of triacylglycerol (TG) in yeast expressing the protein compared with TG in a host not expressing the protein;

iv) an activity to complement GPAT deficiency of yeast (*S. cerevisiae*); and v) an activity to increase production of arachidonic acid in a host transformed with a recombinant vector containing a nucleic acid encoding the protein compared with that in a host not transformed with the vector;

(d) a nucleic acid comprising a nucleotide sequence encoding a protein that consists of an amino acid sequence having an identity of 70% or more with the amino acid sequence set forth in SEQ ID NO: 2, SEQ ID NO: 5, or SEQ ID NO: 9 and has any one of the following activities i) to v):

i) an activity to develop a fatty acid composition containing palmitic acid at a higher proportion and palmitoleic acid at a lower proportion in yeast expressing the protein compared with those in a fatty acid composition in a host not expressing the protein;

ii) an activity to generate higher contents of fatty acids in yeast expressing the protein compared with those in a host not expressing the protein;

iii) an activity to generate a higher amount of triacylglycerol (TG) in yeast expressing the protein compared with TG in a host not expressing the protein;

iv) an activity to complement GPAT deficiency of yeast (*S. cerevisiae*); and v) an activity to increase production of arachidonic acid in a host transformed with a recombinant vector containing a nucleic acid encoding the protein compared with that in a host not transformed with the vector;

(e) a nucleic acid comprising a nucleotide sequence that is hybridizable with a nucleic acid consisting of a nucleotide sequence complementary to a nucleotide sequence encoding a protein consisting of the amino acid sequence set forth in SEQ ID NO: 2, SEQ ID NO: 5, or SEQ ID NO: 9 under stringent conditions and encodes a protein having any one of the following activities i) to v):

i) an activity to develop a fatty acid composition containing palmitic acid at a higher proportion and palmitoleic acid at a lower proportion in yeast expressing the protein compared with those in a fatty acid composition in a host not expressing the protein;

ii) an activity to generate higher contents of fatty acids in yeast expressing the protein compared with those in a host not expressing the protein;

iii) an activity to generate a higher amount of triacylglycerol (TG) in yeast expressing the protein compared with TG in a host not expressing the protein;

iv) an activity to complement GPAT deficiency of yeast (*S. cerevisiae*); and v) an activity to increase production of arachidonic acid in a host transformed with a recombinant vector containing a nucleic acid encoding the protein compared with that in a host not transformed with the vector;

(f) a nucleic acid comprising a nucleotide sequence that is hybridizable with a nucleic acid consisting of a nucleotide sequence complementary to the nucleotide sequence set forth in SEQ ID NO: 7 or SEQ ID NO: 12 under stringent conditions and includes an exon encoding a protein having any one of the following activities i) to v):

i) an activity to develop a fatty acid composition containing palmitic acid at a higher proportion and palmitoleic acid at a lower proportion in yeast expressing the protein compared with those in a fatty acid composition in a host not expressing the protein;

ii) an activity to generate higher contents of fatty acids in yeast expressing the protein compared with those in a host not expressing the protein;

iii) an activity to generate a higher amount of triacylglycerol (TG) in yeast expressing the protein compared with TG in a host not expressing the protein;

iv) an activity to complement GPAT deficiency of yeast (*S. cerevisiae*); and v) an activity to increase production of arachidonic acid in a host transformed with a recombinant vector containing a nucleic acid encoding the protein compared with that in a host not transformed with the vector; and (g) a nucleic acid comprising a nucleotide sequence that consists of a nucleotide sequence having an identity of 70% or more with the nucleotide sequence set forth in SEQ ID NO: 7 or SEQ ID NO: 12 and includes an exon encoding a protein having any one of the following activities i) to v):

i) an activity to develop a fatty acid composition containing palmitic acid at a higher proportion and palmitoleic acid at a lower proportion in yeast expressing the protein compared with those in a fatty acid composition in a host not expressing the protein;

ii) an activity to generate higher contents of fatty acids in yeast expressing the protein compared with those in a host not expressing the protein;

iii) an activity to generate a higher amount of triacylglycerol (TG) in yeast expressing the protein compared with TG in a host not expressing the protein;

iv) an activity to complement GPAT deficiency of yeast (*S. cerevisiae*); and v) an activity to increase production of arachidonic acid in a host transformed with a recombinant vector containing a nucleic acid encoding the protein compared with that in a host not transformed with the vector.

(5) The nucleic acid according to aspect (4), wherein the nucleic acid is any one selected from (a) to (g) below:

(a) a nucleic acid comprising a nucleotide sequence including an exon encoding a protein that consists of an amino acid sequence having deletion, substitution, or addition of 1 to 80 amino acids in the amino acid sequence set forth in SEQ ID NO: 2, SEQ ID NO: 5, or SEQ ID NO: 9 and has any one of the following activities i) to v):

i) an activity to develop a fatty acid composition containing palmitic acid at a higher proportion and palmitoleic acid at a lower proportion in yeast expressing the protein compared with those in a fatty acid composition in a host not expressing the protein;

ii) an activity to generate higher contents of fatty acids in yeast expressing the protein compared with those in a host not expressing the protein;

iii) an activity to generate a higher amount of triacylglycerol (TG) in yeast expressing the protein compared with TG in a host not expressing the protein; iv) an activity to complement GPAT deficiency of yeast (*S. cerevisiae*); and v) an activity to increase production of arachidonic acid in a host transformed with a recombinant vector containing a nucleic acid encoding the protein compared with that in a host not transformed with the vector;

(b) a nucleic acid comprising a nucleotide sequence that is hybridizable with a nucleic acid consisting of a nucleotide sequence complementary to the nucleotide sequence set forth in SEQ ID NO: 1, SEQ ID NO: 4, or SEQ ID NO: 8 under conditions of 2×SSC at 50° C. and includes an exon encoding a protein having any one of the following activities i) to v):

i) an activity to develop a fatty acid composition containing palmitic acid at a higher proportion and palmitoleic acid at a lower proportion in yeast expressing the protein compared with those in a fatty acid composition in a host not expressing the protein;

ii) an activity to generate higher contents of fatty acids in yeast expressing the protein compared with those in a host not expressing the protein;

iii) an activity to generate a higher amount of triacylglycerol (TG) in yeast expressing the protein compared with TG in a host not expressing the protein;

iv) an activity to complement GPAT deficiency of yeast (*S. cerevisiae*); and v) an activity to increase production of arachidonic acid in a host transformed with a recombinant vector containing a nucleic acid encoding the protein compared with that in a host not transformed with the vector;

(c) a nucleic acid comprising a nucleotide sequence that consists of a nucleotide sequence having an identity of 90% or more with the nucleotide sequence set forth in SEQ ID NO: 1, SEQ ID NO: 4, or SEQ ID NO: 8 and includes an exon encoding a protein having any one of the following activities i) to v):

i) an activity to develop a fatty acid composition containing palmitic acid at a higher proportion and palmitoleic acid at a lower proportion in yeast expressing the protein compared with those in a fatty acid composition in a host not expressing the protein;

ii) an activity to generate higher contents of fatty acids in yeast expressing the protein compared with those in a host not expressing the protein;

iii) an activity to generate a higher amount of triacylglycerol (TG) in yeast expressing the protein compared with TG in a host not expressing the protein;

iv) an activity to complement GPAT deficiency of yeast (*S. cerevisiae*); and v) an activity to increase production of arachidonic acid in a host transformed with a recombinant vector containing a nucleic acid encoding the protein compared with that in a host not transformed with the vector;

(d) a nucleic acid comprising a nucleotide sequence that includes an exon encoding a protein that consists of an amino acid sequence having an identity of 90% or more with the amino acid sequence set forth in SEQ ID NO: 2, SEQ ID NO: 5, or SEQ ID NO: 9 and has any one of the following activities i) to v):

i) an activity to develop a fatty acid composition containing palmitic acid at a higher proportion and palmitoleic acid at a lower proportion in yeast expressing the protein compared with those in a fatty acid composition in a host not expressing the protein;

ii) an activity to generate higher contents of fatty acids in yeast expressing the protein compared with those in a host not expressing the protein;

iii) an activity to generate a higher amount of triacylglycerol (TG) in yeast expressing the protein compared with TG in a host not expressing the protein;

iv) an activity to complement GPAT deficiency of yeast (*S. cerevisiae*); and v) an activity to increase production of arachidonic acid in a host transformed with a recombinant vector containing a nucleic acid encoding the protein compared with that in a host not transformed with the vector;

(e) a nucleic acid comprising a nucleotide sequence that is hybridizable with a nucleic acid consisting of a nucleotide sequence complementary to a nucleotide sequence encoding a protein that consists of the amino acid sequence set forth in SEQ ID NO: 2, SEQ ID NO: 5, or SEQ ID NO: 9 under conditions of 2×SSC at 50° C. and includes an exon encoding a protein having any one of the following activities i) to v):

i) an activity to develop a fatty acid composition containing palmitic acid at a higher proportion and palmitoleic acid at a lower proportion in yeast expressing the protein compared with those in a fatty acid composition in a host not expressing the protein;

ii) an activity to generate higher contents of fatty acids in yeast expressing the protein compared with those in a host not expressing the protein;

iii) an activity to generate a higher amount of triacylglycerol (TG) in yeast expressing the protein compared with TG in a host not expressing the protein;

iv) an activity to complement GPAT deficiency of yeast (*S. cerevisiae*); and v) an activity to increase production of arachidonic acid in a host transformed with a recombinant vector containing a nucleic acid encoding the protein compared with that in a host not transformed with the vector;

(f) a nucleic acid comprising a nucleotide sequence that is hybridizable with a nucleic acid comprising a nucleotide sequence complementary to the nucleotide sequence set forth in SEQ ID NO: 7 or SEQ ID NO: 12 under conditions of 2×SSC at 50° C. and includes an exon encoding a protein having any one of the following activities i) to v):

i) an activity to develop a fatty acid composition containing palmitic acid at a higher proportion and palmitoleic acid at a lower proportion in yeast expressing the protein compared with those in a fatty acid composition in a host not expressing the protein;

ii) an activity to generate higher contents of fatty acids in yeast expressing the protein compared with those in a host not expressing the protein;

iii) an activity to generate a higher amount of triacylglycerol (TG) in yeast expressing the protein compared with TG in a host not expressing the protein;

iv) an activity to complement GPAT deficiency of yeast (*S. cerevisiae*); and v) an activity to increase production of arachidonic acid in a host transformed with a recombinant vector containing a nucleic acid encoding the protein compared with that in a host not transformed with the vector; and (g) a nucleic acid comprising a nucleotide sequence that consists of a nucleotide sequence having an identity of 90% or more with the nucleotide sequence set forth in SEQ ID NO: 7 or SEQ ID NO: 12 and includes an exon encoding a protein having any one of the following activities i) to v):

i) an activity to develop a fatty acid composition containing palmitic acid at a higher proportion and palmitoleic acid at a lower proportion in yeast expressing the protein compared with those in a fatty acid composition in a host not expressing the protein;

ii) an activity to generate higher contents of fatty acids in yeast expressing the protein compared with those in a host not expressing the protein;

iii) an activity to generate a higher amount of triacylglycerol (TG) in yeast expressing the protein compared with TG in a host not expressing the protein;

iv) an activity to complement GPAT deficiency of yeast (*S. cerevisiae*); and v) an activity to increase production of arachidonic acid in a host transformed with a recombinant vector containing a nucleic acid encoding the protein compared with that in a host not transformed with the vector.

(6) A protein selected from (a) and (b) below:

(a) a protein consisting of an amino acid sequence having deletion, substitution, or addition of one or more amino acids in the amino acid sequence set forth in SEQ ID NO: 2, SEQ ID NO: 5, or SEQ ID NO: 9 and having a glycerol 3-phosphate acyltransferase activity and/or a glycerone phosphate acyltransferase activity; and (b) a protein consisting of an amino acid sequence having an identity of 70% or more with the amino acid sequence set forth in SEQ ID NO: 2, SEQ ID NO: 5, or SEQ ID NO: 9 and having a glycerol 3-phosphate acyltransferase activity and/or a glycerone phosphate acyltransferase activity.

(7) A protein selected from (a) and (b) below:

(a) a protein consisting of an amino acid sequence having deletion, substitution, or addition of 1 to 80 amino acids in the amino acid sequence set forth in SEQ ID NO: 2, SEQ ID NO: 5, or SEQ ID NO: 9 and having a glycerol 3-phosphate acyltransferase activity and/or a glycerone phosphate acyltransferase activity; and (b) a protein consisting of an amino acid sequence having an identity of 90% or more with the amino acid sequence set forth in SEQ ID NO: 2, SEQ ID NO: 5, or SEQ ID NO: 9 and having a glycerol 3-phosphate acyltransferase activity and/or a glycerone phosphate acyltransferase activity.

(8) A protein selected from (a) and (b) below:

(a) a protein consisting of an amino acid sequence having deletion, substitution, or addition of one or more amino acids in the amino acid sequence set forth in SEQ ID NO: 2, SEQ ID NO: 5, or SEQ ID NO: 9 and having any one of the following activities i) to v):

i) an activity to develop a fatty acid composition containing palmitic acid at a higher proportion and palmitoleic acid at a lower proportion in yeast expressing the protein compared with those in a fatty acid composition in a host not expressing the protein;

ii) an activity to generate higher contents of fatty acids in yeast expressing the protein compared with those in a host not expressing the protein;

iii) an activity to generate a higher amount of triacylglycerol (TG) in yeast expressing the protein compared with TG in a host not expressing the protein;

iv) an activity to complement GPAT deficiency of yeast (*S. cerevisiae*); and v) an activity to increase production of arachidonic acid in a host transformed with a recombinant vector containing a nucleic acid encoding the protein compared with that in a host not transformed with the vector; and (b) a protein consisting of an amino acid sequence having an identity of 70% or more with the amino acid sequence set forth in SEQ ID NO: 2, SEQ ID NO: 5, or SEQ ID NO: 9 and having any one of the following activities i) to v):

i) an activity to develop a fatty acid composition containing palmitic acid at a higher proportion and palmitoleic acid at a lower proportion in yeast expressing the protein compared with those in a fatty acid composition in a host not expressing the protein;

ii) an activity to generate higher contents of fatty acids in yeast expressing the protein compared with those in a host not expressing the protein;

iii) an activity to generate a higher amount of triacylglycerol (TG) in yeast expressing the protein compared with TG in a host not expressing the protein;

iv) an activity to complement GPAT deficiency of yeast (*S. cerevisiae*); and v) an activity to increase production of arachidonic acid in a host transformed with a recombinant vector containing a nucleic acid encoding the protein compared with that in a host not transformed with the vector.

(9) A protein selected from (a) and (b) below:

(a) a protein consisting of an amino acid sequence having deletion, substitution, or addition of 1 to 80 amino acids in the amino acid sequence set forth in SEQ ID NO: 2, SEQ ID NO: 5, or SEQ ID NO: 9 and having any one of the following activities i) to v):

i) an activity to develop a fatty acid composition containing palmitic acid at a higher proportion and palmitoleic acid at a lower proportion in yeast expressing the protein compared with those in a fatty acid composition in a host not expressing the protein;

ii) an activity to generate higher contents of fatty acids in yeast expressing the protein compared with those in a host not expressing the protein;

iii) an activity to generate a higher amount of triacylglycerol (TG) in yeast expressing the protein compared with TG in a host not expressing the protein;

iv) an activity to complement GPAT deficiency of yeast (*S. cerevisiae*); and v) an activity to increase production of arachidonic acid in a host transformed with a recombinant vector containing a nucleic acid encoding the protein compared with that in a host not transformed with the vector; and (b) a protein consisting of an amino acid sequence having an identity of 90% or more with the amino acid sequence set forth in SEQ ID NO: 2, SEQ ID NO: 5, or SEQ ID NO: 9 and having any one of the following activities i) to v):

i) an activity to develop a fatty acid composition containing palmitic acid at a higher proportion and palmitoleic acid at a lower proportion in yeast expressing the protein compared with those in a fatty acid composition in a host not expressing the protein;

ii) an activity to generate higher contents of fatty acids in yeast expressing the protein compared with those in a host not expressing the protein;

iii) an activity to generate a higher amount of triacylglycerol (TG) in yeast expressing the protein compared with TG in a host not expressing the protein;

iv) an activity to complement GPAT deficiency of yeast (*S. cerevisiae*); and v) an activity to increase production of arachidonic acid in a host transformed with a recombinant vector containing a nucleic acid encoding the protein compared with that in a host not transformed with the vector.

(10) A protein consisting of the amino acid sequence set forth in SEQ ID NO: 2, SEQ ID NO: 5, or SEQ ID NO: 9.

(11) A recombinant vector comprising the nucleic acid according to any one of aspects (1) to (5).

(12) A transformant transformed with the recombinant vector according to aspect (11).

(13) A fatty acid composition comprising a fatty acid or a lipid obtainable by culturing the transformant according to aspect (12).

(14) A method of producing a fatty acid composition, comprising collecting a fatty acid or a lipid from a culture obtained by culturing the transformant according to aspect (12).

(15) A food comprising the fatty acid composition according to aspect (13).

Advantageous Effects of Invention

The GPAT of the present invention has substrate specificity different from that of a conventional GPAT and can allow a host to produce fatty acids having a composition different from that of fatty acids produced by a host expressing a conventional GPAT. This can provide lipids having intended characteristics and effects and is therefore useful in application to foods, cosmetics, pharmaceuticals, soap, etc.

The GPAT of the present invention can enhance the producibility of fatty acids and reserve lipids and thus can enhance the productivity of polyunsaturated fatty acids in microorganisms and plants, and is preferable.

BRIEF DESCRIPTION OF DRAWINGS

FIG. 1-1 shows a comparison between a genomic sequence (SEQ ID NO: 7) and a CDS sequence (SEQ ID NO: 3) of MaGPAT4 derived from a *M. alpina* strain 1S-4.

FIG. 1-2 is a continuation of FIG. 1-1.

FIG. 1-3 is a continuation of FIG. 1-2.

FIG. 2-1 shows a CDS sequence (SEQ ID NO: 3) of MaGPAT4 derived from *M. alpina* strain 1S-4 and an amino acid sequence (SEQ ID NO: 2) deduced therefrom, where the double underline shows a region which is hit as a reagion having a high homology with an acyltransferase (accession No. PF01553) motif of pfam.

FIG. 2-2 is a continuation of FIG. 2-1.

FIG. 3-1 shows a comparison between a genomic sequence (SEQ ID NO: 12) and a CDS sequence (SEQ ID NO: 10) of a MaGPAT5 derived from *M. alpina* strain 1S-4.

FIG. 3-2 is a continuation of FIG. 3-1.

FIG. 4-1 shows the cDNA sequence (SEQ ID NO: 11) of MaGPAT5 derived from *M. alpina* strain 1S-4 and an amino acid sequence (SEQ ID NO: 9) deduced therefrom.

FIG. 4-2 is a continuation of FIG. 4-1.

FIG. 5 shows a comparison between a deduced amino acid sequence (SEQ ID NO: 2) of MaGPAT4 derived from *M. alpina* strain 1S-4, an amino acid sequence (SEQ ID NO: 21; GenBank accession No. XP_001224211) of a presumed protein derived from ascomycete *Chaetomium globosum* CBS 148.51, and an amino acid sequence (SEQ ID NO: 22; GenBank accession No. BAE78043) of GPAT, plsB protein, derived from *E. coli*, where the single underline shows a region having a high homology with an acyltransferase (accession No. PF01553) motif of pfam. In particular, a region of a well-conserved GPAT homolog is shown by the double underline, the symbol * indicates an amino acid residue important for acyltransferase activity, and the symbol + indicates an amino acid residue necessary for binding with G3P.

FIG. 6-1 shows a comparison between a deduced amino acid sequence (SEQ ID NO: 9) of MaGPAT5 derived from *M. alpina* strain 1S-4, an amino acid sequence (SEQ ID NO: 23; GenBank accession No. XP_759516) of a presumed protein UM03369 derived from basidiomycete *Ustilago maydis* 521, and amino acid sequences, SCT1 (YBL011W) (SEQ ID NO: 24) and GPT2 (YKR067W) (SEQ ID NO: 25) of GPAT derived from *S. cerevisiae*, where the double underline shows a region of a well-conserved GPAT homolog, the symbol * indicates an amino acid residue important for acyltransferase activity, and the symbol + indicates an amino acid residue necessary for binding with G3P.

FIG. 6-2 is a continuation of FIG. 6-1.

FIG. 7 relates to graphs showing a compositional ratio of fatty acids in lipid fractions when expression was induced with galactose by culturing yeast transformed with a plasmid containing MaGPAT4-long or MaGPAT4 linked to a galactose-inducible promoter in a SG-Trp medium.

DESCRIPTION OF EMBODIMENTS

Figures 2, 6, 7:
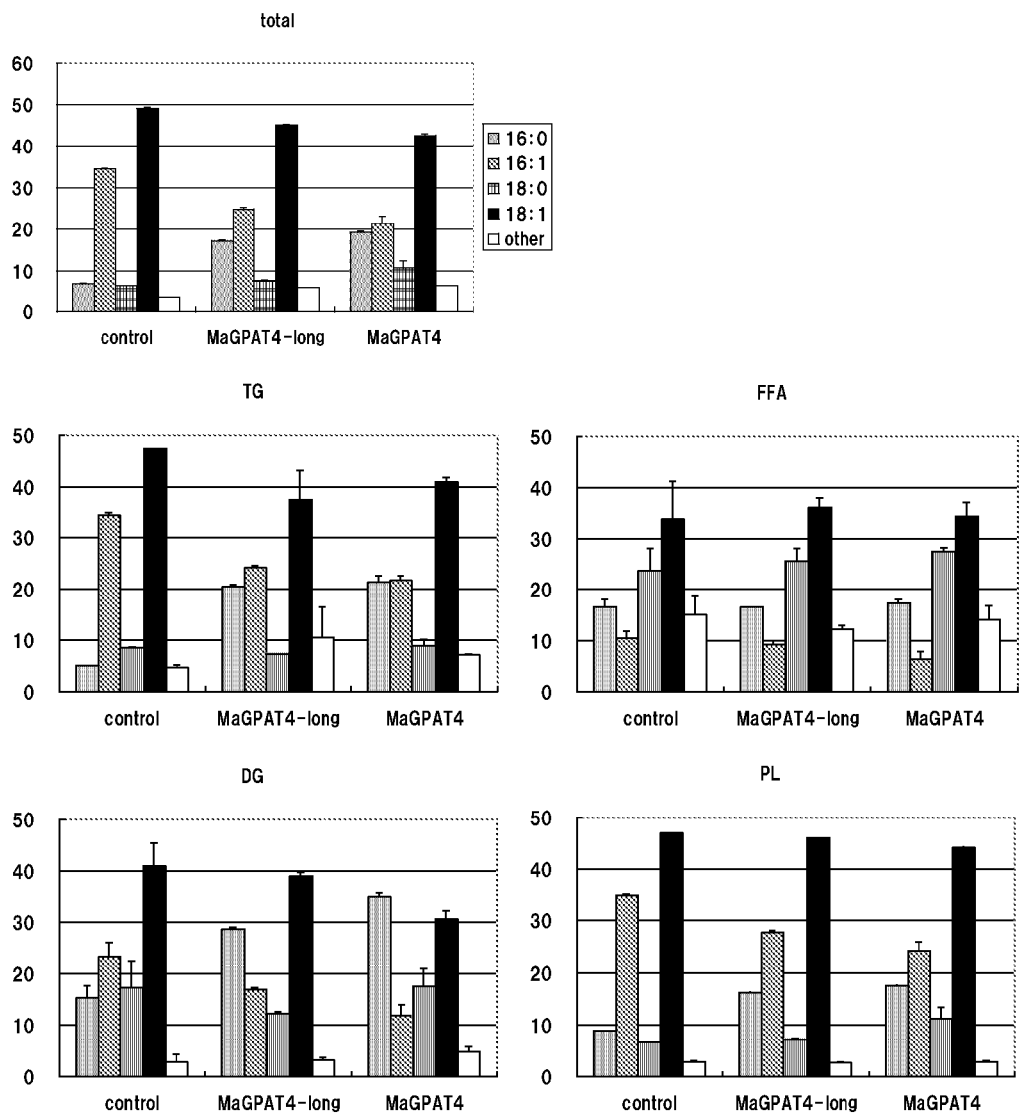

The present invention relates to a novel acyltransferase gene derived from *Mortierella* and use thereof. The acyltransferase of the present invention may be an acyltransferase that acylates glycerol 3-phosphate to generate lysophosphatidic acid and/or that transfers an acyl group to a hydroxyl group of glycerone phosphate.

The acyltransferase of the present invention is an enzyme that catalyzes a transfer reaction of an acyl group to glycerol 3-phosphate and/or glycerone phosphate. The acyl-group receptor for the enzyme of the present invention is usually glycerol 3-phosphate and/or glycerone phosphate, but is not limited thereto.

Accordingly, the acyltransferase of the present invention may have an activity as a glycerol 3-phosphate acyltransferase (GPAT) and/or a glycerone phosphate O-acyltransferase (GNPAT). In this specification, however, the enzyme of the present invention may also be conveniently referred to as "glycerol 3-phosphate acyltransferase" or "GPAT" regardless of its actual activity.

Nucleic Acid Encoding Glycerol 3-Phosphate Acyltransferase of the Present Invention Examples of glycerol 3-phosphate acyltransferase (GPAT) of the present invention encompass MaGPAT4, MaGPAT4-long, and MaGPAT5. The correspondence between cDNA, CDS, and ORF encoding MaGPAT4, MaGPAT4-long, or MaGPAT5, and a deduced amino acid sequence thereof is summarized in Table 1.

TABLE 1

|  | MaGPAT4 | | | MaGPAT4-long | |
|---|---|---|---|---|---|
|  | SEQ ID NO | Corresponding region in SEQ ID NO: 3 | Corresponding region in MaGPAT4-long | SEQ ID NO | Corresponding region in SEQ ID NO: 6 |
| CDS (cDNA) | SEQ ID NO: 3 | ***** | Positions 169 to 2646 in SEQ ID NO: 6 | SEQ ID NO: 6 | ***** |
| ORF | SEQ ID NO: 1 | Positions 1 to 2475 | Positions 169 to 2643 in SEQ ID NO: 4 | SEQ ID NO: 4 | Positions 1 to 2643 |
| Amino acid sequence | SEQ ID NO: 2 | ***** | Positions 57 to 881 in SEQ ID NO: 5 | SEQ ID NO: 5 | ***** |

|  | MaGPAT5 | |
|---|---|---|
|  | SEQ ID NO | Corresponding region in SEQ ID 11 |
| cDNA | SEQ ID NO: 11 | ***** |
| CDS | SEQ ID NO: 10 | Positions 225 to 2591 |
| ORF | SEQ ID NO: 8 | Positions 225 to 2588 |
| Amino acid sequence | SEQ ID NO: 9 | ***** |

Sequences related to MaGPAT4 of the present invention include SEQ ID NO: 2 showing the amino acid sequence of MaGPAT4; SEQ ID NO: 1 showing the sequence of the ORF region of MaGPAT4; and SEQ ID NO: 3 showing the sequence of the CDS or cDNA of MaGPAT4. Among these sequences, SEQ ID NO: 1 corresponds to the nucleotides 1 to 2475 in the sequence set forth in SEQ ID NO: 3. Sequences related to MaGPAT4-long of the present invention include SEQ ID NO: 5 showing the amino acid sequence of MaG-PAT4-long; SEQ ID NO: 4 showing the sequence of the ORF region of MaGPAT4-long; and SEQ ID NO: 6 showing the sequence of the CDS or cDNA region of MaGPAT4-long. Among them, SEQ ID NO: 1 corresponds to the nucleotides 1 to 2475 in the sequence set forth in SEQ ID NO: 3. Among these sequences, SEQ ID NO: 4 corresponds to the nucleotides 1 to 2643 in the sequence set forth in SEQ ID NO: 6. As shown in the table, the amino acid sequence and the nucleotide sequence of MaGPAT4 constitute parts of the amino acid sequence and the nucleotide sequence of MaGPAT4-long, respectively. SEQ ID NO: 7 shows a genomic nucleotide sequence encoding MaGPAT4 and MAGPAT4-long of the present invention. In the case of encoding MaGPAT4, the genomic sequence set forth in SEQ ID NO: 7 is composed of ten exons and nine introns, and the exon regions correspond to the nucleotides 596 to 744, 850 to 924, 1302 to 1396, 1480 to 1726, 1854 to 2279, 2370 to 2632, 2724 to 3299, 3390 to 3471, 3575 to 4024, and 4133 to 4248 in SEQ ID NO: 7. In the case of encoding MaGPAT4-long, the genomic sequence set forth in SEQ ID NO: 7 is composed of ten exons and nine introns, and the exon regions correspond to the nucleotides 428 to 744, 850 to 924, 1302 to 1396, 1480 to 1726, 1854 to 2279, 2370 to 2632, 2724 to 3299, 3390 to 3471, 3575 to 4024, and 4133 to 4248 in SEQ ID NO: 7.

Sequences related to MaGPAT5 of the present invention include SEQ ID NO: 9 showing the amino acid sequence of MaGPAT5; SEQ ID NO: 8 showing the sequence of the ORF region of MaGPAT5; SEQ ID NO: 10 showing the sequence of the CDS region of MaGPAT5; and SEQ ID NO: 11 showing the sequence of the cDNA for MaGPAT5. Among these sequences, SEQ ID NO: 10 corresponds to the nucleotides 225 to 2591 in the sequence set forth in SEQ ID NO: 11; and SEQ ID NO: 8 corresponds to the nucleotides 225 to 2588 in the sequence set forth in SEQ ID NO: 11 and the nucleotides 1 to 2364 in the sequence set forth in SEQ ID NO: 10. SEQ ID NO: 12 shows a genomic nucleotide sequence encoding MaGPAT5 of the present invention. The genomic sequence set forth in SEQ ID NO: 12 is composed of three exons and two introns, and the exon regions correspond to the nucleotides 1 to 302, 457 to 1676, and 1754 to 2598 in SEQ ID NO: 12.

The nucleic acids of the present invention encompass single-stranded and double-stranded DNAs and also their complementary RNAs, which may be either naturally occurring or artificially prepared. Examples of DNA include, but not limited to, genomic DNAs, cDNAs corresponding to the genomic DNAs, chemically synthesized DNAs, PCR-amplified DNAs, combinations thereof, and DNA/RNA hybrids.

Preferred embodiments for the nucleic acids of the present invention include (a) nucleic acids containing the nucleotide sequence set forth in SEQ ID NO: 1, SEQ ID NO: 4, or SEQ ID NO: 8, (b) nucleic acids containing a nucleotide sequence encoding a protein consisting of the amino acid sequence set forth in SEQ ID NO: 2, SEQ ID NO: 5, or SEQ ID NO: 9, (c) nucleic acids containing the nucleotide sequence set forth in SEQ ID NO: 3, SEQ ID NO: 6, or SEQ ID NO: 11, and (d) nucleic acids containing the nucleotide sequence set forth in SEQ ID NO: 7 or SEQ ID NO: 12.

In order to obtain these nucleotide sequences, nucleotide sequence data of ESTs or genomic DNAs from organisms having GPAT activity may be used to search for a nucleotide sequence encoding a protein having a high identity with known proteins having GPAT activity. Preferred organisms having GPAT activity are lipid-producing fungi including, but not limited to, M. alpina.

For EST analysis, a cDNA library is first prepared. The cDNA library may be prepared by referring to "Molecular Cloning, A Laboratory Manual 3rd ed." (Cold Spring Harbor Press (2001)). Alternatively, a commercially available cDNA library preparation kit may be used. Examples of a method of preparing a cDNA library suitable for the present invention are as follows. That is, an appropriate strain of M. alpina, a lipid-producing fungus, is inoculated into an appropriate medium and is pre-cultured for an appropriate period. Culture conditions suitable for this pre-culture are, for example, a medium composition of 1.8% glucose and 1% yeast extract, pH 6.0, a culture period of 3 to 4 days, and a culture temperature of 28° C. The pre-cultured product is then subjected to main culture under appropriate conditions. A medium composition suitable for the main culture is, for example, 1.8% glucose, 1% soybean powder, 0.1% olive oil, 0.01% Adekanol, 0.3% $KH_2PO_4$, 0.1% $Na_2SO_4$, 0.05% $CaCl_2.2H_2O$, and 0.05% $MgCl_2.6H_2O$, and pH 6.0. Culture conditions suitable for the main culture are, for example, aeration and agitation culture at 300 rpm, 1 vvm, and 26° C. for 8 days. An appropriate amount of glucose may be added during culture. The cultured product is sampled at appropriate time points during the main culture, from which the cells are collected to prepare total RNA. The total RNA may be prepared by any known method such as a guanidine hydrochloride/CsCl method. From the resulting total RNA, poly(A)$^+$ RNA can be purified using a commercially available kit, and a cDNA library can be prepared using a commercially available kit. The nucleotide sequence of any clone from the prepared cDNA library is determined using primers that are designed on a vector to allow determination of the nucleotide sequence of an insert. As a result, ESTs can be obtained. For example, when a ZAP-cDNA GigapackIII Gold Cloning Kit (Stratagene) is used for preparing a cDNA library, directional cloning is possible.

In analysis of genomic DNA, cells of an organism having GPAT activity are cultured, and genomic DNA is prepared from the cells. The nucleotide sequence of the resulting genomic DNA is determined, and the determined nucleotide sequence is assembled. From the finally obtained supercontig sequence, a sequence encoding an amino acid sequence having a high homology with the amino acid sequence of a known protein having GPAT activity is searched. From the supercontig sequence giving a hit as that encoding such an amino acid sequence, primers are prepared. PCR is performed using the cDNA library as a template, and the resulting DNA fragment is inserted into a plasmid for cloning. PCR is performed using the cloned plasmid as a template and the above-mentioned primers to prepare a probe. The cDNA library is screened using the resulting probe.

A homology search of deduced amino acid sequences of MaGPAT4 and MaGPAT5 of the present invention was performed with BLASTp program against amino acid sequences registered in GenBank. An amino acid sequence having a high identity with that of MaGPAT4 is an amino acid sequence (GenBank accession No. XP_001224211) of a presumed protein derived from ascomycete *Chaetomium globosum* CBS148.51, and the identity is 39.3%. The amino acid sequence of MaGPAT4 also has a homology with glycerone phosphate O-acyltransferase (GNPAT; GenBank accession No. AAH00450) derived from human being, and the amino acid identity is 22.6%. In addition, the amino acid identity between MaGPAT4 and plsB protein (GenBank accession No. BAE78043), which is GPAT derived from *Escherichia coli* (*E. coli*), is 17.6%. An amino acid sequence having a high identity with that of MaGPAT5 is an amino acid sequence (GenBank accession No. XP_759516) of a presumed protein derived from basidiomycete *Ustilago maydis* 521, and the identity is 15.4%.

The present invention also encompasses nucleic acids functionally equivalent to a nucleic acid comprising the nucleotide sequence set forth in SEQ ID NO: 1, SEQ ID NO: 4, or SEQ ID NO: 8 (hereinafter also referred to as "the nucleotide sequence of the present invention") or a nucleotide sequence encoding a protein consisting of the amino acid sequence set forth in SEQ ID NO: 2, SEQ ID NO: 5, or SEQ ID NO: 9 (hereinafter also referred to as "the amino acid sequence of the present invention"). The term "functionally equivalent" refers to that a protein encoded by the nucleotide sequence of the present invention and a protein consisting of the amino acid sequence of the present invention have a glycerol 3-phosphate acyltransferase (GPAT) activity and/or a glycerone phosphate O-acyltransferase (GNPAT) activity. In addition, the term "functionally equivalent" may refer to exsitense of any one of the following activities, in regard of a compositional ratio of fatty acids in a host expressing a protein encoded by a nucleotide sequence of the present invention or a protein consisting of an amino acid sequence of the present invention:

i) an activity to develop a fatty acid composition containing palmitic acid at a higher proportion and palmitoleic acid at a lower proportion in yeast expressing the protein compared with those in the fatty acid composition of a host not expressing the protein;

ii) an activity to generate higher contents of fatty acids in yeast expressing the protein compared with those in a host not expressing the protein;

iii) an activity to generate a higher amount of triacylglycerol (TG) in yeast expressing the protein compared with TG in a host not expressing the protein;

iv) an activity to complement glycerol 3-phosphate acyltransferase deficiency (GPAT deficiency) of yeast (*S. cerevisiae*), wherein the DPAT deficiency is due to deficiencies of, preferably, both an SCT1 gene and a GPT2 gene; and/or v) an activity to increase production of arachidonic acid in a host transformed with a recombinant vector containing a nucleic acid encoding the protein compared with that in a host not transformed with the vector.

Such nucleic acids that are functionally equivalent to the nucleic acids of the present invention include nucleic acids comprising nucleotide sequences shown in any one selected from (a) to (g) below. It should be noted that in the descriptions of the nucleotide sequences listed below, the term "the activity of the present invention" refers to "the GPAT activity, the GNPAT activity, or at least one activity selected from the activities i) to v) described above."

(a) A nucleic acid comprising a nucleotide sequence encoding a protein that consists of an amino acid sequence having deletion, substitution, or addition of one or more amino acids in the amino acid sequence set forth in SEQ ID NO: 2, SEQ ID NO: 5, or SEQ ID NO: 9 and has the activity of the present invention Examples of the nucleotide sequence contained in the nucleic acid of the present invention encompass nucleotide sequences encoding a protein that consists of an amino acid sequence having deletion, substitution, or addition of one or more amino acids in the amino acid sequence set forth in SEQ ID NO: 2, SEQ ID NO: 5, or SEQ ID NO: 9 and has the activity of the present invention.

Specifically, the nucleotide sequence contained in the nucleic acid of the present invention is a nucleotide sequence encoding a protein having the above-described activity of the present invention and consisting of:

(i) an amino acid sequence having deletion of one or more (preferably one to several (e.g., 1 to 250, 1 to 200, 1 to 150, 1 to 100, 1 to 80, 1 to 75, 1 to 50, 1 to 30, 1 to 25, 1 to 20, or 1 to 15, more preferably 10, 9, 8, 7, 6, 5, 4, 3, 2, or 1)) amino acids in the amino acid sequence set forth in SEQ ID NO: 2, SEQ ID NO: 5, or SEQ ID NO: 9;

(ii) an amino acid sequence having substitution of one or more (preferably one to several (e.g., 1 to 250, 1 to 200, 1 to 150, 1 to 100, 1 to 80, 1 to 75, 1 to 50, 1 to 30, 1 to 25, 1 to 20, or 1 to 15, more preferably 10, 9, 8, 7, 6, 5, 4, 3, 2, or 1)) amino acids in the amino acid sequence set forth in SEQ ID NO: 2, SEQ ID NO: 5, or SEQ ID NO: 9;

(iii) an amino acid sequence having addition of one or more (preferably one to several (e.g., 1 to 250, 1 to 200, 1 to 150, 1 to 100, 1 to 80, 1 to 75, 1 to 50, 1 to 30, 1 to 25, 1 to 20, or 1 to 15, more preferably 10, 9, 8, 7, 6, 5, 4, 3, 2, or 1)) amino acids in the amino acid sequence set forth in SEQ ID NO: 2, SEQ ID NO: 5, or SEQ ID NO: 9; or (iv) an amino acid sequence in any combination of (i) to (iii) above.

Among the above, substitution is preferably conservative, which means replacement of a certain amino acid residue by another residue having similar physical and chemical characteristics. It may be any substitution that does not substantially alter the structural characteristics of the original sequence. For example, any substitution is possible as long as the substituted amino acids do not disrupt the helix of the original sequence or do not disrupt any other type of secondary structure characterizing the original sequence.

Conservative substitution is generally introduced by synthesis with a biological system or chemical peptide synthesis, preferably by chemical peptide synthesis. In such a case, substituents may include an unnatural amino acid residue, a peptidomimetic, or a reversed or inverted form where an unsubstituted region is reversed or inverted in the amino acid sequence.

Unlimited examples of the mutually substitutable amino acid residues are classified and listed below:

Group A: leucine, isoleucine, norleucine, valine, norvaline, alanine, 2-aminobutanoic acid, methionine, O-methylserine, t-butylglycine, t-butylalanine, and cyclohexylalanine;

Group B: aspartic acid, glutamic acid, isoaspartic acid, isoglutamic acid, 2-aminoadipic acid, and 2-aminosuberic acid;

Group C: asparagine and glutamine;

Group D: lysine, arginine, ornithine, 2,4-diaminobutanoic acid, and 2,3-diaminopropionic acid;

Group E: proline, 3-hydroxyproline, and 4-hydroxyproline;

Group F: serine, threonine, and homoserine; and

Group G: phenylalanine and tyrosine.

In non-conservative substitution, a member of one of the above groups may be replaced by a member from another group. In such a case, in order to maintain the biological function of the protein of the present invention, the hydropathic indices of amino acids (hydropathic amino acid indices) (Kyte, et al., J. Mol. Biol., 157: 105-131 (1982)) are preferably considered.

In the case of non-conservative substitution, amino acid substitutions may be accomplished on the basis of hydrophilicity.

Note that in either conservative substitution or non-conservative substitution, the amino acid residues corresponding to the 316th, 319th, and 351st amino acids in SEQ ID NO: 2 are desirably glycine, serine, and proline, respectively. In SEQ ID NO: 9, the amino acid residues corresponding to the 430th, 432nd, and 465th amino acids are desirably glycine, serine, and proline, respectively.

Throughout the specification and drawings, nucleotides, amino acids, and abbreviations thereof are those according to the IUPAC-IUB Commission on Biochemical Nomenclature or those conventionally used in the art, for example, as described in Immunology—A Synthesis (second edition, edited by E. S. Golub and D. R. Gren, Sinauer Associates, Sunderland, Mass. (1991)). Moreover, amino acids which may have optical isomers are intended to represent their L-isomers, unless otherwise specified.

Stereoisomers such as D-amino acids of the above-mentioned amino acids, unnatural amino acids such as α,α-disubstituted amino acids, N-alkylamino acids, lactic acid, and other unconventional amino acids can be also members constituting the proteins of the present invention.

Note that in the protein notation used throughout the specification, the left-hand direction is the amino terminal direction and the right-hand direction is the carboxy terminal direction, in accordance with standard usage and convention in the art.

Similarly, in general, unless otherwise specified, the left-hand end of single-stranded polynucleotide sequences is the 5'-end and the left-hand direction of double-stranded polynucleotide sequences is referred to as the 5'-direction.

Those skilled in the art can design and prepare appropriate mutants of the proteins described in the specification using techniques known in the art. For example, they can identify a region in a protein molecule which the region is suitable for changing the structure of the protein of the present invention without impairing the biological activity of the protein by targeting a region which appears to be less important for the biological activity of the protein. Those skilled in the art also can identify a residue or region conserved between similar proteins. Those skilled in the art also can introduce conservative amino acid substitution into a region that appears to be important for the biological activity or structure of the protein of the present invention, without impairing the biological activity and without adversely affecting the polypeptide structure of the protein.

Those skilled in the art can conduct a so-called structure-function study, which identifies residues of a peptide that is similar to a peptide of a protein of the present invention and important for a biological activity or structure of the protein, compares the amino acid residues of these two peptides, and thereby predicts which residue in the protein similar to the protein of the present invention is the amino acid residue corresponding to the important amino acid residue for the biological activity or structure. They also can select a mutant which maintains the biological activity of the protein of the present invention by selecting an amino acid substituent chemically similar to the thus predicted amino acid residue. Further, those skilled in the art can analyze the three-dimensional structure and amino acid sequence of this protein mutant. Furthermore, those skilled in the art can predict an alignment of amino acid residues involved in the three-dimensional structure of the protein based on the analytical results thus obtained. Though amino acid residues predicted to be on the protein surface may be involved in important interaction with other molecules, those skilled in the art would be able to prepare a mutant that causes no change in these amino acid residues predicted to be on the protein surface, on the basis of analytical results as mentioned above. Those skilled in the art can also prepare a mutant having a single amino acid substitution for any of the amino acid residues constituting the protein of the present invention. These mutants may be screened by any known assay to collect information about the individual mutants, which in turn allows evaluation of the usefulness of individual amino acid residues constituting the protein of the present invention by comparison of the case where a mutant having substitution of a specific amino acid residue shows a lower biological activity than that of the protein of the present invention, the case where such a mutant shows no biological activity, or the case where such a mutant produces unsuitable activity that inhibits the biological activity of the protein of the present invention. Moreover, those skilled in the art can readily analyze amino acid substitutions undesirable for mutants of the protein of the present invention based on information collected from such routine experiments alone or in combination with other mutations.

As described above, a protein consisting of an amino acid sequence having deletion, substitution, or addition of one or more amino acids in the amino acid sequence set forth in SEQ ID NO: 2, SEQ ID NO: 5, or SEQ ID NO: 9 can be prepared according to techniques such as site-directed mutagenesis as described in, for example, "Molecular Cloning, A Laboratory Manual 3rd ed." (Cold Spring Harbor Press (2001)); "Current Protocols in Molecular Biology" (John Wiley & Sons (1987-1997); Kunkel, (1985), Proc. Natl. Acad. Sci. USA, 82: 488-92; or Kunkel, (1988), Method Enzymol., 85: 2763-6). Preparation of a mutant with such a mutation including amino acid deletion, substitution, or addition may be accomplished, for example, by known procedures such as a Kunkel method or a Gapped duplex method using a mutation-introducing kit based on site-directed mutagenesis such as a QuikChange™ Site-Directed Mutagenesis Kit (manufactured by Stratagene), a GeneTailor™ Site-Directed Mutagenesis System (manufactured by Invitrogen), or a TaKaRa Site-Directed Mutagenesis System (e.g., Mutan-K, Mutan-Super Express Km; manufactured by Takara Bio Inc.).

Techniques for introducing deletion, substitution, or addition of one or more amino acids in the amino acid sequence of a protein while maintaining its activity include a method of treating a gene with a mutagen and a method selectively cleaving a gene and deleting, substituting, or adding a selected nucleotide and then ligating the gene, in addition to site-directed mutagenesis mentioned above.

The nucleotide sequence contained in the nucleic acid of the present invention is preferably a nucleotide sequence that encodes a protein consisting of an amino acid sequence having deletion, substitution, or addition of 1 to 80 amino acids in the amino acid sequence set forth in SEQ ID NO: 2, SEQ ID NO: 5, or SEQ ID NO: 9 and having a GPAT activity and/or a GNPAT activity.

Examples of the nucleotide sequence contained in the nucleic acid of the present invention also preferably encompass nucleotide sequences that encode a protein consisting of an amino acid sequence having deletion, substitution, or addition of 1 to 80 amino acids in the amino acid sequence set forth in SEQ ID NO: 2, SEQ ID NO: 5, or SEQ ID NO: 9 and having the activity of the present invention.

The number and sites of amino acid mutations or modifications in the protein of the present invention are not limited as long as the activity of the present invention is maintained.

The activity of the present invention, represented by the GPAT activity of the protein, can be measured by a known method, for example, see Biochem. J., 355, 315-322, 2001.

For example, the "GPAT activity" of the present invention may be measured as follows: A microsome fraction is prepared from yeast expressing the GPAT of the present invention by, for example, the method described in J. Bacteriology, 173, 2026-2034 (1991) or the like. The microsome fraction is added to a reaction solution containing 0.44 mM glycerol 3-phosphate, 0.36 mM acyl-CoA, 0.5 mM DTT, 1 mg/ml BSA, 2 mM $MgCl_2$, and 50 mM Tris-HCl (pH 7.5), followed by reaction at 28° C. for an appropriate time. The reaction is terminated by addition of a mixture of chloroform and methanol, and lipids are extracted. The resulting lipids are fractionated by thin layer chromatography or the like to measure the amount of generated lysophosphatidic acid.

The activity of the present invention shown in the i), ii), or v) above may be measured by, for example, determining the proportions or contents of fatty acids in a host cell expressing the protein of the present invention (e.g., yeast, *M. alpina*). A mixture of chloroform and methanol adjusted to an appropriate ratio is added to lyophilized cells prepared by a method of producing a fatty acid composition of the present invention, and the resulting mixture is stirred and then heated for an appropriate time. The cells are separated by centrifugation to recover the solvent. This procedure is repeated several times. Subsequently, lipids are dried in an appropriate manner and are then dissolved in a solvent such as chloroform to prepare a sample. From an appropriate amount of this sample, the fatty acids of the cells are converted into methyl ester by a hydrochloric acid-methanol method and are extracted with hexane. Hexane is distilled off, followed by gas chromatographic analysis.

The activity of the present invention shown in the iii) above may be measured by, for example, determining the amount of triacylglycerol (TG) of yeast expressing the protein of the present invention. The lipids are extracted and collected from cells as described above, and the TG fraction is collected by fractionation, for example, through thin layer chromatography (TLC). The fatty acids constituting TG in the collected TG fraction are converted into methyl ester by the hydrochloric acid-methanol method and are extracted with hexane. Hexane is distilled off, followed by gas chromatographic quantitative determination.

The activity of the present invention shown in the iv) above may be measured by, for example, confirming whether the introduced protein of the present invention can complement the GPAT deficiency of yeast (S. cerevisiae). In yeast, SCT1 and GPT2 are known as genes involved in the GPAT activity, and it is known that simultaneous deficiency in these genes results in death. That is, yeast deficient in both the SCT1 gene and the GPT2 gene usually cannot grow, but can grow in a complementary manner when a gene having a similar function to these genes, i.e., a protein having a GPAT activity, is expressed. Regarding the GPAT of the present invention, the method for confirming complementation for the GPAT deficiency may be any method that confirms the recovery of the GPAT activity of yeast strain deficient in the SCT1 gene and the GPT2 gene by expressing the GPAT gene of the present invention. For example, as specifically described in Example 8 below, in Δgpt2 homozygous diploid yeast, a heterozygous strain in which only one of alleles of the SCT1 gene is deficient is produced. Subsequently, a strain where one expression cassette of the GPAT gene of the present invention is inserted to the heterozygous strain on a chromosome different from the chromosome on which the SCT1 is present or a strain where a plasmid vector having an expression cassette of the GPAT gene of the present invention is inserted to the heterozygous strain is produced. The resulting strain is applied to a spore-forming medium to form ascospores. The resulting cells are subjected to random spore analysis or tetrad analysis to obtain a haploid strain derived from the spores. The genotype of the thus-prepared haploid yeast is inspected. If it is confirmed that the Δgpt2Δsct1 strain, which inherently cannot grow, can grow only when the expression cassette of the GPAT gene of the present invention is present, the GPAT of the present invention can be determined to be able to complement a GPAT activity in the yeast.

(b) A nucleic acid comprising a nucleotide sequence that is hybridizable with a nucleic acid consisting of a nucleotide sequence complementary to the nucleotide sequence set forth in SEQ ID NO: 1, SEQ ID NO: 4, or SEQ ID NO: 8 under stringent conditions and that encodes a protein having the activity of the present invention Examples of the nucleotide sequence contained in the nucleic acid of the present invention encompass nucleotide sequences that are hybridizable with a nucleic acid consisting of a nucleotide sequence complementary to the nucleotide sequence set forth in SEQ ID NO: 1, SEQ ID NO: 4, or SEQ ID NO: 8 under stringent conditions and encodes a protein having the activity of the present invention.

Such a nucleotide sequence can be prepared from, for example, a cDNA library or a genomic library by a known hybridization technique such as colony hybridization, plaque hybridization, or Southern blotting using a probe produced from an appropriate fragment by a method known to those skilled in the art.

Detailed procedure of the hybridization can be referred to "Molecular Cloning, A Laboratory Manual 3rd ed." (Cold Spring Harbor Press (2001), in particular, Sections 6 and 7), "Current Protocols in Molecular Biology" (John Wiley & Sons (1987-1997), in particular, Sections 6.3 and 6.4), and "DNA Cloning 1: Core Techniques, A Practical Approach 2nd ed." (Oxford University (1995), in particular, Section 2.10 for hybridization conditions).

The strength of hybridization conditions is determined primarily based on hybridization conditions, more preferably based on hybridization conditions and washing conditions. The term "stringent conditions" used throughout the specification is intended to include moderately or highly stringent conditions.

Specifically, examples of the moderately stringent conditions include hybridization conditions of 1×SSC to 6×SSC at 42° C. to 55° C., more preferably 1×SSC to 3×SSC at 45° C. to 50° C., and most preferably 2×SSC at 50° C. In the case of a hybridization solution containing, for example, about 50% formamide, a hybridization temperature of lower than the temperature mentioned above by 5° C. to 15° C. is employed. Washing conditions are, for example, 0.5×SSC to 6×SSC at 40° C. to 60° C. To the hybridization solution and washing solution, 0.05% to 0.2% SDS, preferably about 0.1% SDS, may be usually added.

Highly stringent (high stringent) conditions include hybridization and/or washing at higher temperature and/or lower salt concentration, compared to the moderately stringent conditions. Examples of the hybridization conditions include 0.1×SSC to 2×SSC at 55° C. to 65° C., more preferably 0.1×SSC to 1×SSC at 60° C. to 65° C., and most preferably 0.2×SSC at 63° C. Washing conditions are, for example, 0.2×SSC to 2×SSC at 50° C. to 68° C., and more preferably 0.2×SSC at 60° C. to 65° C.

Examples of the hybridization conditions particularly used in the present invention include, but not limited to, prehybridization in 5×SSC, 1% SDS, 50 mM Tris-HCl (pH 7.5) and 50% formamide at 42° C., overnight incubation at 42° C. in the presence of a probe to form hybrids, and washing in 0.2×SSC, 0.1% SDS at 65° C. for 20 minutes three times.

It is also possible to use a commercially available hybridization kit not using radioactive substance as a probe. Specifically, for example, a DIG nucleic acid detection kit (Roche Diagnostics) or an ECL direct labeling & detection system (manufactured by Amersham) is used for hybridization.

Preferred examples of the nucleotide sequence falling within the present invention include nucleotide sequences that are hybridizable with a nucleic acid consisting of a nucleotide sequence complementary to the nucleotide sequence set forth in SEQ ID NO: 1, SEQ ID NO: 4, or SEQ ID NO: 8 under conditions of 2×SSC at 50° C. and encode a protein having a GPAT activity and/or a GNPAT activity.

(c) A nucleic acid comprising a nucleotide sequence that consists of a nucleotide sequence having an identity of 70% or more with the nucleotide sequence set forth in SEQ ID NO: 1, SEQ ID NO: 4, or SEQ ID NO: 8 and encodes a protein having the activity of the present invention Examples of the nucleotide sequence contained in the nucleic acid of the present invention encompass nucleotide sequences that have an identity of at least 70% with the nucleotide sequence set forth in SEQ ID NO: 1, SEQ ID NO: 4, or SEQ ID NO: 8 and encode a protein having the activity of the present invention.

Preferably, for example, a nucleic acid comprises a nucleotide sequence having an identity of at least 75%, more preferably 80% or more (e.g., 85% or more, more preferably 90% or more, and most preferably 95%, 98%, or 99% or more) with the nucleotide sequence set forth in SEQ ID NO: 1, SEQ ID NO: 4, or SEQ ID NO: 8 and encoding a protein having the activity of the present invention.

The percent identity between two nucleotide sequences can be determined by visual inspection and mathematical calculation, but is preferably determined by comparing sequence information of two nucleic acids using a computer program. As computer programs for sequence comparison, for example, the BLASTN program (Altschul et al., (1990), J. Mol. Biol., 215: 403-10) version 2.2.7, available via the National Library of Medicine website: www.ncbi.nlm.nih.gov/blast/bl2seq/bls.html or the WU-BLAST 2.0 algorithm can be used. Standard default parameter settings for WU-BLAST 2.0 are described at the following Internet site: blast.wustl.edu.

(d) A nucleic acid comprising a nucleotide sequence encoding an amino acid sequence having an identity of 70% or more with the amino acid sequence set forth in SEQ ID NO: 2, SEQ ID NO: 5, or SEQ ID NO: 9 and encoding a protein having the activity of the present invention Examples of the nucleotide sequence contained in the nucleic acid of the present invention encompass nucleotide sequences encoding an amino acid sequence having an identity of 70% or more with the amino acid sequence set forth in SEQ ID NO: 2, SEQ ID NO: 5, or SEQ ID NO: 9 and encoding a protein having the activity of the present invention. The protein encoded by the nucleic acid of the present invention may be any protein having an identity with the amino acid sequence of MaGPAT4, MaGPAT4-long, or MaGPAT5 as long as the protein is functionally equivalent to the protein having the activity of the present invention.

Specific examples of the protein include amino acid sequences having an identity of 75% or more, preferably 80% or more, more preferably 85% or more, and most preferably 90% or more (e.g., 95% or more, furthermore 98% or more) with the amino acid sequence set forth in SEQ ID NO: 2, SEQ ID NO: 5, or SEQ ID NO: 9.

The nucleotide sequence contained in the nucleic acid of the present invention is preferably a nucleotide sequence encoding an amino acid sequence having an identity of 90% or more with the amino acid sequence set forth in SEQ ID NO: 2, SEQ ID NO: 5, or SEQ ID NO: 9 and encoding a protein having the activity of the present invention. More preferably, a nucleotide sequence encoding an amino acid sequence having an identity of 95% or more with the amino acid sequence set forth in SEQ ID NO: 2, SEQ ID NO: 5, or SEQ ID NO: 9 and encoding a protein having the activity of the present invention.

The percent identity between two amino acid sequences can be determined by visual inspection and mathematical calculation or can be determined using a computer program. Examples of such a computer program include BLAST, FASTA (Altschul et al., J. Mol. Biol., 215: 403-410, (1990)) and ClustalW. In particular, various conditions (parameters) for an identity search with the BLAST program are described by Altschul et al. (Nucl. Acids. Res., 25, pp. 3389-3402, 1997) and publicly available via the website of the National Center for Biotechnology Information (NCBI) of USA or the DNA Data Bank of Japan (DDBJ) (BLAST Manual, Altschul et al., NCB/NLM/NIH Bethesda, Md. 20894; Altschul et al.). It is also possible to use a program such as genetic information processing software GENETYX Ver. 7 (Genetyx Corporation), DINASIS Pro (Hitachisoft), or Vector NTI (Infomax) for determination of the percent identity.

A specific alignment scheme for aligning a plurality of amino acid sequences can show matching of sequences also in a specific short region and can therefore detect a region having a very high sequence identity in such a short region even if the full-length sequences have no significant relationship therebetween. In addition, the BLAST algorithm can use the BLOSUM62 amino acid scoring matrix, and the following selection parameters can be used: (A) inclusion of filters to mask a segment of a query sequence having low compositional complexity (as determined by the SEG program of Wootton and Federhen (Computers and Chemistry, 1993); also see Wootton and Federhen, 1996, "Analysis of compositionally biased regions in sequence databases", Methods Enzymol., 266: 554-71) or to mask segments consisting of short-periodicity internal repeats (as determined by the XNU program of Clayerie and States (Computers and Chemistry, 1993), and (B) a statistical significance threshold for reporting matches against database sequences, or the expected probability of matches being found merely by chance, according to the statistical model of E-score (Karlin and Altschul, 1990); if the statistical significance ascribed to a match is greater than this E-score threshold, the match will not be reported.

(e) A nucleic acid comprising a nucleotide sequence that is hybridizable with a nucleic acid consisting of a nucleotide sequence complementary to a nucleotide sequence encoding a protein consisting of the amino acid sequence set forth in SEQ ID NO: 2, SEQ ID NO: 5, or SEQ ID NO: 9 under stringent conditions and encodes a protein having an activity of the present invention Examples of the nucleotide sequence contained in the nucleic acid of the present invention encompass nucleotide sequences that are hybridizable with a nucleic acid consisting of a nucleotide sequence complementary to a nucleotide sequence encoding a protein consisting of the amino acid sequence set forth in SEQ ID NO: 2, SEQ ID NO: 5, or SEQ ID NO: 9 under stringent conditions and encode a protein having an activity of the present invention.

The protein consisting of the amino acid sequence set forth in SEQ ID NO: 2, SEQ ID NO: 5, or SEQ ID NO: 9 and the hybridization conditions are as described above. Examples of the nucleotide sequence contained in the nucleic acid of the present invention include nucleotide sequences that are hybridizable with a nucleic acid consisting of a nucleotide sequence complementary to a nucleotide sequence encoding a protein consisting of the amino acid sequence set forth in SEQ ID NO: 2, SEQ ID NO: 5, or SEQ ID NO: 9 under stringent conditions and encode a protein having the activity of the present invention.

(f) A nucleic acid comprising a nucleotide sequence that is hybridizable with a nucleic acid consisting of a nucleotide sequence complementary to the nucleotide sequence set forth in SEQ ID NO: 7 or SEQ ID NO: 12 under stringent conditions and includes an exon encoding a protein having the activity of the present invention The nucleotide sequences set forth in SEQ ID NO: 7 and SEQ ID NO: 12 are the genomic DNA sequences encoding MaGPAT4 (and MaGPAT4-long) and MaGPAT5, respectively, of the present invention.

Examples of the nucleotide sequence contained in the nucleic acid of the present invention encompass nucleotide sequences that are hybridizable with a nucleic acid consisting of a nucleotide sequence complementary to the nucleotide sequence set forth in SEQ ID NO: 7 or SEQ ID NO: 12 under stringent conditions and include an exon encoding a protein having the activity of the present invention.

Such a nucleotide sequence can be prepared by a method known to those skilled in the art from, for example, a genomic library by a known hybridization technique such as colony hybridization, plaque hybridization, or Southern blotting using a probe produced using an appropriate fragment. The hybridization conditions are as described above.

(g) A nucleic acid comprising a nucleotide sequence that consists of a nucleotide sequence having an identity of 70% or more with the nucleotide sequence set forth in SEQ ID NO: 7 or SEQ ID NO: 12 and includes an exon encoding a protein having the activity of the present invention Examples of the nucleotide sequence contained in the nucleic acid of the present invention encompass nucleotide sequences that have an identity of at least 70% with the nucleotide sequence set forth in SEQ ID NO: 7 or SEQ ID NO: 12 and encode a protein having the activity of the present invention. Preferred examples of the nucleotide sequence include those having an identity of at least 75%, more preferably 80% or more (e.g., 85% or more, more preferably 90% or more, and most preferably 95%, 98%, or 99% or more) with the nucleotide sequence set forth in SEQ ID NO: 7 or SEQ ID NO: 12 and having an exon encoding a protein having the activity of the present invention. The percent identity between two nucleotide sequences can be determined as described above.

The genomic DNA sequence set forth in SEQ ID NO: 7 is composed of ten exons and nine introns. In SEQ ID NO: 7, the exon regions correspond to nucleotides 428 to 744 or 596 to 744, 850 to 924, 1302 to 1396, 1480 to 1726, 1854 to 2279, 2370 to 2632, 2724 to 3299, 3390 to 3471, 3575 to 4024, and 4133 to 4248. The genomic DNA sequence set forth in SEQ ID NO: 12 is composed of three exons and two introns. In SEQ ID NO: 12, the exon regions correspond to nucleotides 1 to 302, 457 to 1676, and 1754 to 2598.

In another embodiment, examples of the nucleotide sequence contained in the nucleic acid of the present invention include nucleotide sequences including intron regions having a nucleotide sequence identity of 100% with the genomic DNA sequence set forth in SEQ ID NO: 7 or SEQ ID NO: 12 and exon regions having a nucleotide sequence identity of at least 70% or more, more preferably. 75% or more, and more preferably 80% or more (e.g., 85% or more, more preferably 90% or more, and most preferably 95%, 98%, or 99% or more) with the sequence set forth in SEQ ID NO: 7 or SEQ ID NO: 12, wherein the exon encodes a protein having the activity of the present invention.

In another embodiment, examples of the nucleotide sequence contained in the nucleic acid of the present invention include nucleotide sequences including exon regions having a nucleotide sequence identity of 100% with the genomic DNA sequence set forth in SEQ ID NO: 7 or SEQ ID NO: 12 and intron regions having a nucleotide sequence identity of at least 70% or more, more preferably 75% or more, and more preferably 80% or more (e.g., 85% or more, more preferably 90% or more, and most preferably 95%, 98%, or 99% or more) with the sequence set forth in SEQ ID NO: 7 or SEQ ID NO: 12, wherein the intron regions can be eliminated by splicing, and thereby the exon regions are ligated to encode a protein having the activity of the present invention.

In another embodiment, examples of the nucleotide sequence contained in the nucleic acid of the present invention include nucleotide sequences including intron regions having a nucleotide sequence identity of at least 70% or more, more preferably 75% or more, and more preferably 80% or more (e.g., 85% or more, more preferably 90% or more, and most preferably 95%, 98%, or 99% or more) with the genomic DNA sequence set forth in SEQ ID NO: 7 or SEQ ID NO: 12 and exon regions having a nucleotide sequence identity of at least 70% or more, more preferably 75% or more, and more preferably 80% or more (e.g., 85% or more, more preferably 90% or more, and most preferably 95%, 98% or more, or 99% or more) with the sequence set forth in SEQ ID NO: 7 or SEQ ID NO: 12, wherein the intron regions can be eliminated by splicing, and thereby the exon regions are ligated to encode a protein having the activity of the present invention.

The percent identity between two nucleotide sequences can be determined by the method described above.

Examples of the nucleic acid of the present invention encompass nucleic acids each consisting of a nucleotide sequence having deletion, substitution, or addition of one or more nucleotides in the nucleotide sequence set forth in SEQ ID NO: 1, SEQ ID NO: 4, or SEQ ID NO: 8 and encoding a protein having the activity of the present invention. More specifically, a usable nucleic acid includes any one of the following nucleotide sequences:

(i) a nucleotide sequence having deletion of one or more (preferably one to several (e.g., 1 to 720, 1 to 600, 1 to 500, 1 to 400, 1 to 300, 1 to 250, 1 to 200, 1 to 150, 1 to 100, 1 to 50, 1 to 30, 1 to 25, 1 to 20, or 1 to 15, more preferably, 10, 9, 8, 7, 6, 5, 4, 3, 2, or 1)) nucleotides in the nucleotide sequence set forth in SEQ ID NO: 1, SEQ ID NO: 4, or SEQ ID NO: 8;

(ii) a nucleotide sequence having substitution of one or more (preferably one to several (e.g., 1 to 720, 1 to 600, 1 to 500, 1 to 400, 1 to 300, 1 to 250, 1 to 200, 1 to 150, 1 to 100, 1 to 50, 1 to 30, 1 to 25, 1 to 20, or 1 to 15, more preferably, 10, 9, 8, 7, 6, 5, 4, 3, 2, or 1)) nucleotides in the nucleotide sequence set forth in SEQ ID NO: 1, SEQ ID NO: 4, or SEQ ID NO: 8;

(iii) a nucleotide sequence having addition of one or more (preferably one to several (e.g., 1 to 720, 1 to 600, 1 to 500, 1 to 400, 1 to 300, 1 to 250, 1 to 200, 1 to 150, 1 to 100, 1 to 50, 1 to 30, 1 to 25, 1 to 20, or 1 to 15, more preferably, 10, 9, 8, 7, 6, 5, 4, 3, 2, or 1)) nucleotides in the nucleotide sequence set forth in SEQ ID NO: 1, SEQ ID NO: 4, or SEQ ID NO: 8; and (iv) a nucleotide sequence with any combination of (i) to (iii) above, wherein the nucleotide sequence encodes a protein having the activity of the present invention.

A preferred embodiment of the nucleic acid of the present invention also encompasses nucleic acids comprising a fragment of a nucleotide sequence shown in any one of (a) to (d) below:

(a) the nucleotide sequence set forth in SEQ ID NO: 1, SEQ ID NO: 4, or SEQ ID NO: 8;

(b) a nucleotide sequence encoding a protein consisting of the amino acid sequence set forth in SEQ ID NO: 2, SEQ ID NO: 5, or SEQ ID NO: 9;

(c) the nucleotide sequence set forth in SEQ ID NO: 3, SEQ ID NO: 6, or SEQ ID NO: 11; and (d) the nucleotide sequence set forth in SEQ ID NO: 7 or SEQ ID NO: 12.

(A) the nucleotide sequence set forth in SEQ ID NO: 1, SEQ ID NO: 4, or SEQ ID NO: 8, (b) the nucleotide sequence encoding a protein consisting of the amino acid sequence set forth in SEQ ID NO: 2, SEQ ID NO: 5, or SEQ ID NO: 9, and (c) the nucleotide sequence set forth in SEQ ID NO: 3, SEQ ID NO: 6, or SEQ ID NO: 11 are as shown in Table 1. The nucleotide sequence set forth in SEQ ID NO: 7 or SEQ ID NO: 12 is also as described above. The fragments of these sequences include ORF, CDS, a biologically active region, a region used as a primer as described later, or a region which may serve as a probe contained in these nucleotide sequences, and may be either naturally occurring or artificially prepared.

Examples of the nucleic acid of the present invention encompass the following nucleic acids.

(1) Nucleic acids shown in any one of (a) to (g) below:

(a) nucleic acids comprising a nucleotide sequence encoding a protein consisting of an amino acid sequence having deletion, substitution, or addition of one or more amino acids in the amino acid sequence set forth in SEQ ID NO: 2, SEQ ID NO: 5, or SEQ ID NO: 9;

(b) nucleic acids hybridizable with a nucleic acid consisting of a nucleotide sequence complementary to the nucleotide sequence set forth in SEQ ID NO: 1, SEQ ID NO: 4, or SEQ ID NO: 8 under stringent conditions;

(c) nucleic acids comprising a nucleotide sequence having an identity of 70% or more with the nucleotide sequence set forth in SEQ ID NO: 1, SEQ ID NO: 4, or SEQ ID NO: 8;

(d) nucleic acids comprising a nucleotide sequence encoding a protein consisting of an amino acid sequence having an identity of 70% or more with the amino acid sequence set forth in SEQ ID NO: 2, SEQ ID NO: 5, or SEQ ID NO: 9;

(e) nucleic acids hybridizable with a nucleic acid consisting of a nucleotide sequence complementary to a nucleotide sequence encoding a protein consisting of the amino acid sequence set forth in SEQ ID NO: 2, SEQ ID NO: 5, or SEQ ID NO: 9 under stringent conditions;

(f) nucleic acids hybridizable with a nucleic acid consisting of a nucleotide sequence complementary to the nucleotide sequence set forth in SEQ ID NO: 7 or SEQ ID NO: 12 under stringent conditions; and (g) nucleic acids comprising a nucleotide sequence having an identity of 70% or more with the nucleotide sequence set forth in SEQ ID NO: 7 or SEQ ID NO: 12.

(2) Nucleic acids described in (1) above, shown in any one of (a) to (g) below:

(a) nucleic acids comprising a nucleotide sequence encoding a protein consisting of an amino acid sequence having deletion, substitution, or addition of 1 to 80 amino acids in the amino acid sequence set forth in SEQ ID NO: 2, SEQ ID NO: 5, or SEQ ID NO: 9;

(b) nucleic acids hybridizable with a nucleic acid consisting of a nucleotide sequence complementary to the nucleotide sequence set forth in SEQ ID NO: 1, SEQ ID NO: 4, or SEQ ID NO: 8 under conditions of 2×SSC at 50° C.;

(c) nucleic acids comprising a nucleotide sequence having an identity of 90% or more with the nucleotide sequence set forth in SEQ ID NO: 1, SEQ ID NO: 4, or SEQ ID NO: 8;

(d) nucleic acids comprising a nucleotide sequence encoding a protein consisting of an amino acid sequence having an identity of 90% or more with the amino acid sequence set forth in SEQ ID NO: 2, SEQ ID NO: 5, or SEQ ID NO: 9;

(e) nucleic acids hybridizable with a nucleic acid consisting of a nucleotide sequence complementary to a nucleotide sequence encoding a protein consisting of the amino acid sequence set forth in SEQ ID NO: 2, SEQ ID NO: 5, or SEQ ID NO: 9 under conditions of 2×SSC at 50° C.;

(f) nucleic acids hybridizable with a nucleic acid consisting of a nucleotide sequence complementary to the nucleotide sequence set forth in SEQ ID NO: 7 or SEQ ID NO: 12 under conditions of 2×SSC at 50° C.; and (g) nucleic acids comprising a nucleotide sequence having an identity of 90% or more with the nucleotide sequence set forth in SEQ ID NO: 7 or SEQ ID NO: 12.

Glycerol 3-phosphate acyltransferase of the Present Invention

Examples of the protein of the present invention encompass a protein consisting of the amino acid sequence set forth in SEQ ID NO: 2, SEQ ID NO: 5, or SEQ ID NO: 9 and proteins functionally equivalent to such a protein. These proteins may be either naturally occurring or artificially prepared. The protein consisting of the amino acid sequence set forth in SEQ ID NO: 2, SEQ ID NO: 5, or SEQ ID NO: 9 is as described above. The "proteins functionally equivalent" refers to proteins having "the activity of the present invention" described in the "Nucleic acid encoding glycerol 3-phosphate acyltransferase of the present invention" above.

In the present invention, examples of the proteins functionally equivalent to a protein consisting of the amino acid sequence set forth in SEQ ID NO: 2, SEQ ID NO: 5, or SEQ ID NO: 9 include proteins according to any one of (a) and (b) below:

(a) a protein consisting of an amino acid sequence having deletion, substitution, or addition of one or more amino acids in the amino acid sequence set forth in SEQ ID NO: 2, SEQ ID NO: 5, or SEQ ID NO: 9 and having the activity of the present invention; and (b) a protein consisting of an amino acid sequence having an identity of 70% or more with the amino acid sequence set forth in SEQ ID NO: 2, SEQ ID NO: 5, or SEQ ID NO: 9 and having the activity of the present invention.

In the above, the amino acid sequence having deletion, substitution, or addition of one or more amino acids in the amino acid sequence set forth in SEQ ID NO: 2, SEQ ID NO: 5, or SEQ ID NO: 9 or the amino acid sequence having an identity of 70% or more with the amino acid sequence set forth in SEQ ID NO: 2, SEQ ID NO: 5, or SEQ ID NO: 9 are as described in the "Nucleic acid encoding glycerol 3-phosphate acyltransferase of the present invention" above. The "protein having the activity of the present invention" encompasses mutants of proteins encoded by a nucleic acid comprising the nucleotide sequence set forth in SEQ ID NO: 1, SEQ ID NO: 4, or SEQ ID NO: 8; mutated proteins by many types of modification such as deletion, substitution, and addition of one or more amino acids in the amino acid sequence set forth in SEQ ID NO: 2, SEQ ID NO: 5, or SEQ ID NO: 9; modified proteins having, for example, modified amino acid side chains; and fused proteins with other proteins, where these proteins have the GPAT activity, the GNPAT activity, and/or the activity i) or the activity ii) described in the "Nucleic acid encoding glycerol 3-phosphate acyltransferase of the present invention" above.

The protein of the present invention may be artificially prepared. In such a case, the protein can be produced by chemical synthesis such as a Fmoc method (fluorenylmethyloxycarbonyl method) or a tBoc method (t-butyloxycarbonyl method). In addition, peptide synthesizers available from Advanced ChemTech, Perkin Elmer, Pharmacia, Protein Technology Instrument, Synthecell-Vega, PerSeptive, Shimadzu Corporation, or other manufacturers may be used for chemical synthesis.

Examples of the protein of the present invention further encompass the following proteins.

(1) Proteins according to any one of (a) and (b) below:

(a) proteins consisting of an amino acid sequence having deletion, substitution, or addition of one or more amino acids in the amino acid sequence set forth in SEQ ID NO: 2, SEQ ID NO: 5, or SEQ ID NO: 9; and (b) proteins consisting of an amino acid sequence having an identity of 70% or more with the amino acid sequence set forth in SEQ ID NO: 2, SEQ ID NO: 5, or SEQ ID NO: 9.

(2) Proteins described in (1) above, shown in any one of (a) and (b) below:

(a) proteins consisting of an amino acid sequence having deletion, substitution, or addition of 1 to 80 amino acids in the amino acid sequence set forth in SEQ ID NO: 2, SEQ ID NO: 5, or SEQ ID NO: 9; and (b) proteins consisting of an amino acid sequence having an identity of 90% or more with the amino acid sequence set forth in SEQ ID NO: 2, SEQ ID NO: 5, or SEQ ID NO: 9.

Cloning of Nucleic Acid of the Present Invention

The GPAT nucleic acid of the present invention can be cloned by, for example, screening from a cDNA library using an appropriate probe. The cloning can be performed by PCR amplification using appropriate primers and subsequent ligation to an appropriate vector. The cloned nucleic acid may be further subcloned into another vector.

Commercially available plasmid vectors, such as pBlueScript™ SK(+) (Stratagene), pGEM-T (Promega), pAmp (TM: Gibco-BRL), p-Direct (Clontech), or pCR2.1-TOPO (Invitrogen), can be used. In PCR amplification, a primer may be any region of, e.g., the nucleotide sequence set forth in SEQ ID NO: 3, 6, or 11. For example, primers described in Examples shown below can be used. Then, PCR is performed using cDNA prepared from *M. alpina* cells with the primers above, DNA polymerase, and any other substance. Although this procedure can be readily performed by those skilled in the art according to, e.g., "Molecular Cloning, A Laboratory Manual 3rd ed." (Cold Spring Harbor Press (2001)), PCR conditions in the present invention may be, for example, as follows:

Denaturation temperature: 90° C. to 95° C.,
Annealing temperature: 40° C. to 60° C.,
Elongation temperature: 60° C. to 75° C., and
Number of cycles: 10 or more cycles.

The resulting PCR product can be purified by a known method, for example, using a kit such as GENECLEAN kit (Funakoshi Co., Ltd.), QIAquick PCR purification (QIAGEN), or ExoSAP-IT (GE Healthcare Bio-Sciences); a DEAE-cellulose filter; or a dialysis tube. In the case of using an agarose gel, the PCR product is subjected to agarose gel electrophoresis, and nucleotide sequence fragments are cut out from the agarose gel and are purified, for example, with a GENECLEAN kit (Funakoshi Co., Ltd.) or a QIAquick Gel extraction kit (QIAGEN) or by a freeze-squeeze method.

The nucleotide sequence of the cloned nucleic acid can be determined with a nucleotide sequencer.

Vector Construction for GPAT Expression and Preparation of Transformant

The present invention also provides a recombinant vector containing a nucleic acid encoding the GPAT of the present invention. The present invention further provides a transformant transformed with such a recombinant vector.

The recombinant vector and transformant can be prepared as follows: A plasmid having a nucleic acid encoding the GPAT of the present invention is digested with a restriction enzyme. Examples of the restriction enzyme include, but not limited to, EcoRI, KpnI, BamHI, and SalI. The end may be blunted with T4 polymerase. A digested DNA fragment is purified by agarose gel electrophoresis. This DNA fragment is incorporated into an expression vector by a known method in order to prepare a vector for GPAT expression. This expression vector is introduced into a host to prepare a transformant, which is provided for expression of a desired protein.

In this case, the expression vector and the host may be any types that allow expression of a desired protein. Examples of the host include fungi, bacteria, plants, animals, and cells thereof. Examples of fungi include filamentous fungi such as lipid-producing *M. alpina* and yeast strains such as *Saccharomyces cerevisiae*. Examples of bacteria include *Escherichia coli* and *Bacillus subtilis*. Examples of plants include oil plants such as rapeseed, soybean, cotton, safflower, and flax.

As lipid-producing microorganisms, for example, strains described in MYCOTAXON, Vol. XLIV, NO. 2, pp. 257-265 (1992) can be used, and specific examples thereof include microorganisms belonging to the genus *Mortierella* such as microorganisms belonging to subgenus *Mortierella*, e.g., *Mortierella elongata* IFO8570, *Mortierella exigua* IFO8571, *Mortierella hygrophila* IFO5941, *Mortierella alpina* IFO8568, ATCC16266, ATCC32221, ATCC42430, CBS219.35, CBS224.37, CBS250.53, CBS343.66, CBS527.72, CBS528.72, CBS529.72, CBS608.70, and CBS754.68; and microorganisms belonging to subgenus *Micromucor*, e.g., *Mortierella isabellina* CBS194.28, IFO6336, IFO7824, IFO7873, IFO7874, IFO8286, IFO8308, IFO7884, *Mortierella nana* IFO8190, *Mortierella ramanniana* IFO5426, IFO8186, CBS112.08, CBS212.72, IFO7825, IFO8184, WO8185, IFO8287, and *Mortierella vinacea* CBS236.82. In particular, *Mortierella alpina* is preferred.

When a fungus is used as a host, the nucleic acid of the present invention is preferably self-replicable in the host or preferably has a structure insertable onto the fungal chromosome. Preferably, the nucleic acid also includes a promoter and a terminator. When *M. alpina* is used as a host, for example, pD4, pDuraSC, or pDura5 can be used as the expression vector. Any promoter that allows expression in the host can be used, and examples thereof include promoters derived from *M. alpina*, such as histonH4.1 gene promoter, GAPDH (glyceraldehyde 3-phosphate dehydrogenase) gene promoter, and TEF (translation elongation factor) gene promoter.

Examples of the method introducing a recombinant vector into filamentous fungi such as *M. alpina* include electroporation, a spheroplast method, a particle delivery method, and direct microinjection of DNA into nuclei. In the case of using an auxotrophic host strain, the transformed strain can be obtained by selecting a strain that grows on a selective medium lacking a certain nutrient(s). Alternatively, in transformation of using a drug resistant-marker gene, a colony of drug-resistant cells can be obtained by culturing the host cells in a selective medium containing the drug.

When yeast is used as a host, for example, pYE22m can be used as the expression vector. Alternatively, commercially available yeast expression vectors such as pYES (Invitrogen) or pESC (Stratagene) may be used. Examples of the host suitable for the present invention include, but not limited to, *Saccharomyces cerevisiae* strain EH13-15 (trp1, MATa). The promoter that can be used is, for example, a promoter derived from yeast, such as GAPDH promoter, gall promoter, or gal10 promoter.

Examples of the method introducing a recombinant vector into yeast include a lithium acetate method, electroporation, a spheroplast method, dextran-mediated transfection, calcium phosphate precipitation, polybrene-mediated transfection, protoplast fusion, encapsulation of polynucleotide(s) in liposomes, and direct microinjection of DNA into nuclei.

When a bacterium such as *E. coli* is used as a host, for example, pGEX or pUC18 available from Pharmacia can be used as the expression vector. The promoter that can be used includes those derived from, for example, *E. coli* or phage, such as trp promoter, lac promoter, PL promoter, and PR promoter. Examples of the method of introducing a recombinant vector into bacteria include electroporation and calcium chloride methods.

Method of Preparing Fatty Acid Composition of the Present Invention

The present invention provides a method of preparing a fatty acid composition from the transformant described above, i.e., a method of preparing a fatty acid composition from a cultured product obtained by culturing the transformant. The fatty acid composition contains an assembly of one or more fatty acids therein. The fatty acids may be free fatty acids or may be present in the form of lipids containing fatty acids, such as triglyceride or phospholipid. Specifically, the fatty acid composition of the present invention can be prepared by the following method. Alternatively, the fatty acid composition can also be prepared by any other known method.

The medium used for culturing an organism expressing GPAT may be any culture solution (medium) that has an appropriate pH and osmotic pressure and contains biomaterials such as nutrients necessary for growth of each host, trace elements, serum, and antibiotics. For example, in the case of expressing GPAT by transforming yeast, unlimited examples of the medium include SC-Trp medium, YPD medium, and YPD5 medium. The composition of a specific medium, for example, SC-Trp medium, is as follows: One liter of the medium includes 6.7 g of yeast nitrogen base w/o amino acids (DIFCO), 20 g of glucose, and 1.3 g of amino acid powder (a mixture of 1.25 g of adenine sulfate, 0.6 g of arginine, 3 g of aspartic acid, 3 g of glutamic acid, 0.6 g of histidine, 1.8 g of leucine, 0.9 g of lysine, 0.6 g of methionine, 1.5 g of phenylalanine, 11.25 g of serine, 0.9 g of tyrosine, 4.5 g of valine, 6 g of threonine, and 0.6 g of uracil).

Any culture conditions which are suitable for host growth and adequate for stably maintaining the generated enzyme may be employed. Specifically, individual conditions including anaerobic degree, culture period, temperature, humidity, and static culture or shake culture can be adjusted. Culture may be accomplished under the same conditions (one-step culture) or by so-called two-step or three-step culture using two or more different culture conditions. For large-scale culture, two- or more-step culture is preferred because of its high culture efficiency.

In two-step culture using yeast as the host, the fatty acid composition of the present invention can be prepared as follows: As pre-culture, a colony of a transformant is inoculated in, for example, the SC-Trp medium and shake-cultured at 30° C. for 2 days. Subsequently, as main culture, 500 μL of the pre-culture solution is added to 10 mL of YPD5 (2% yeast extract, 1% polypeptone, and 5% glucose) medium, followed by shake culture at 30° C. for 2 days.

Fatty Acid Composition of the Present Invention

The present invention also provides a fatty acid composition as an assembly of one or more fatty acids in cells expressing the GPAT of the present invention, preferably, a fatty acid composition obtained by culturing a transformant expressing the GPAT of the present invention. The fatty acids may be free fatty acids or may be present in the form of lipids containing fatty acids, such as triglyceride or phospholipid.

The fatty acids contained in the fatty acid composition of the present invention are linear or branched monocarboxylic acids of long-chain carbohydrates, and examples thereof include, but not limited to, myristic acid (tetradecanoic acid) (14:0), myristoleic acid (tetradecenoic acid) (14:1), palmitic acid (hexadecanoic acid) (16:0), palmitoleic acid (9-hexadecenoic acid) (16:1), stearic acid (octadecanoic acid) (18:0), oleic acid (cis-9-octadecenoic acid) (18:1(9)), vaccenic acid (11-octadecenoic acid) (18:1(11)), linolic acid (cis,cis-9,12 octadecadienoic acid) (18:2(9,12)), α-linolenic acid (9,12,15-octadecatrienoic acid) (18:3(9,12,15)), γ-linolenic acid (6,9,12-octadecatrienoic acid) (18:3(6,9,12)), stearidonic acid (6,9,12,15-octadecatetraenoic acid) (18:4(6,9,12,15)), arachidic acid (icosanoic acid) (20:0), (8,11-icosadienoic acid) (20:2(8,11)), mead acid (5,8,11-icosatrienoic acid) (20:3(5,8,11)), dihomo γ-linolenic acid (8,11,14-icosatrienoic acid) (20:3(8,11,14)), arachidonic acid (5,8,11,14-icosatetraenoic acid) (20:4(5,8,11,14)), eicosatetraenoic acid (8,11,14,17-icosatetraenoic acid) (20:4(8,11,14,17)), eicosapentaenoic acid (5,8,11,14,17-icosapentaenoic acid) (20:5(5,8,11,14,17)), behenic acid (docosanoic acid) (22:0), (7,10,13,16-docosatetraenoic acid) (22:4(7,10,13,16)), (7,10,13,16,19-docosapentaenoic acid) (22:5(7,10,13,16,19)), (4,7,10,13,16-docosapentaenoic acid) (22:5(4,7,10,13,16)), (4,7,10,13,16,19-docosahexaenoic acid) (22:6(4,7,10,13,16,19)), lignoceric acid (tetradocosanoic acid) (24:0), nervonic acid (cis-15-tetradocosanoic acid) (24:1), and cerotic acid (hexadocosanoic acid) (26:0). Note that the substance names are common names defined by the IUPAC Biochemical Nomenclature, and their systematic names are given in parentheses along with numerics denoting the number of carbons and the positions of double bonds.

The fatty acid composition of the present invention may be composed of any number and any type of fatty acids, as long as it is a combination of one or more fatty acids selected from the fatty acids mentioned above.

The proportions of fatty acids in the fatty acid composition of the present invention can be determined by the method of determining the compositional ratio or the contents of fatty acids described in the "Nucleic acid encoding glycerol 3-phosphate acyltransferase of the present invention" in the specification.

Food or Other Products Comprising Fatty Acid Composition of the Present Invention The present invention also provides a food product comprising the fatty acid composition described above. The fatty acid composition of the present invention can be used for, for example, production of food products containing fats and oils and production of industrial raw materials (for example, raw materials for cosmetics, pharmaceuticals (e.g., external applications for the skin), and soaps), in usual methods. Cosmetics (cosmetic compositions) or pharmaceuticals (pharmaceutical compositions) may be formulated into any dosage form including, but not limited to, solutions, pastes, gels, solids, and powders. Examples of the forms of food products include pharmaceutical formulations such as capsules; natural liquid diets, semi-digested nutritious diets, and elemental nutritious diets where the fatty acid composition of the present invention is blended with proteins, sugars, fats, trace elements, vitamins, emulsifiers, and flavorings; and processed forms such as drinkable preparations and enteral nutrients.

Moreover, examples of the food product of the present invention include, but not limited to, nutritional supplements, health food, functional food, children's food, modified milk for infants, modified milk for premature infant, and geriatric food. Throughout the specification, the term "food" is used as a collective term for edible materials in the form of a solid, a fluid, a liquid, or a mixture thereof.

The term "nutritional supplements" refers to food products enriched with specific nutritional ingredients. The term "health food" refers to food products that are healthful or good for health and encompasses nutritional supplements, natural food, and diet food. The term "functional food" refers to food products for supplying nutritional ingredients that assist body control functions and is synonymous with food for specified health use. The term "children's food" refers to food products given to children up to about 6 years old. The term "geriatric food" refers to food products treated to facilitate digestion and absorption thereof, compared to untreated food. The term "modified milk for infants" refers to modified milk given to children up to about one year old. The term "modified milk for premature infants" refers to modified milk given to premature infants until about 6 months after birth.

Examples of these food products include natural food (treated with fats and oils) such as meat, fish, and nuts; food supplemented with fats and oils during preparation, such as Chinese foods, Chinese noodles, and soups; food products prepared using fats and oils as heating media, such as tempura (deep-fried fish and vegetables), deep-fried food, fried tofu, Chinese fried rice, doughnuts, and Japanese fried dough cookies (karinto)); fat- and oil-based food or processed food supplemented with fats and oils during processing, such as butter, margarine, mayonnaise, dressing, chocolate, instant noodles, caramel, biscuits, cookies, cake, and ice cream; and food sprayed or coated with fats and oils upon finishing, such as rice crackers, hard biscuits, and sweet bean paste bread. However, the food products of the present invention are not limited to food containing fats and oils, and other examples thereof include agricultural food products such as bakery products, noodles, cooked rice, sweets (e.g., candies, chewing gums, gummies, tablets, Japanese sweets), tofu, and processed products thereof; fermented food products such as refined sake, medicinal liquor, seasoning liquor (mirin), vinegar, soy sauce, and miso; livestock food products such as yogurt, ham, bacon, and sausage; seafood products such as fish paste (kamaboko), deep-fried fish paste (ageten), and fish cake (hanpen); and fruit drinks, soft drinks, sports drinks, alcoholic beverages, and tea.

Method for Strain Evaluation and Selection Using GPAT-Encoding Nucleic Acid or GPAT Protein of the Present Invention The present invention also provides a method of evaluating or selecting a lipid-producing fungus using the GPAT-encoding nucleic acid or GPAT protein of the present invention. Details are given below.

(1) Method for Evaluation

One embodiment of the present invention is a method of evaluating a lipid-producing fungus using the GPAT-encoding nucleic acid or GPAT protein of the present invention. In the method for evaluation of the present invention, for example, a lipid-producing fungus strain as a test strain is evaluated for the activity of the present invention using primers or probes designed based on the nucleotide sequence of the present invention. Such evaluation can be performed by known procedures, for example, described in International Publication No. WO01/040514 and JP-A-8-205900. The method for evaluation will be briefly described below.

The first step is preparation of a genome of a test strain. The genome can be prepared by any known method such as a Hereford method or a potassium acetate method (see, e.g., Methods in Yeast Genetics, Cold Spring Harbor Laboratory Press, p. 130 (1990)).

Primers or probes are designed based on the nucleotide sequence of the present invention, preferably the sequence set forth in SEQ ID NO: 1, SEQ ID NO: 4, or SEQ ID NO: 8. These primers or probes may be any regions of the nucleotide sequence of the present invention and may be designed by a known procedure. The number of nucleotides in a polynucleotide used as a primer is generally 10 or more, preferably 15 to 25. The number of nucleotides appropriate for a region to be flanked by primers is generally 300 to 2000.

The primers or probes prepared above are used to examine whether the genome of a test strain contains a sequence specific to the nucleotide sequence of the present invention or not. The sequence specific to the nucleotide sequence of the present invention can be detected by a known procedure. For example, a polynucleotide containing a part or all of the sequence specific to the nucleotide sequence of the present invention or a polynucleotide containing a nucleotide sequence complementary to the nucleotide sequence is used as one primer, and a polynucleotide containing a part or all of a sequence located upstream or downstream of this sequence or a polynucleotide containing a nucleotide sequence complementary to the nucleotide sequence is used as the other primer, and a nucleic acid from the test strain is amplified by PCR or other techniques. Further, for example, the presence or absence of an amplification product and the molecular weight of an amplification product can be measured.

PCR conditions suitable for the method of the present invention are not particularly limited and may be, for example, as follows:
  Denaturation temperature: 90° C. to 95° C.
  Annealing temperature: 40° C. to 60° C.
  Elongation temperature: 60° C. to 75° C.
  Number of cycles: 10 or more cycles.

The resulting reaction products can be separated by electrophoresis on an agarose gel or any other process to determine the molecular weight of the amplification product. The test strain can be predicted or evaluated for the activity of the present invention by confirming whether the molecular weight of the amplification product is enough for covering a nucleic acid molecule corresponding to a region specific to the nucleotide sequence of the present invention. Furthermore, the activity of the present invention can be predicted or evaluated with higher accuracy by analyzing the nucleotide sequence of the amplification product by the method described above. The method of evaluating the activity of the present invention is as described above.

Alternatively, in the evaluation according to the present invention, a test strain can be evaluated for the activity of the present invention by culturing the test strain and measuring the expression level of GPAT encoded by the nucleotide sequence of the present invention, e.g., the sequence set forth in SEQ ID NO: 1 or SEQ ID NO: 6. The expression level of GPAT can be measured by culturing a test strain under appropriate conditions and quantifying mRNA or protein for GPAT. The mRNA or protein can be quantified by a known procedure. For example, mRNA can be quantified by Northern hybridization or quantitative RT-PCR, and protein can be quantified by Western blotting (Current Protocols in Molecular Biology, John Wiley & Sons, 1994-2003).

(2) Method for Selection

Another embodiment of the present invention is a method of selecting a lipid-producing fungus using the GPAT-encoding nucleic acid or GPAT protein of the present invention. In the selection according to the present invention, a strain having a desired activity can be selected by culturing a test strain, measuring the expression level of GPAT encoded by the nucleotide sequence of the present invention, e.g., the sequence set forth in SEQ ID NO: 1, SEQ ID NO: 4, or SEQ ID NO: 8, and selecting a strain of a desired expression level. Alternatively, a desired strain can be selected by establishing a standard strain, culturing the standard strain and a test strain separately, measuring the expression level of each strain, and comparing the expression level of the standard strain with that of the test strain. Specifically, for example, a standard strain and test strains are cultured under appropriate conditions, and the expression level of each strain is measured. A strain exhibiting a desired activity can be selected by selecting a test strain showing higher or lower expression than the standard strain does. The desired activity can be determined by, for example, measuring the expression level of GPAT and the composition of fatty acids produced by GPAT, as described above.

In the selection according to the present invention, a test strain having a desired activity can also be selected by culturing test strains and selecting a strain having high or low activity of the present invention. A desired activity can be determined by, for example, measuring the expression level of GPAT and the composition of fatty acids produced by GPAT, as described above.

Examples of the test strain and the standard strain include, but not limited to, strains transformed with the vector of the present invention, strains modified to suppress expression of the nucleic acid of the present invention, mutagenized strains, and naturally mutated strains. The activity of the present invention can be measured by, for example, the method described in the "Nucleic acid encoding glycerol 3-phosphate acyltransferase of the present invention" in the specification. Examples of the mutagenesis include, but not limited to, physical methods such as irradiation with ultraviolet light or radiation; and chemical methods by treatment with a chemical such as EMS (ethylmethane sulfonate) or N-methyl-N-nitrosoguanidine (see, e.g., Yasuji Oshima ed., Biochemistry Experiments vol. 39, Experimental Protocols for Yeast Molecular Genetics, pp. 67-75, Japan Scientific Societies Press).

Examples of the strain used as the standard strain of the present invention or the test strain include, but not limited to, the lipid-producing fungus and yeast described above. Specifically, the standard strain and the test strain may be any combination of strains belonging to different genera or species, and one or more test strains may be simultaneously used.

The present invention will now be described in more detail by the following examples, which are not intended to limit the scope of the invention.

EXAMPLES

Example 1

Genomic Analysis of *Mortierella alpina*

*M. alpina* strain 1S-4 was inoculated into 100 mL of a GY2:1 medium (2% glucose, 1% yeast extract, pH 6.0) and was shake-cultured at 28° C. for 2 days. The cells were collected by filtration and genomic DNA was prepared by using DNeasy (QIAGEN).

The nucleotide sequence of the genomic DNA was determined with a Roche 454 GS FLX Standard. On this occasion, the nucleotide of a fragment library was sequenced in two runs, and the nucleotide of a mate pair library was sequenced in three runs. The resulting nucleotide sequences were assembled to obtain 300 supercontigs.

Example 2

Synthesis of cDNA and Construction of cDNA Library

*M. alpina* strain 1S-4 was inoculated into 4 mL of a medium (2% glucose, 1% yeast extract, pH 6.0) and was cultured at 28° C. for 4 days. The cells were collected by filtration, and RNA was extracted with an RNeasy plant kit (QIAGEN). Complemetary DNA was synthesized using a SuperScript First-Strand system for RT-PCR (Invitrogen). In addition, from the total RNA, poly(A)$^+$ RNA was purified using an Oligotex-dT30<Super>mRNA Purification Kit (Takara Bio Inc.). A cDNA library was constructed with a ZAP-cDNA Gigapack III Gold Cloning Kit (Stratagene).

Example 3

Search for GPAT Homolog

The amino acid sequence (GenBank Accession No. BAE78043) of plsB, GPAT derived from *Escherichia coli* (*E. coli*), was subjected to tblastn search for *M. alpina* strain 1S-4 genomic nucleotide sequences. As a result, a supercontig including the sequence set forth in SEQ ID NO: 7 gave a hit. The amino acid sequence of GPAT derived from yeast (*S. cerevisiae*), SCT1 (YBL011W) or GPT2 (YKR067W), was subjected to tblastn search for *M. alpina* strain 1S-4 genomic nucleotide sequences. As a result, supercontigs including the sequence set forth in SEQ ID NO: 12, SEQ ID NO: 13, SEQ ID NO: 14, or SEQ ID NO: 15 gave hits.

SEQ ID NO: 13 was the genomic sequence of MaGPAT1, and SEQ ID NO: 15 was the genomic sequence of MaGPAT2 (WO2008/156026). SEQ ID NO: 14 was the genomic sequence of MaGPAT3, which has been separately identified before by the present inventors (unpublished at the time of filing of the present application).

The genes relating to SEQ ID NO: 7 and SEQ ID NO: 12 were believed to be novel. The gene relating to SEQ ID NO: 7 was named MaGPAT4, and the gene relating to SEQ ID NO: 12 was named MaGPAT5.

Example 4

Cloning of MaGPAT4 and MaGPAT5

(1) Cloning of cDNA of MaGPAT4

In order to clone cDNA of MaGPAT4, the following primer was prepared.

A nucleotide sequence of a supercontig comprising the sequence set forth in SEQ ID NO: 4 was subjected to BLAST analysis and was compared with a known GPAT homolog. The result suggested that TAA at the 4246 to 4248 positions in the sequence set forth in SEQ ID NO: 4 was the stop codon. The start codon was difficult to be presumed from comparison with known homologs. Accordingly, cloning of the 5'-end of cDNA was attempted by a 5'-RACE method. That is, the cDNA on the 5' side upstream than the following primer:

Primer GPAT4-S: 5'-CAAGGATGTTGTTGATGAGGAAG-GCGAAG-3' (SEQ ID NO: 16) was cloned using the primer as a 5' gene specific primer and a Gene Racer Kit (Invitrogen). As a result, a sequence comprising the nucleotide sequence at the 93 to 595 positions of SEQ ID NO: 3 was obtained. This sequence, however, did not contain a sequence to be assumed as a start codon, and comparison with other GPAT homologs also suggested that the obtained sequence did not contain the start codon of MaGPAT4. Accordingly, genomic sequences, the sequence set forth in SEQ ID NO: 7 and the sequence at the 93 to 595 positions of SEQ ID NO: 3, were compared with each other, and the 5' upstream region where the both sequences coincide with each other was investigated in detail. As a result, ATG capable of serving as a start codon was found at two positions, the 596 to 598 and the 428 to 430, at downstream than the stop codon first appearing on the frame probably encoding MaGPAT4 on the genomic sequence. In order to clone CDS of MaGPAT4, the following primers were prepared using the ATG at the 596 to 598 positions as a start codon:

```
Primer SacI-GPAT4-1:
                                    (SEQ ID NO: 17)
5'-GAGCTCATGCCCATCGTTCCAGCTCAGC-3',
and Primer SalI-GPAT4-2:
                                    (SEQ ID NO: 18)
5'-GTCGACTTATAATTTCGGGGCGCCATCGC-3'.
```

PCR was performed with ExTaq (Takara Bio Inc.) using the cDNA as a template and a combination of primer SacI- GPAT4-1 and primer Sal-GPAT4-2 at 94° C. for 2 min and then 30 cycles of (94° C. for 1 min, 55° C. for 1 min, and 72° C. for 1 min). The amplified DNA fragment of about 2.5 kbp was cloned with a TOPO-TA cloning Kit (Invitrogen). A nucleotide sequence of the insert region was determined, and a plasmid having a nucleotide sequence set forth in SEQ ID NO: 3 was named pCR-MaGPAT4. A nucleotide sequence of a CDS encoding MaGPAT4 is shown in SEQ ID NO: 3, a nucleotide sequence of the ORF is shown in SEQ ID NO: 1, and an amino acid sequence of MaGPAT4 deduced from these nucleotide sequences is shown in SEQ ID NO: 2.

The sequence in the case of using the ATG at the 428 to 430 positions as a start codon was defined as MaGPAT4-long. A nucleotide sequence of a CDS encoding MaGPAT4-long is shown in SEQ ID NO: 6, a nucleotide sequence of the ORF is shown in SEQ ID NO: 4, and an amino acid sequence of MaGPAT4-long deduced from these nucleotide sequences is shown in SEQ ID NO: 5.

(2) Cloning of cDNA of MaGPAT5

In order to clone cDNA of MaGPAT5, the following primers were prepared:

```
Primer GPAT5-1F:
                                    (SEQ ID NO: 19)
5'-TTCCCTGAAGGCGTATCGAGCGACGATT-3',
and Primer GPAT5-3R:
                                    (SEQ ID NO: 20)
5'-CAAATGTTGACAGCAGCCAGAACG-3'.
```

PCR was performed with ExTaq (Takara Bio Inc.) using the thus-constructed library as a template and a combination of primer GPAT5-1F and primer GPAT5-3R at 94° C. for 2 min and then 30 cycles of (94° C. for 1 min, 55° C. for 1 min, and 72° C. for 1 min). The resulting DNA fragment of about 0.9 kbp was cloned with a TOPO-TA cloning Kit (Invitrogen). A nucleotide sequence of the insert region was determined, and a plasmid having a nucleotide sequence of the 1503 to 2385 positions of SEQ ID NO: 8 was named pCR-MaGPAT5-P.

Subsequently, probes was produced by PCR using these plasmids as templates and the primers in the above. In the reaction, ExTaq (Takara Bio Inc., Japan) was used, except that a PCR labeling mix (Roche Diagnostics) was used instead of the attached dNTP mix for labeling DNA to be amplified with digoxigenin (DIG) to prepare MaGPAT5 probes. The cDNA library was screened with these probes.

Hybridization conditions were set as follows:
Buffer: 5×SSC, 1% SDS, 50 mM Tris-HCl (pH 7.5), 50% formamide,
Temperature: 42° C. (overnight), and
Washing conditions: 0.2×SSC, in 0.1% SDS solution (65° C.) for 20 min (three times).

A DIG nucleic acid detection kit (Roche Diagnostics) was used for detection. Plasmids were cut out by in vivo excision from phage clones obtained by screening to obtain each plasmid DNA. A plasmid having the longest insert among the plasmids obtained by screening with the MaGPAT5 probe included the nucleotide sequence set forth in SEQ ID NO: 11 and was named plasmid pB-MaGPAT5. The nucleotide sequence set forth in SEQ ID NO: 11 was searched for ORF. As a result, a CDS having a start codon at the 225 to 227 positions of SEQ ID NO: 11 and a stop codon at the 2589 to 2591 positions of SEQ ID NO: 11 were found. The result of blastp search of an amino acid sequence deduced by this sequence and other information suggested that this CDS encodes MaGPAT5. The CDS of a gene encoding MaGPAT5 is shown in SEQ ID NO: 10, the ORF is shown in SEQ ID NO: 8, and an amino acid sequence of MaGPAT5 deduced from these nucleotide sequences is shown in SEQ ID NO: 9.

(3) Sequence Analysis

The genomic sequence (SEQ ID NO: 7) and the CDS sequence (SEQ ID NO: 3) of the MaGPAT4 gene were compared with each other. The result suggested that the genomic sequence of this gene is composed of ten exons and nine introns and encodes a protein consisting of 825 amino acid residues (FIGS. 1 and 2). Comparison between the genomic sequence (SEQ ID NO: 12) and the CDS sequence (SEQ ID NO: 10) of the MaGPAT5 gene suggested that the genomic sequence of this gene is composed of three exons and two introns and encodes a protein consisting of 788 amino acid residues (FIGS. 3 and 4).

MaGPAT4 and MaGPAT5 were compared with a known GPAT homolog derived from *Mortierella alpina*. Tables 2 and 3 show CDS sequences and identity of amino acid sequences deduced from the CDS sequences.

TABLE 2

Identity (%) of CDS with GPAT homolog derived from *Mortierella*

|  | MaGPAT1 | MaGPAT2 | MaGPAT3 | MaGPAT4 | MaGPAT5 |
|---|---|---|---|---|---|
| MaGPAT1 | — | 42.4 | 73.2 | 44.9 | 44.5 |
| MaGPAT2 |  | — | 38.7 | 39.9 | 39.0 |
| MaGPAT3 |  |  | — | 45.1 | 45.5 |
| MaGPAT4 |  |  |  | — | 44.0 |
| MaGPAT5 |  |  |  |  | — |

TABLE 3

Identity (%) of amino acid sequence with GPAT homolog derived from *Mortierella*

|  | MaGPAT1 | MaGPAT2 | MaGPAT3 | MaGPAT4 | MaGPAT5 |
|---|---|---|---|---|---|
| MaGPAT1 | — | 16.0 | 83.7 | 13.1 | 18.7 |
| MaGPAT2 |  | — | 14.4 | 13.8 | 11.6 |
| MaGPAT3 |  |  | — | 13.5 | 18.0 |
| MaGPAT4 |  |  |  | — | 11.3 |
| MaGPAT5 |  |  |  |  | — |

Figure 5:
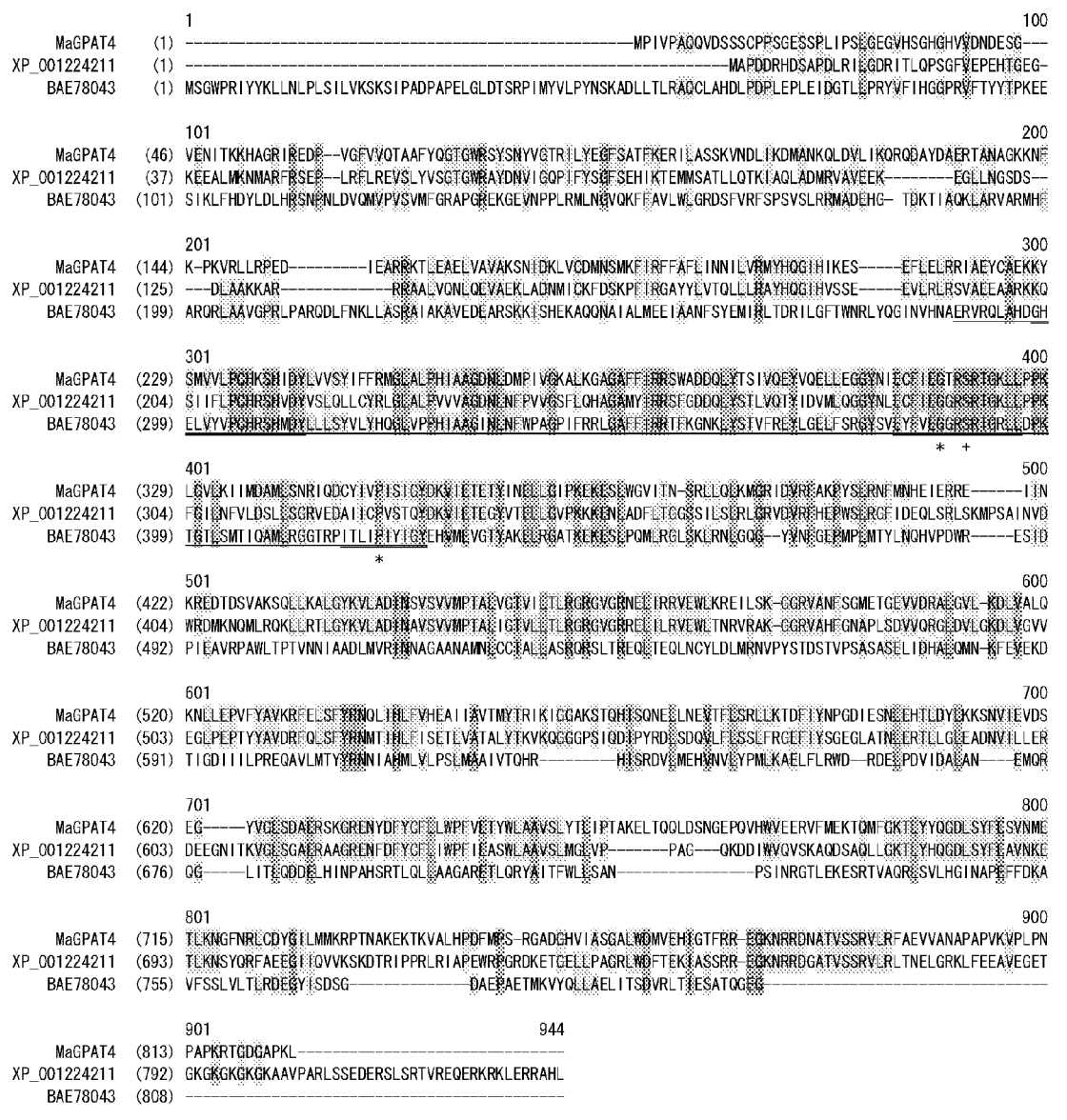

The deduced amino acid sequence (SEQ ID NO: 2) of MaGPAT4 was subjected to homology analysis against amino acid sequences registered in GenBank nr with BLASTp. The amino acid sequence showing the lowest E-value against this sequence, i.e., having the highest identity was the amino acid sequence (GenBank Accession No. XP_001224211) of a deduced protein derived from ascomycete *Chaetomium globosum* CBS148.51, and the identity thereof was 39.3%. The amino acid sequence also had a homology with glycerone phosphate O-acyltransferase (GNPAT) derived from an animal, and the identity with human GNPAT (GenBank Accession No. AAH00450) was 22.6%. The identity of the amino acid sequence (GenBank accession No. BAE78043) with the GPAT derived from *Escherichia coli* (*E. coli*), plsB protein, was 17.6%. FIG. 5 shows alignment of MaGPAT4 with these amino acid sequences.

Similarly, the deduced amino acid sequence (SEQ ID NO: 9) of MaGPAT5 was subjected to homology analysis against amino acid sequences registered in GenBank nr with BLASTp. The amino acid sequence showing the lowest E-value against this sequence, i.e., having the highest identity was the amino acid sequence (GenBank accession No. XP_759516) of a deduced protein UM03369 derived from ascomycete *Ustilago maydis* 521, and the identity thereof was 15.4%. FIG. 6 shows alignment of MaGPAT5 with these amino acid sequences.

Both MaGPAT4 and MaGPAT5 conserved the region that is conserved in acyltransferase, in particular, conserved the glycine residue (G) and the proline residue (P) indicated by the symbol *, which are considered to be important for the acyltransferase activity. Furthermore, the serine residue (S) indicated by the symbol +, which is considered to be important for binding with G3P, was also conserved (FIGS. 5 and 6).

Example 5

Functional Analysis of MaGPAT4

(1) Construction of Vector Expressing MaGPAT4 in Yeast

A DNA fragment prepared by digesting yeast expression vector pYE22m (Biosci. Biotech. Biochem., 59, 1221-1228, 1995) with restriction enzymes EcoRI and SalI and a DNA fragment of about 2.1 kbp prepared by digesting plasmid pCR-MaGPAT4 with restriction enzymes EcoRI and SalI were linked each other by using ligation high (TOYOBO) to construct plasmid pYE-MaGPAT4.

Separately, expression vectors expressing MaGPAT1, MaGPAT2, or MaGPAT3 in yeast were constructed for comparison. The vectors expressing MaGPAT1 and MaGPAT2 in yeast were constructed as described in WO2008/156026, and named pYE-MaGPAT1 and pYE-MaGPAT2, respectively. The vector expressing MaGPAT3 in yeast was prepared as follows. A tblastn search was performed against *M. alpina* strain 1S-4 genomic nucleotide sequences prepared as in Example 1 using the amino acid sequence of MaGPAT1 (ATCC No. 16266) as a query. As a result, a gene having a homology with MaGPAT1 was identified and was named MaGPAT3 (unpublished at the time of filing of the present application). The following primers:

```
Eco-MaGPAT3-F:
                                        (SEQ ID NO: 26)
5'-GAATTCATGGGTCTCCAGATCTATGACTTCGTCTC-3',
and
```

```
Sal-MaGPAT3-R:
                                        (SEQ ID NO: 27)
5'-GTCGACTTATGCCTCCTTAGACTTGACTGCATCC-3'
``` were prepared. PCR was performed with KOD-Plus- (TOYOBO) using the cDNA described in Example 2 as a template and these primers. As a result, a DNA fragment of about 2.2 kbp was amplified. The fragment was cloned with a Zero Blunt TOPO PCR cloning kit (Invitrogen), and the resulting plasmid was named pCR-MaGPAT3. Plasmid pCR-MaGPAT3 was digested with restriction enzymes EcoRI and SalI to prepare a DNA fragment of about 2.3 kbp, and this DNA fragment was inserted into the EcoRI and SanI sites of expression vector pYE22m for yeast to prepare plasmid pYE-MaGPAT3.

(2) Preparation of Transformant

Yeast *S. cerevisiae* strain EH13-15 (trp1, MATα) (Appl. Microbiol. Biotechnol., 30, 515-520, 1989) was transformed by a lithium acetate method using plasmid pYE22m, pYE-MaGPAT4, pYE-MaGPAT1, pYE-MaGPAT2, or pYE-MaGPAT3. Transformants that grew on SC-Trp (containing, per liter, 6.7 g of yeast nitrogen base w/o amino acids (DIFCO), 20 g of glucose, and 1.3 g of amino acid powder (a mixture of 1.25 g of adenine sulfate, 0.6 g of arginine, 3 g of aspartic acid, 3 g of glutamic acid, 0.6 g of histidine, 1.8 g of leucine, 0.9 g of lysine, 0.6 g of methionine, 1.5 g of phenylalanine, 11.25 g of serine, 0.9 g of tyrosine, 4.5 g of valine, 6 g of threonine, and 0.6 g of uracil)) agar medium (2% agar) were selected.

(3) Culture of Yeast

Arbitrary two strains from the strains obtained by transformation with plasmid pYE22m were named C-1 strain and C-2 strain, and arbitrary two strains from the strains obtained by transformation with plasmid pYE-MaGPAT4 were named MaGPAT4-1 strain and MaGPAT4-2 strain. These strains were subjected to the following culturing experiment. For comparison, arbitrary two strains from the strains obtained by transformation with plasmid pYE-MaGPAT1 were named MaGPAT1-1 strain and MaGPAT1-2 strain, arbitrary two strains from the strains obtained by transformation with plasmid pYE-MaGPAT2 were named MaGPAT2-1 strain and MaGPAT2-2 strain, and arbitrary two strains from the strains obtained by transformation with plasmid pYE-MaGPAT3 were named MaGPAT3-1 strain and MaGPAT3-2 strain, and these strains were also subjected to the following culturing experiment as in the MaGPAT4-1 strain and MaGPAT4-2 strain.

As pre-culture, one platinum loop of yeast cells from the plate were inoculated in 10 mL of an SC-Trp medium and were shake-cultured at 30° C. for 1 day. In main culture, 500 μL of the pre-culture solution was added to 10 mL of an SC-Tip medium or a YPD (2% yeast extract, 1% polypeptone, and 2% glucose) medium, followed by shake culture at 30° C. for 2 days.

(4) Analysis of Cellular Fatty Acids

The yeast cells were collected by centrifugation of the culture solution. The cells were washed with 10 mL of sterilized water, collected again by centrifugation, and lyophilized. To the lyophilized yeast cells, 4 mL of a mixture containing chloroform:methanol (2:1) was added and vigorously agitated, and then allowed to stand at 70° C. for 1 hour. The yeast cells were separated by centrifugation, and the solvent was collected. To the remaining cells, 4 mL of the mixture of chloroform:methanol (2:1) was added again, and the solvent was collected in a similar manner. The lipid was dried with Speedback, and 2 mL of chloroform was added thereto to dissolve the lipid. Two hundred microliters of this solution was sampled, and the fatty acids of the cells were converted into methyl ester by a hydrochloric acid-methanol method and were extracted with hexane. Hexane was distilled off, followed by gas chromatographic analysis. The results are shown in Tables 4 to 7.

TABLE 4

Fatty acid composition (%) in cells (Medium: YPD)

|  | C-1 | C-2 | MaGPAT4-1 | MaGPAT4-2 | MaGPAT2-1 | MaGPAT2-2 |
|---|---|---|---|---|---|---|
| 16:0 | 4.91 | 4.69 | 14.13 | 12.24 | 3.57 | 3.82 |
| 16:1 | 41.52 | 40.66 | 24.42 | 29.42 | 38.02 | 34.34 |
| 18:0 | 4.17 | 4.29 | 6.02 | 5.88 | 4.98 | 4.62 |
| 18:1 | 45.77 | 46.10 | 51.53 | 49.16 | 49.63 | 52.63 |
| Others | 3.63 | 4.26 | 3.91 | 3.31 | 3.81 | 4.59 |

|  | C-1 | C-2 | MaGPAT1-1 | MaGPAT1-2 | MaGPAT3-1 | MaGPAT3-2 |
|---|---|---|---|---|---|---|
| 16:0 | 4.40 | 4.37 | 5.04 | 4.88 | 6.41 | 6.23 |
| 16:1 | 40.07 | 39.83 | 39.03 | 38.48 | 38.15 | 38.15 |
| 18:0 | 3.99 | 3.85 | 4.32 | 4.42 | 4.75 | 4.84 |
| 18:1 | 48.73 | 49.05 | 48.96 | 49.68 | 47.99 | 48.29 |
| Others | 2.80 | 2.89 | 2.65 | 2.54 | 2.70 | 2.49 |

TABLE 5

Fatty acid composition (%) in cells (Medium: SD-Trp)

|  | C-1 | C-2 | MaGPAT4-1 | MaGPAT4-2 | MaGPAT2-1 | MaGPAT2-2 |
|---|---|---|---|---|---|---|
| 16:0 | 7.22 | 7.51 | 19.94 | 21.97 | 7.19 | 7.08 |
| 16:1 | 36.71 | 36.49 | 16.18 | 17.41 | 32.66 | 33.02 |
| 18:0 | 5.87 | 5.98 | 11.66 | 7.03 | 6.41 | 6.67 |
| 18:1 | 45.90 | 46.17 | 47.86 | 48.43 | 49.25 | 49.15 |
| Others | 4.29 | 3.85 | 4.35 | 5.17 | 4.48 | 4.09 |

TABLE 6

Fatty acid content (%) in cells

| C-1 | C-2 | MaGPAT4-1 | MaGPAT4-2 | MaGPAT2-1 | MaGPAT2-2 |
|---|---|---|---|---|---|
| 2.89 | 2.89 | 5.32 | 5.73 | 2.95 | 4.30 |

(Medium: YPD)

TABLE 7

Fatty acid content (%) in cells

| C-1 | C-2 | MaGPAT4-1 | MaGPAT4-2 | MaGPAT2-1 | MaGPAT2-2 |
|---|---|---|---|---|---|
| 5.36 | 4.86 | 9.04 | 11.63 | 5.93 | 5.89 |

(Medium: SD-Trp)

As shown in Tables 4 and 5, the compositional ratio of fatty acids constituting the lipid in the cells of a strain highly expressing MaGPAT4 has a high ratio of palmitic acid (16:0) and a low ratio of palmitoleic acid (16:1), compared with those of the control strain into which the vector only was introduced. This tendency is different from the tendencies when another GPAT derived from *Mortierella alpina*, i.e., MaGPAT1, MaGPAT2, or MaGPAT3, was used. Accordingly, MaGPAT4 of the present invention has a substrate specificity different from those of other GPATs derived from *Mortierella alpina*.

In addition, as shown in Tables 6 and 7, the fatty acid content in the cells of a strain highly expressing MaGPAT4 increased to about twice that in the control strain.

Example 6

Functional Analysis of MaGPAT4-Long and MaGPAT4

(1) Construction of Galactose-Inducible Expression Vector

In order to induce expression of MaGPAT4-long or MaGPAT4 with galactose, a plasmid containing a galactose-inducible promoter was constructed as follows.

PCR was performed with ExTaq (Takara Bio Inc.) using the cDNA prepared in Example 2 as a template and a combination of primer Not-MaGPAT4-F1 and primer Bam-MaGPAT4-R or a combination of primer Not-MaGPAT4-F2 and primer Bam-MaGPAT4-R at 94° C. for 2 min and then 30 cycles of (94° C. for 1 min, 55° C. for 1 min, and 72° C. for 1 min). The amplified DNA fragments of about 2.7 kbp and about 2.5 kbp were cloned with a TOPO-TA cloning Kit (Invitrogen) and were confirmed to have the CDS sequence of GPAT4-long set forth in SEQ ID NO: 6 and the CDS sequence of GPAT4 set forth in SEQ ID NO: 3, respectively, and named plasmid pCR-MaGPAT4-long-1 and plasmid pCR-MaGPAT4-1, respectively. The DNA fragment of about 6.5 kbp obtained by digestion of vector pESC-TRP (Stratagene) with restriction enzymes NotI and BglII was linked to a DNA fragment of about 2.7 kbp or 2.5 kbp obtained by digestion of plasmid pCR-MaGPAT4-long-1 or plasmid pCR-MaGPAT4-1 with restriction enzymes NotI and BamHI using ligation high (TOYOBO) to prepare plasmid pESC-T-MaGPAT4-long or plasmid pESC-T-MaGPAT4.

```
Primer Not-MaGPAT4-F1:
                                     (SEQ ID NO: 28)
5'-GCGGCCGCATGACAACCGGCGACAGTACCG-3'

Primer Not-MaGPAT4-F2:
                                     (SEQ ID NO: 29)
5'-GCGGCCGCATGCCCATCGTTCCAGCTCAG-3'

Primer Bam-MaGPAT4-R:
                                     (SEQ ID NO: 30)
5'-GGATCCTTATAATTTCGGGGCGCCATCG-3'
```

(2) Preparation of Transformant

Yeast *S. cerevisiae* strain EH13-15 was transformed by a lithium acetate method using pESC-TRP, pESC-T-MaGPAT4-long, or pESC-T-MaGPAT4. Transformants that grew on an SC-Trp agar medium were selected.

(3) Culture of Yeast

Arbitrary four strains from the transformants obtained by transformation with each plasmid were each inoculated in 10 mL of an SD-Trp liquid medium and were shake-cultured at 30° C. for 1 day, as pre-culture. In main culture, each of 1 mL of the pre-culture solution was inoculated in 10 mL of an SG-Trp (containing, per liter, 6.7 g of yeast nitrogen base w/o amino acids (DIFCO), 20 g of glucose, and 1.3 g of amino acid powder (a mixture of 1.25 g of adenine sulfate, 0.6 g of arginine, 3 g of aspartic acid, 3 g of glutamic acid, 0.6 g of histidine, 1.8 g of leucine, 0.9 g of lysine, 0.6 g of methionine, 1.5 g of phenylalanine, 11.25 g of serine, 0.9 g of tyrosine, 4.5 g of valine, 6 g of threonine, and 0.6 g of uracil)) liquid medium in duplicate, followed by shake culture at 30° C. for 2 days to induce expression of MaGPAT4-long or MaGPAT4.

(4) Analysis of Fatty Acids

The yeast cells were collected by centrifugation of the culture solution. The cells were washed with 10 mL of sterilized water, collected again by centrifugation, and lyophilized. The fatty acids in the cells of one line of each strain were converted into methyl ester by a hydrochloric acid-methanol method and were subjected to gas chromatographic analysis of the total fatty acids contained in the cells (Table 8).

Lipids in the cells of another line of each strain were extracted as follows. That is, 1 mL of a mixture containing chloroform:methanol (2:1) and glass beads were added to the cells, and the cells were disrupted with a bead beater. Thereafter, centrifugation was conducted and the supernatant was collected. Further one milliliter of the mixture of chloroform:methanol (2:1) was added to the remaining cells, and the supernatant was similarly collected. This procedure was repeated, and lipids were extracted with 4 mL of the mixture of chloroform:methanol (2:1) in total. The solvent was distilled off with Speedback, and the residue was dissolved in a small amount of chloroform. The lipids were fractionated on a silica gel 60 plate (Merck) by thin layer chromatography using hexane:diethyl ether:acetic acid=70:30:1 as the eluent. The lipids were visualized by spraying a primulin solution and then irradiated with UV light. The triacylglycerol (TG) fraction, free-fatty acid (FFA) fraction, diacylglycerol (DG) fraction, and phospholipid (PL) fraction were scraped from the plate and were respectively put in tubes. The fatty acids were converted into methyl esters by a hydrochloric acid-methanol method and were subjected to gas chromatographic analysis of the fatty acids (Table 9, FIG. 7).

The results of analysis of each gene-introduced strain are shown below. The strain introduced with a vector, pESC-TRP, was used as a control.

TABLE 8

| Total amount of fatty acids in cells (SG-Trp culture) | | |
|---|---|---|
| Control | MaGPAT4-long | MaGPAT4 |
| 147.12 ± 6.18 | 254.58 ± 6.16 | 290.08 ± 19.67 |

Average ± SD

TABLE 9

| Amount of fatty acids in lipid fraction (SG-Trp culture) | | | |
|---|---|---|---|
| | Control | MaGPAT4-long | MaGPAT4 |
| FFA | 5.12 ± 1.26 | 8.53 ± 1.37 | 13.98 ± 2.80 |
| TG | 43.18 ± 2.76 | 122.55 ± 4.40 | 149.74 ± 16.81 |
| DG | 4.75 ± 0.38 | 10.78 ± 0.28 | 22.08 ± 5.15 |
| PL | 87.09 ± 2.49 | 96.03 ± 2.88 | 103.88 ± 8.02 |

Average ± SD

The total amounts of fatty acids in the strain expressing MaGPAT4-long and in the strain expressing MaGPAT4 increased by 1.7-fold and 2.0-fold, respectively, compared with that in the control (Table 8).

The amounts of PL in the strain expressing MaGPAT4-long and in the strain expressing MaGPAT4 were respectively 1.1-fold and 1.2-fold that in the control. Thus, these strains showed almost no difference to the control. In contrast, the amounts of TG in the strain expressing MaGPAT4-long and in the strain expressing MaGPAT4 notably increased to be 2.8-fold and 3.5-fold, respectively, that in the control. That is, expression of MaGPAT4-long or MaGPAT4 could activate biosynthesis of fatty acids and enhance the productivity of a reserve lipid, TG. In addition, the amounts of DG and FFA in the strain expressing MaGPAT4-long and in the strain expressing MaGPAT4 increased compared with those in the control (Table 9).

The proportions of fatty acids in each lipid fraction are shown in FIG. 7. In the FFA fraction, the proportions of fatty acids in the strain expressing MaGPAT4-long and in the strain expressing MaGPAT4 did almost not differ from those in the control, whereas, in the other fractions, there were tendency of an increase in saturated fatty acids and a decrease in unsaturated fatty acids in the strain expressing MaGPAT4-long and in the strain expressing MaGPAT4. In particular, 16:0 (palmitic acid) increased, and 16:1 (palmitoleic acid) decreased.

Figure 8:
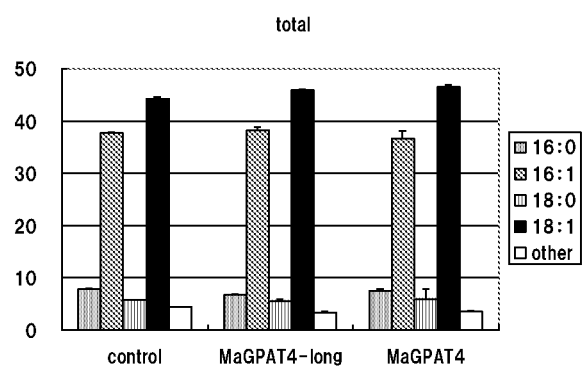
FIG. 8 is a graph showing a composition of total fatty acids when yeast transformed with a plasmid containing MaGPAT4-long or MaGPAT4 linked to a galactose-inducible promoter was cultured in a SC-Tip medium not containing galactose.

Furthermore, the main culture was performed using an SC-Trp liquid medium instead of the SG-Trp liquid medium. Since the SC-Trp liquid medium does not contain galactose, expression of MaGPAT4-long or MaGPAT4 introduced by transformation is not induced in the main culture using this medium. In the experiment using the SC-Trp liquid medium, no differences were observed in both the amount and proportions of the total fatty acids of the cells between the control and the strain introduced with MaGPAT4-long or MaGPAT4 (Table 10, FIG. 8). This also suggested that expression of MaGPAT4-long or MaGPAT4 was induced by galactose, resulting in an increase of the fatty acids in the cells in the SG-Trp medium.

TABLE 10

| Total amount of fatty acids in cells (SC-Trp culture) | | | |
|---|---|---|---|
| | Control | GPAT4-long | GPAT4 |
| mg/L broth | 153.26 ± 3.05 | 150.98 ± 6.48 | 156.35 ± 8.06 |

Example 7

Complementary Experiment of Yeast S. cerevisiae Δsct1 and Δgpt2

In yeast S. cerevisiae, SCT1 and GPT2 are known as genes involved in the GPAT activity, and simultaneous deficiency in these genes is known to result in death. In order to confirm whether the products of MaGPAT4 and MaGPAT4-long derived from Mortierella alpina have the GPAT activity, a complementary experiment of Δsct1 and Δgpt2 was performed. Table 11 summarizes the genotypes of strains produced as below.

TABLE 11

| Strain | | |
|---|---|---|
| YSC1021-663938 | diploid | Δgpt2:KanMX/Δgpt2:KanMX, ura3/ura3, leu2/leu2, MET15/met15, LYS2/lys2 |
| GP-1 | diploid | Δgpt2:KanMX/Δgpt2:KanMX, SCT1/Δsct1:LEU2, ura3/ura3, leu2/leu2, MET15/met15, LYS2/lys2 |

(1) Production of GP-1 Strain

The SCT1 gene of Δgpt2 homozygous diploid yeast (catalog No. YSC1021-663938) of a yeast knock out strain collection (Open Biosystems) was disrupted as follows. DNA was extracted from S. cerevisiae strain S288C cells using Dr. GenTLE (from yeast) (TaKaRa Bio Inc.). A fragment of the SCT1 gene was amplified by PCR with KOD-Plus- (TOYOBO) using the resulting DNA as a template, primer XbaI-Des-SCT1-F: 5'-TCTAGAATGCCTGCAC-CAAAACTCAC-3' (SEQ ID NO: 31) and primer XbaI-Des-SCT1-R: 5'-TCTAGACCACAAGGTGATCAGGAAGA-3' (SEQ ID NO: 32). The amplified DNA fragment of about 1.3 kbp was cloned using a Zero Blunt TOPO PCR cloning kit (Invitrogen), and the resulting plasmid was named pCR-SCT1P. Subsequently, a DNA fragment of about 2.2 kbp containing CDS of the LEU2 gene obtained by digestion of plasmid YEp13 with restriction enzymes SalI and XhoI was linked to a DNA fragment of about 4.4 kbp obtained by digestion of plasmid pCR-SCT1P with SalI using ligation high (TOYOBO) to prepare a plasmid, pCR-Δsct1:LEU2, where the LEU2 gene was inserted in reverse orientation with respect to the SCT1 gene. This was digested with a restriction enzyme XbaI, and the Δgpt2 homozygous diploid yeast was transformed by a lithium acetate method. A transformant that grew on SD-Leu (containing, per liter, 6.7 g of yeast nitrogen base w/o amino acids (DIFCO), 20 g of glucose, and 1.3 g of amino acid powder (a mixture of 1.25 g of adenine sulfate, 0.6 g of arginine, 3 g of aspartic acid, 3 g of glutamic acid, 0.6 g of histidine, 0.9 g of lysine, 0.6 g of methionine, 1.5 g of phenylalanine, 11.25 g of serine, 0.9 g of tyrosine, 4.5 g of valine, 6 g of threonine, 1.2 g of tryptophan, and 0.6 g of uracil)) agar medium (2% agar) was selected. DNA was extracted from the resulting transformant cells by the method described above. PCR was performed using a combination (a) primer SCT1outORF-F: 5'-AGTGTAGGAAGCCCG-GAATT-3' (SEQ ID NO: 33) and primer SCT1inORF-R: 5'-GCGTAGATCCAACAGACTAC-3' (SEQ ID NO: 34) (0.5 kbp) or a combination (b) primer SCT1outORF-F and primer LEU21n ORF-F: 5'-TTGCCTCTTCCAAGAGCACA-3' (SEQ ID NO: 35) (1.2 kbp) to confirm the genotype, i.e., to confirm to be SCT1/Δsct1:LEU2, and the strain was named GP-1 strain.

(2) Construction of Galactose-Inducible Expression Vector Using URA3 as a Marker A DNA fragment of about 6.6 kbp obtained by digestion of vector pESC-URA (Stratagene) with restriction enzymes NotI and BglII was linked to a DNA fragment of about 2.7 kbp or 2.5 kbp obtained by digestion of plasmid pCR-MaGPAT4-long-1 or plasmid pCR-MaGPAT4-1 with restriction enzymes NotI and BamHI using ligation high (TOYOBO) to prepare plasmid pESC-U-MaGPAT4-long and plasmid pESC-U-MaGPAT4.

(3) Preparation of Transformant

Yeast GP-1 strain was transformed by a lithium acetate method using pESC-URA, pESC-U-MaGPAT4-long, or pESC-U-MaGPAT4. Transformants that grew on an SC-Ura (containing, per liter, 6.7 g of yeast nitrogen base w/o amino acids (DIFCO), 20 g of glucose, and 1.3 g of amino acid powder (a mixture of 1.25 g of adenine sulfate, 0.6 g of arginine, 3 g of aspartic acid, 3 g of glutamic acid, 0.6 g of histidine, 0.9 g of lysine, 0.6 g of methionine, 1.5 g of phenylalanine, 11.25 g of serine, 0.9 g of tyrosine, 4.5 g of valine, 6 g of threonine, 1.2 g of tryptophan, and 1.8 g of leucine)) agar medium (2% agar) were selected. The strain obtained by transformation with pESC-URA was named C-D strain, and strains obtained by transformation with pESC-U-MaGPAT4-long and pESC-U-MaGPAT4 were named MaGPAT4-long-D strain and MaGPAT4-D strain, respectively.

(4) Spore Formation and Tetrad Analysis

The C-D strain, MaGPAT4-long-D strain, and MaGPAT4-D strain were each applied to a YPD agar medium and were cultured at 30° C. for 1 day. The grown cells were applied to a spore-forming agar medium (0.5% potassium acetate, 2% agar) and were cultured at 20° C. for 7 days. An appropriate amount of the resulting cells were scraped and were suspended in 100 μL of a zymolyase solution (0.125 mg/mL of zymolyase 100T, 1 M sorbitol, 40 mM potassium phosphate buffer (pH 6.8)). The suspension was incubated at room temperature for 30 min, and the tube containing the suspension was then placed in ice. After confirmation of ascospore formation under a microscope, four ascospores were isolated on a YPDGal (2% yeast extract, 1% peptone, and 2% galactose) agar medium by micromanipulation, followed by incubation at 30° C. for 2 days to obtain colonies derived from each of the spores.

The resulting spore clones were replicated by incubation on an SG-Ura (containing, per liter, 6.7 g of yeast nitrogen base w/o amino acids (DIFCO), 20 g of galactose, and 1.3 g of amino acid powder (a mixture of 1.25 g of adenine sulfate, 0.6 g of arginine, 3 g of aspartic acid, 3 g of glutamic acid, 0.6 g of histidine, 0.9 g of lysine, 0.6 g of methionine, 1.5 g of phenylalanine, 11.25 g of serine, 0.9 g of tyrosine, 4.5 g of valine, 6 g of threonine, 1.2 g of tryptophan, and 1.8 g of leucine)) agar medium (2% agar) and an SG-Leu (containing, per liter, 6.7 g of yeast nitrogen base w/o amino acids (DIFCO), 20 g of galactose, and 1.3 g of amino acid powder (a mixture of 1.25 g of adenine sulfate, 0.6 g of arginine, 3 g of aspartic acid, 3 g of glutamic acid, 0.6 g of histidine, 0.9 g of lysine, 0.6 g of methionine, 1.5 g of phenylalanine, 11.25 g of serine, 0.9 g of tyrosine, 4.5 g of valine, 6 g of threonine, 1.2 g of tryptophan, and 0.6 g of uracil)) agar medium (2% agar) at 30° C. for 3 days for investigating uracil auxotrophy and leucine auxotrophy. In a clone showing the uracil auxotrophy, the introduced plasmid was considered to be lost. Accordingly, such a clone was not subjected to the following analysis.

Among the four ascospores isolated from C-D strain, two ascospores could grow on the YPGal agar medium, and all strains showed leucine auxotrophy. All the four ascospores isolated from MaGPAT4-long-D strain or MaGPAT4-D strain could grow on the YPGal agar medium. By investigation of leucine auxotrophy, two of the four ascospores showed leucine auxotrophy, and the other two showed leucine non-auxotrophy.

The genotypes of the resulting strains were investigated by extracting DNA from the cells as described above and performing PCR using a combination (a) primer SCT1outORF-F and primer SCT11n ORF-R and a combination (b) primer SCT1outORF-F and primer LEU2 in ORF-F. As a result, the leucine non-auxotrophic strains were not amplified by the PCR using the combination (a), but were amplified by the PCR using the combination (b). These strains were thus confirmed to have Δsct1:LEU2 alleles. The leucine auxotrophic strains were amplified by the PCR using the combination (a), but were not amplified by the PCR using the combination (b). These strains were thus confirmed to have SCT1 alleles.

Furthermore, the strains derived from the four ascospores isolated from MaGPAT4-long-D strain or MaGPAT4-D strain were each applied onto a YPD agar medium. The growth of two strains was well, but the growth of the other two strains was considerably poor. The strains showing poor growth corresponded to the leucine non-auxotrophic strains having Δsct1:LEU2 alleles.

These results confirmed that though a Δsct1 Δgpt2 strain having deficiency in two genes involved in the GPAT activity of yeast results in death, the strain can grow by expressing MaGPAT4-long or MaGPAT4. That is, it was strongly suggested that the MaGPAT4-long protein and the MaGPAT4 protein have the GPAT activity.

Example 8

Overexpression of GPAT4 in *Mortierella alpina*

(1) Construction of expression vector for *M. alpina*

In order to express GPAT4 in *M. alpina*, vectors were constructed as follows.

Vector pUC18 was digested with restriction enzymes EcoRI and HindIII, and an adapter prepared by annealing oligoDNAs, MCS-for-pUC18-F2 and MCS-for-pUC18—R2 was inserted to construct plasmid pUC18-RF2.

```
MCS-for-pUC18-F2:
                                        (SEQ ID NO: 36)
5'-AATTCATAAGAATGCGGCCGCTAAACTATTCTAGACTAGGTCGACG

GCGCGCCA-3'

MCS-for-pUC18-R2:
                                        (SEQ ID NO: 37)
5'-AGCTTGGCGCGCCGTCGACCTAGTCTAGAATAGTTTAGCGGCCGCA

TTCTTATG-3'
```

A DNA fragment of about 0.5 kbp amplified by PCR with KOD-plus-(TOYOBO) using the genome of *M. alpina* as a template, primer Not1-GAPDHt-F and primer EcoR1-Asc1-GAPDHt-R was cloned with a Zero Blunt TOPO PCR Cloning Kit (Invitrogen). After confirmation of the nucleotide sequence of the insert region, a DNA fragment of about 0.9 kbp obtained by digestion with restriction enzymes NotI and EcoRI was inserted into the NotI and EcoRI sites of plasmid pUC18-RF2 to construct plasmid pDG-1.

```
Primer Not1-GAPDHt-F:
                                        (SEQ ID NO: 38)
5'-AGCGGCCGCATAGGGGAGATCGAACC-3'

Primer EcoR1-Asc1-GAPDHt-R:
                                        (SEQ ID NO: 39)
5'-AGAATTCGGCGCGCCATGCACGGGTCCTTCTCA-3'
```

A DNA fragment amplified by PCR with KOD-plus-(TOYOBO) using the genome of *M. alpina* as a template and primer URA5g-F1 and primer URA5g-R1 was cloned with a Zero Blunt TOPO PCR Cloning Kit (Invitrogen). After confirmation of the nucleotide sequence of the insert region, a DNA fragment of about 2 kbp obtained by digestion with a restriction enzyme SalI was inserted into the SalI site of plasmid pDG-1 in such a manner that the 5' side of the URA5 gene was at the EcoRI side of the vector to construct plasmid pDuraG.

```
Primer URA5g-F1:
                                        (SEQ ID NO: 40)
5'-GTCGACCATGACAAGTTTGC-3'

Primer URA5g-R1:
                                        (SEQ ID NO: 41)
5'-GTCGACTGGAAGACGAGCACG-3'
```

Subsequently, a DNA fragment of about 1.0 kbp amplified by PCR with KOD-plus-(TOYOBO) using the genome of *M. alpina* as a template and primer hisHp+URA5-F and primer hisHp+MGt-F was linked to a DNA fragment of about 5.3 kbp amplified by PCR with KOD-plus-(TOYOBO) using pDuraG as a template and primer pDuraSC-GAPt-F and primer URA5gDNA-F using an In-Fusion (registered trademark) Advantage PCR Cloning Kit (TaKaRa Bio Inc.) to prepare plasmid pDUra-RhG.

```
Primer hisHp + URA5-F:
                                        (SEQ ID NO: 42)
5'-GGCAAACTTGTCATGAAGCGAAAGAGAGATTATGAAAACAAGC-3'

Primer hisHp + MGt-F:
                                        (SEQ ID NO: 43)
5'-CACTCCCTTTTCTTAATTGTTGAGAGAGTGTTGGGTGAGAGT-3'

Primer pDuraSC-GAPt-F:
                                        (SEQ ID NO: 44)
5'-TAAGAAAAGGGAGTGAATCGCATAGGG-3'

Primer URA5gDNA-F:
                                        (SEQ ID NO: 45)
5'-CATGACAAGTTTGCCAAGATGCG-3'
```

A DNA fragment of about 6.3 kbp was amplified by PCR with KOD-plus-(TOYOBO) using plasmid pDUra-RhG as a template and primer pDuraSC-GAPt-F and primer pDurahG-hisp-R.

```
Primer pDurahG-hisp-R:
                                        (SEQ ID NO: 46)
5'-ATTGTTGAGAGAGTGTTGGGTGAGAGTG-3'
```

A DNA fragment of about 2.5 kbp was amplified by PCR with KOD-plus-(TOYOBO) using plasmid pCR-MaGPAT4-1 as a template and primer MaGPAT4+hisp-F and primer MaGPAT4+MGt-R.

```
Primer MaGPAT4 + hisp-F:
                                      (SEQ ID NO: 47)
5'-CACTCTCTCAACAATATGACAACCGGCGACAGTACCGC-3'

Primer MaGPAT4 + MGt-R:
                                      (SEQ ID NO: 48)
5'-CACTCCCTTTTCTTATTATAATTTCGGGGCGCCATCGC-3'
```

The resulting fragment of 2.5 kbp was linked to the above-mentioned DNA fragment of 6.3 kbp using an In-Fusion (registered trademark) Advantage PCR Cloning Kit (TaKaRaBio Inc.) to prepare plasmid pDUraRhG-GPAT4.

(2) Preparation of Transformant of *M. alpina*

Transformation was performed using a uracil auxotrophic strain Aura-3 induced from *M. alpina* strain 1S-4 in accordance with the method described in Patent Literature (WO2005/019437, Title of Invention: "Method of breeding lipid-producing fungus") as a host by a particle delivery method using plasmid pDUraRhG-GPAT4. Transformants were selected using an SC agar medium (0.5% yeast nitrogen base w/o amino acids and ammonium sulfate (Difco), 0.17% ammonium sulfate, 2% glucose, 0.002% adenine, 0.003% tyrosine, 0.0001% methionine, 0.0002% arginine, 0.0002% histidine, 0.0004% lysine, 0.0004% tryptophan, 0.0005% threonine, 0.0006% isoleucine, 0.0006% leucine, 0.0006% phenylalanine, 2% agar).

(3) Evaluation of transformed *M. alpina*

The resulting transformant was inoculated in 4 mL of a GY medium and was shake-cultured at 28° C. for 2 days. The cells were collected by filtration. RNA was extracted with an RNeasy plant kit (QIAGEN), and cDNA was synthesized with a SuperScript First-Strand system for RT-PCR (Invitrogen). In order to confirm expression of each gene from the introduced construct, RT-PCR was performed using a combination of the following primers:

```
Primer GPAT4-RT1:
                                      (SEQ ID NO: 49)
5'-GAGTGCTTCATCGAGGGCACC-3',
and Primer GPAT4-RT2:
                                      (SEQ ID NO: 50)
5'-TCCTTCACTGTCAACCTCGATCAC-3'.
```

Figure 9:
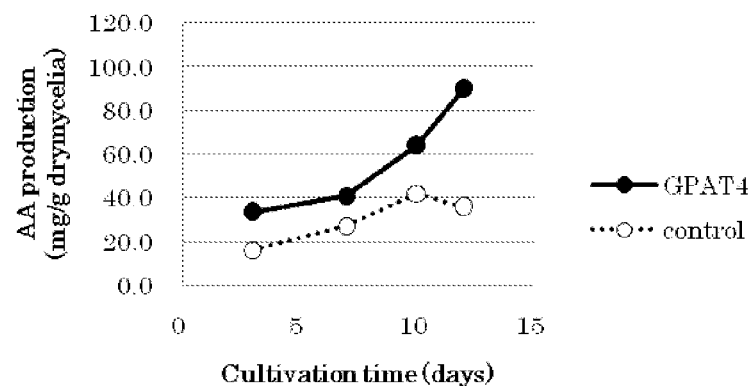
FIG. 9 is a graph showing a time-dependent change in production of arachidonic acid per dry cell weight when MaGPAT4 was overexpressed in *M. alpina*.

One of strains confirmed of overexpression was inoculated in 10 mL of a GY medium (2% glucose, 1% yeast extract) and shake-cultured at 28° C. at 300 rpm for 3 days. The whole culture solution was added to 500 mL of a GY medium (2-L Sakaguchi flask) and shake-cultured at 28° C. at 120 rpm. Five milliliters and ten milliliters of the culture solution were sampled on the third, seventh, tenth, and twelfth days and were filtered. The cells were dried at 120° C. Fatty acids were converted into methyl esters by a hydrochloric acid-methanol method and were subjected to gas chromatographic analysis of the fatty acids. A change with time in amount of arachidonic acid produced per dry cells was investigated. The host for transformation, Δura-3 strain, was used as a control. The results are shown in FIG. 9.

The amount of arachidonic acid (AA) per cells increased in *M. alpina* overexpressing GPAT4 compared with that in the control.

SEQUENCE LISTING FREE TEXT

SEQ ID NO: 16: primer GPAT4-S
SEQ ID NO: 17: primer SacI-GPAT4-1
SEQ ID NO: 18: primer Sal-GPAT4-2
SEQ ID NO: 19: primer GPAT5-1F
SEQ ID NO: 20: primer GPAT5-3R
SEQ ID NO: 26: primer Eco-MaGPAT3-F
SEQ ID NO: 27: primer Sal-MaGPAT3-R
SEQ ID NO: 28: primer Not-MaGPAT4-F1
SEQ ID NO: 29: primer Not-MaGPAT4-F2
SEQ ID NO: 30: primer Bam-MaGPAT4-R
SEQ ID NO: 31: primer Xba1-Des-SCT1-F
SEQ ID NO: 32: primer Xba1-Des-SCT1-R
SEQ ID NO: 33: primer SCT1outORF-F
SEQ ID NO: 34: primer SCT1inORF-R
SEQ ID NO: 35: primer LEU21n ORF-F
SEQ ID NO: 36: oligoDNA MCS-for-pUC18-F2
SEQ ID NO: 37: oligoDNA MCS-for-pUC18-R2
SEQ ID NO: 38: primer Not1-GAPDHt-F
SEQ ID NO: 39: primer EcoR1-Asc1-GAPDHt-R
SEQ ID NO: 40: primer URA5g-F1
SEQ ID NO: 41: primer URASg-R1
SEQ ID NO: 42: primer hisHp+URA5-F
SEQ ID NO: 43: primer hisHp+MGt-F
SEQ ID NO: 44: primer pDuraSC-GAPt-F
SEQ ID NO: 45: primer URA5gDNA-F
SEQ ID NO: 46: primer pDurahG-hisp-R
SEQ ID NO: 47: primer MaGPAT4+hisp-F
SEQ ID NO: 48: primer MaGPAT4+MGt-R
SEQ ID NO: 49: primer GPAT4-RT1
SEQ ID NO: 50: primer GPAT4-RT2

The invention claimed is:

1. A nucleic acid according to any one selected from (a) to (e) below:
- (a) a nucleic acid comprising a nucleotide sequence encoding a protein that consists of an amino acid sequence having deletion, substitution, or addition of one to 80 amino acids in the amino acid sequence set forth in SEQ ID NO: 2, SEQ ID NO: 5, or SEQ ID NO: 9 and has a glycerol 3-phosphate acyltransferase activity and/or a glycerone phosphate acyltransferase activity;
- (b) a nucleic acid comprising a nucleotide sequence that hybridizes under conditions of 2×SSC at 65° C. an washing conditions of 0.2×SSC at 65° C. with a nucleic acid consisting of a nucleotide sequence complementary to the nucleotide sequence set forth in SEQ ID NO: 1, SEQ ID NO: 4, or SEQ ID NO: 8 and encodes a protein having a glycerol 3-phosphate acyltransferase activity and/or a glycerone phosphate acyltransferase activity;
- (c) a nucleic acid comprising a nucleotide sequence that consists of a nucleotide sequence having an identity of 90% or more with the nucleotide sequence set forth in SEQ ID NO: 1, SEQ ID NO: 4, or SEQ ID NO: 8 and encodes a protein having a glycerol 3-phosphate acyltransferase activity and/or a glycerone phosphate acyltransferase activity,
(d) a nucleic acid comprising a nucleotide sequence encoding a protein that consists of an amino acid sequence having an identity of 90% or more with the amino acid sequence set forth in SEQ ID NO: 2, SEQ ID NO: 5, or SEQ ID NO: 9 and has a glycerol 3-phosphate acyltransferase activity and/or a glycerone phosphate acyltransferase activity;
(e) a nucleic acid comprising a nucleotide sequence that hybridizes under conditions of 2×SSC at 65° C. and washing conditions of 0.2×SSC at 65° C. with a nucleic acid consisting of a nucleotide sequence complementary to a nucleotide sequence encoding a protein consisting of the amino acid sequence set forth in SEQ ID NO: 2, SEQ ID NO: 5, or SEQ ID NO: 9 and encodes a protein having a glycerol 3-phosphate acyltransferase activity and/or a glycerone phosphate acyltransferase activity.

2. The nucleic acid according to claim 1, wherein the nucleic acid is any one selected from (a) to (c) below:
(a) a nucleic acid comprising a nucleotide sequence encoding a protein that consists of an amino acid sequence having deletion, substitution, or addition of 1 to 50 amino acids in the amino acid sequence set forth in SEQ ID NO: 2, SEQ ID NO: 5, or SEQ ID NO: 9 and has a glycerol 3-phosphate acyltransferase activity and/or a glycerone phosphate acyltransferase activity; and
(b) a nucleic acid comprising a nucleotide sequence that consists of a nucleotide sequence having an identity of 95% or more with the nucleotide sequence set forth in SEQ ID NO: 1, SEQ ID NO: 4, or SEQ ID NO: 8 and encodes a protein having a glycerol 3-phosphate acyltransferase activity and/or a glycerone phosphate acyltransferase activity; and
(c) a nucleic acid comprising a nucleotide sequence encoding a protein that consists of an amino acid sequence having an identity of 95% or more with the amino acid sequence set forth in SEQ ID NO: 2, SEQ ID NO: 5, or SEQ ID NO: 9 and has a glycerol 3-phosphate acyltransferase activity and/or a glycerone phosphate acyltransferase activity.

3. A nucleic acid according to any one selected from (a) to (c) below:
(a) a nucleic acid comprising the nucleotide sequence set forth in SEQ ID NO: 1, SEQ ID NO: 4, or SEQ ID NO: 8;
(b) a nucleic acid comprising a nucleotide sequence encoding a protein consisting of the amino acid sequence set forth in SEQ ID NO: 2, SEQ ID NO: 5, or SEQ ID NO: 9; and
(c) a nucleic acid comprising the nucleotide sequence set forth in SEQ ID NO: 3, SEQ ID NO: 6, or SEQ ID NO: 11.

4. A nucleic acid according to any one selected from (a) to (e) below:
(a) a nucleic acid comprising a nucleotide sequence encoding a protein that consists of an amino acid sequence having deletion, substitution, or addition of one to 80 amino acids in the amino acid sequence set forth in SEQ ID NO: 2, SEQ ID NO: 5, or SEQ ID NO: 9 and has any one of the following activities i) to v):
i) an activity to develop a fatty acid composition containing palmitic acid at a higher proportion and palmitoleic acid at a lower proportion in yeast expressing the protein compared with those in a fatty acid composition in a host not expressing the protein;
ii) an activity to generate higher contents of fatty acids in yeast expressing the protein compared with those in a host not expressing the protein;
iii) an activity to generate a higher amount of triacylglycerol (TG) in yeast expressing the protein compared with TG in a host not expressing the protein;
iv) an activity to complement glycerol 3-phosphate acyltransferase deficiency (hereinafter, also referred to as "GPAT deficiency") of yeast; and
v) an activity to increase production of arachidonic acid in a host transformed with a recombinant vector containing a nucleic acid encoding the protein compared with that in a host not transformed with the vector;
(b) a nucleic acid comprising a nucleotide sequence that hybridizes under conditions of 2×SSC at 65° C. and washing conditions of 0.2×SSC at 65° C. with a nucleic acid consisting of a nucleotide sequence complementary to the nucleotide sequence set forth in SEQ ID NO: 1, SEQ ID NO: 4, or SEQ ID NO: 8 and encodes a protein having any one of the following activities i) to v):
i) an activity to develop a fatty acid composition containing palmitic acid at a higher proportion and palmitoleic acid at a lower proportion in yeast expressing the protein compared with those in a fatty acid composition in a host not expressing the protein;
ii) an activity to generate higher contents of fatty acids in yeast expressing the protein compared with those in a host not expressing the protein;
iii) an activity to generate a higher amount of triacylglycerol (TG) in yeast expressing the protein compared with TG in a host not expressing the protein;
iv) an activity to complement GPAT deficiency of yeast; and
v) an activity to increase production of arachidonic acid in a host transformed with a recombinant vector containing a nucleic acid encoding the protein compared with that in a host not transformed with the vector;
(c) a nucleic acid comprising a nucleotide sequence that consists of a nucleotide sequence having an identity of 90% or more with the nucleotide sequence set forth in SEQ ID NO: 1, SEQ ID NO: 4, or SEQ ID NO: 8 and encodes a protein having any one of the following activities i) to v):
i) an activity to develop a fatty acid composition containing palmitic acid at a higher proportion and palmitoleic acid at a lower proportion in yeast expressing the protein compared with those in a fatty acid composition in a host not expressing the protein;
ii) an activity to generate higher contents of fatty acids in yeast expressing the protein compared with those in a host not expressing the protein;
iii) an activity to generate a higher amount of triacylglycerol (TG) in yeast expressing the protein compared with TG in a host not expressing the protein;
iv) an activity to complement GPAT deficiency of yeast; and
v) an activity to increase production of arachidonic acid in a host transformed with a recombinant vector containing a nucleic acid encoding the protein compared with that in a host not transformed with the vector;
(d) a nucleic acid comprising a nucleotide sequence encoding a protein that consists of an amino acid sequence having an identity of 90% or more with the amino acid sequence set forth in SEQ ID NO: 2, SEQ ID NO: 5, or SEQ ID NO: 9 and has any one of the following activities i) to v):
i) an activity to develop a fatty acid composition containing palmitic acid at a higher proportion and palmitoleic acid at a lower proportion in yeast expressing the protein compared with those in a fatty acid composition in a host not expressing the protein;
ii) an activity to generate higher contents of fatty acids in yeast expressing the protein compared with those in a host not expressing the protein;
iii) an activity to generate a higher amount of triacylglycerol (TG) in yeast expressing the protein compared with TG in a host not expressing the protein;
iv) an activity to complement GPAT deficiency of yeast; and
v) an activity to increase production of arachidonic acid in a host transformed with a recombinant vector containing a nucleic acid encoding the protein compared with that in a host not transformed with the vector; and
(e) a nucleic acid comprising a nucleotide sequence that hybridizes under conditions of 2×SSC at 65° C. and washing conditions of 0.2×SSC at 65° C. with a nucleic acid consisting of a nucleotide sequence complementary to a nucleotide sequence encoding a protein consisting of the amino acid sequence set forth in SEQ ID NO: 2, SEQ ID NO: 5, or SEQ ID NO: 9 and encodes a protein having any one of the following activities i) to v):
i) an activity to develop a fatty acid composition containing palmitic acid at a higher proportion and palmitoleic acid at a lower proportion in yeast expressing the protein compared with those in a fatty acid composition in a host not expressing the protein;
ii) an activity to generate higher contents of fatty acids in yeast expressing the protein compared with those in a host not expressing the protein;
iii) an activity to generate a higher amount of triacylglycerol (TG) in yeast expressing the protein compared with TG in a host not expressing the protein;
iv) an activity to complement GPAT deficiency of yeast; and
v) an activity to increase production of arachidonic acid in a host transformed with a recombinant vector containing a nucleic acid encoding the protein compared with that in a host not transformed with the vector.

5. The nucleic acid according to claim 4, wherein the nucleic acid is any one selected from (a) to (c) below:
(a) a nucleic acid comprising a nucleotide sequence including an exon encoding a protein that consists of an amino acid sequence having deletion, substitution, or addition of 1 to 50 amino acids in the amino acid sequence set forth in SEQ ID NO: 2, SEQ ID NO: 5, or SEQ ID NO: 9 and has any one of the following activities i) to v):
i) an activity to develop a fatty acid composition containing palmitic acid at a higher proportion and palmitoleic acid at a lower proportion in yeast expressing the protein compared with those in a fatty acid composition in a host not expressing the protein;
ii) an activity to generate higher contents of fatty acids in yeast expressing the protein compared with those in a host not expressing the protein;
iii) an activity to generate a higher amount of triacylglycerol (TG) in yeast expressing the protein compared with TG in a host not expressing the protein;
iv) an activity to complement GPAT deficiency of yeast; and
v) an activity to increase production of arachidonic acid in a host transformed with a recombinant vector containing a nucleic acid encoding the protein compared with that in a host not transformed with the vector;
(b) a nucleic acid comprising a nucleotide sequence that has an identity of 95% or more with the nucleotide sequence set forth in SEQ ID NO: 1, SEQ ID NO: 4, or SEQ ID NO: 8 and includes an exon encoding a protein having any one of the following activities i) to v):
i) an activity to develop a fatty acid composition containing palmitic acid at a higher proportion and palmitoleic acid at a lower proportion in yeast expressing the protein compared with those in a fatty acid composition in a host not expressing the protein;
ii) an activity to generate higher contents of fatty acids in yeast expressing the protein compared with those in a host not expressing the protein;
iii) an activity to generate a higher amount of triacylglycerol (TG) in yeast expressing the protein compared with TG in a host not expressing the protein;
iv) an activity to complement GPAT deficiency of yeast; and
v) an activity to increase production of arachidonic acid in a host transformed with a recombinant vector containing a nucleic acid encoding the protein compared with that in a host not transformed with the vector; and
(c) a nucleic acid comprising a nucleotide sequence that includes an exon encoding a protein that consists of an amino acid sequence having an identity of 95% or more with the amino acid sequence set forth in SEQ ID NO: 2, SEQ ID NO: 5, or SEQ ID NO: 9 and has any one of the following activities i) to v):
i) an activity to develop a fatty acid composition containing palmitic acid at a higher proportion and palmitoleic acid at a lower proportion in yeast expressing the protein compared with those in a fatty acid composition in a host not expressing the protein;
ii) an activity to generate higher contents of fatty acids in yeast expressing the protein compared with those in a host not expressing the protein;
iii) an activity to generate a higher amount of triacylglycerol (TG) in yeast expressing the protein compared with TG in a host not expressing the protein;
iv) an activity to complement GPAT deficiency of yeast; and
v) an activity to increase production of arachidonic acid in a host transformed with a recombinant vector containing a nucleic acid encoding the protein compared with that in a host not transformed with the vector.

6. A recombinant vector comprising the nucleic acid according to claim 1.

7. A transformant transformed with the recombinant vector according to claim 6.

8. A method of producing a fatty acid composition, comprising collecting a fatty acid or a lipid from a culture obtained by culturing the transformant according to claim 7.

* * * * *

UNITED STATES PATENT AND TRADEMARK OFFICE
CERTIFICATE OF CORRECTION

Page 1 of 1

PATENT NO. : 9,163,291 B2
APPLICATION NO. : 13/575700
DATED : October 20, 2015
INVENTOR(S) : M. Ochiai It is certified that error appears in the above-identified patent and that said Letters Patent is hereby corrected as shown below:

Claims

In column 134, lines 59-60 (claim 1, lines 11-12) please change "65° C. an washing" to -- 65° C. and washing --.

In column 135, line 12 (claim 1, line 31) please change "activity," to -- activity; and --.

In column 135, line 31 (claim 2, line 9) please change "activity; and" to -- activity; --.

Signed and Sealed this
Twenty-fourth Day of May, 2016

Michelle K. Lee
*Director of the United States Patent and Trademark Office*

```
                        SEQUENCE LISTING

<160> NUMBER OF SEQ ID NOS: 50

<210> SEQ ID NO 1
<211> LENGTH: 2475
<212> TYPE: DNA
<213> ORGANISM: Mortierella alpina
<220> FEATURE:
<221> NAME/KEY: CDS
<222> LOCATION: (1)..(2475)
<223> OTHER INFORMATION:

<400> SEQUENCE: 1 atg ccc atc gtt cca gct cag caa gtc gac tcc tcc tcg tgc cct ccc        48
Met Pro Ile Val Pro Ala Gln Gln Val Asp Ser Ser Ser Cys Pro Pro
1               5                  10                  15 tct ggt gaa tct agc ccg ttg att ccc agt ttg ggc gaa gga gtg cat        96
Ser Gly Glu Ser Ser Pro Leu Ile Pro Ser Leu Gly Glu Gly Val His
```

```
            20                  25                  30
tcg ggt cat gga cac gtt gtc gac aat gac gag tcc ggc gtg gag aac    144
Ser Gly His Gly His Val Val Asp Asn Asp Glu Ser Gly Val Glu Asn
         35                  40                  45 att acc aaa aag cac gca gga cga att aga gaa gat ccg gtc ggc ttc    192
Ile Thr Lys Lys His Ala Gly Arg Ile Arg Glu Asp Pro Val Gly Phe
 50                  55                  60 gtg gtg cag act gca gct ttc tat cag ggc acg ggt tgg aga agc tac    240
Val Val Gln Thr Ala Ala Phe Tyr Gln Gly Thr Gly Trp Arg Ser Tyr
 65                  70                  75                  80 agc aac tat gtt gga acg cgc att ctt tac gaa ggc ttc tct gca acc    288
Ser Asn Tyr Val Gly Thr Arg Ile Leu Tyr Glu Gly Phe Ser Ala Thr
                 85                  90                  95 ttc aag gag cga att ctc gcc agt tca aaa gtg aat gat ctc atc aag    336
Phe Lys Glu Arg Ile Leu Ala Ser Ser Lys Val Asn Asp Leu Ile Lys
            100                 105                 110 gac atg gcc aac aag cag ttg gat gtc ctg atc aag caa aga caa gat    384
Asp Met Ala Asn Lys Gln Leu Asp Val Leu Ile Lys Gln Arg Gln Asp
        115                 120                 125 gcg tat gac gca gag agg act gca aat gca gga aaa aag aac ttc aag    432
Ala Tyr Asp Ala Glu Arg Thr Ala Asn Ala Gly Lys Lys Asn Phe Lys
130                 135                 140 ccc aaa gtt cga ctc ctt cgc cca gaa gat atc gag gct cgt cgc aaa    480
Pro Lys Val Arg Leu Leu Arg Pro Glu Asp Ile Glu Ala Arg Arg Lys
145                 150                 155                 160 aca tta gaa gcc gag ctt gtt gcg gtg gca aag tca aat atc gac aaa    528
Thr Leu Glu Ala Glu Leu Val Ala Val Ala Lys Ser Asn Ile Asp Lys
                165                 170                 175 ctt gtt tgt gat atg aac agt atg aaa ttc atc agg ttc ttc gcc ttc    576
Leu Val Cys Asp Met Asn Ser Met Lys Phe Ile Arg Phe Phe Ala Phe
            180                 185                 190 ctc atc aac aac atc ctt gtg aga atg tac cat caa gga att cac atc    624
Leu Ile Asn Asn Ile Leu Val Arg Met Tyr His Gln Gly Ile His Ile
        195                 200                 205 aag gag tcc gag ttc ttg gag ctg cgg agg ata gct gag tac tgc gca    672
Lys Glu Ser Glu Phe Leu Glu Leu Arg Arg Ile Ala Glu Tyr Cys Ala
210                 215                 220 gag aaa aag tat tcg atg gtg gtg ttg cca tgc cac aag tca cac atc    720
Glu Lys Lys Tyr Ser Met Val Val Leu Pro Cys His Lys Ser His Ile
225                 230                 235                 240 gac tac ctc gtc gtc tcg tac att ttc ttc cgc atg gga tta gct tta    768
Asp Tyr Leu Val Val Ser Tyr Ile Phe Phe Arg Met Gly Leu Ala Leu
                245                 250                 255 cct cac att gct gct ggc gat aac ctg gac atg ccc att gtc gga aag    816
Pro His Ile Ala Ala Gly Asp Asn Leu Asp Met Pro Ile Val Gly Lys
            260                 265                 270 gca ctc aaa gga gca ggc gcg ttc ttc att cgc cgt tct tgg gct gac    864
Ala Leu Lys Gly Ala Gly Ala Phe Phe Ile Arg Arg Ser Trp Ala Asp
        275                 280                 285 gat caa ctt tac acc agc att gtt cag gaa tat gtt cag gag ctt ttg    912
Asp Gln Leu Tyr Thr Ser Ile Val Gln Glu Tyr Val Gln Glu Leu Leu
290                 295                 300 gag gga gga tac aat atc gag tgc ttc atc gag ggc acc cga agc aga    960
Glu Gly Gly Tyr Asn Ile Glu Cys Phe Ile Glu Gly Thr Arg Ser Arg
305                 310                 315                 320 aca gga aaa ctt ttg cca cca aag ctg gga gtc cta aag att atc atg   1008
Thr Gly Lys Leu Leu Pro Pro Lys Leu Gly Val Leu Lys Ile Ile Met
                325                 330                 335 gat gct atg ctt tcg aac cgc atc caa gac tgc tac atc gtg ccc atc   1056
```

```
                                    -continued

Asp Ala Met Leu Ser Asn Arg Ile Gln Asp Cys Tyr Ile Val Pro Ile
        340                 345                 350 tct atc ggt tat gac aag gtc atc gaa acc gag act tat atc aat gag     1104
Ser Ile Gly Tyr Asp Lys Val Ile Glu Thr Glu Thr Tyr Ile Asn Glu
            355                 360                 365 ctt ctc gga atc ccc aag gaa aag gag agt ttg tgg ggt gtt att acg     1152
Leu Leu Gly Ile Pro Lys Glu Lys Glu Ser Leu Trp Gly Val Ile Thr
370                 375                 380 aat tcg agg ctg ctc cag ctc aag atg ggc cgc att gat gtc cga ttt     1200
Asn Ser Arg Leu Leu Gln Leu Lys Met Gly Arg Ile Asp Val Arg Phe
385                 390                 395                 400 gca aag ccg tac agt ttg cga aac ttt atg aat cat gag atc gag cgc     1248
Ala Lys Pro Tyr Ser Leu Arg Asn Phe Met Asn His Glu Ile Glu Arg
                405                 410                 415 aga gag atc atc aat aag cgg gaa gac acc gat agt gtg gcg aaa tct     1296
Arg Glu Ile Ile Asn Lys Arg Glu Asp Thr Asp Ser Val Ala Lys Ser
            420                 425                 430 cag ctg cta aag gca ttg ggc tac aag gtc ttg gca gac atc aac tcg     1344
Gln Leu Leu Lys Ala Leu Gly Tyr Lys Val Leu Ala Asp Ile Asn Ser
        435                 440                 445 gtc tct gta gta atg ccc acg gcc ctc gtg ggt act gtc atc ctt aca     1392
Val Ser Val Val Met Pro Thr Ala Leu Val Gly Thr Val Ile Leu Thr
450                 455                 460 ctc cga gga cga ggt gtt ggc cgt aat gag ctg atc cgt cgt gtt gag     1440
Leu Arg Gly Arg Gly Val Gly Arg Asn Glu Leu Ile Arg Arg Val Glu
465                 470                 475                 480 tgg ctg aag cgc gag att ctt tcc aag ggt ggt cgc gtt gcc aac ttt     1488
Trp Leu Lys Arg Glu Ile Leu Ser Lys Gly Gly Arg Val Ala Asn Phe
                485                 490                 495 agc ggg atg gaa act ggc gag gtt gta gat cga gca ttg ggc gtt ctt     1536
Ser Gly Met Glu Thr Gly Glu Val Val Asp Arg Ala Leu Gly Val Leu
            500                 505                 510 aag gac ctt gtg gcg ctg cag aag aat ttg ctc gag ccc gtc ttc tat     1584
Lys Asp Leu Val Ala Leu Gln Lys Asn Leu Leu Glu Pro Val Phe Tyr
        515                 520                 525 gcg gtc aag cgc ttc gag ctt tcg ttc tac agg aat cag ctc atc cac     1632
Ala Val Lys Arg Phe Glu Leu Ser Phe Tyr Arg Asn Gln Leu Ile His
530                 535                 540 ctc ttt gtc cat gag gcc atc atc gcc gtg acg atg tac acc cgc atc     1680
Leu Phe Val His Glu Ala Ile Ile Ala Val Thr Met Tyr Thr Arg Ile
545                 550                 555                 560 aag att ggt ggc gcc aag tct aca caa cac att agt cag aat gag ctg     1728
Lys Ile Gly Gly Ala Lys Ser Thr Gln His Ile Ser Gln Asn Glu Leu
                565                 570                 575 ctg aac gag gtc acc ttc ctg agc cgc ctg ctc aag acc gac ttt atc     1776
Leu Asn Glu Val Thr Phe Leu Ser Arg Leu Leu Lys Thr Asp Phe Ile
            580                 585                 590 tac aac cct ggc gat att gag agt aac ttg gag cat aca ttg gat tac     1824
Tyr Asn Pro Gly Asp Ile Glu Ser Asn Leu Glu His Thr Leu Asp Tyr
        595                 600                 605 ctc aag aaa tcc aat gtg atc gag gtt gac agt gaa gga tat gtc gga     1872
Leu Lys Lys Ser Asn Val Ile Glu Val Asp Ser Glu Gly Tyr Val Gly
610                 615                 620 ctc tct gat gct gaa cgc agc aag ggc cga gag aac tat gac ttt tat     1920
Leu Ser Asp Ala Glu Arg Ser Lys Gly Arg Glu Asn Tyr Asp Phe Tyr
625                 630                 635                 640 tgt ttc ctg ctc tgg ccc ttc gtg gag aca tac tgg ctc gca gcc gtg     1968
Cys Phe Leu Leu Trp Pro Phe Val Glu Thr Tyr Trp Leu Ala Ala Val
                645                 650                 655
```

```
tcc ctg tat acc ctg att ccc acc gcc aaa gag ttg act cag cag ttg      2016
Ser Leu Tyr Thr Leu Ile Pro Thr Ala Lys Glu Leu Thr Gln Gln Leu
            660                 665                 670 gac agc aac gga gag cct cag gtt cac tgg gtt gag gag cgc gtg ttc      2064
Asp Ser Asn Gly Glu Pro Gln Val His Trp Val Glu Glu Arg Val Phe
        675                 680                 685 atg gag aag acg caa atg ttc gga aag acg ctt tac tac cag gga gac      2112
Met Glu Lys Thr Gln Met Phe Gly Lys Thr Leu Tyr Tyr Gln Gly Asp
690                 695                 700 ctc tcc tac ttt gag tct gtc aac atg gag acg ctc aag aat ggt ttt      2160
Leu Ser Tyr Phe Glu Ser Val Asn Met Glu Thr Leu Lys Asn Gly Phe
705                 710                 715                 720 aat cgt ctg tgc gat tat ggc atc ctt atg atg aag cga ccc acc aat      2208
Asn Arg Leu Cys Asp Tyr Gly Ile Leu Met Met Lys Arg Pro Thr Asn
            725                 730                 735 gcc aag gag aag aca aag gtt gct ctc cac cct gat ttt atg cca agc      2256
Ala Lys Glu Lys Thr Lys Val Ala Leu His Pro Asp Phe Met Pro Ser
        740                 745                 750 cga ggt gct gac ggt cat gtc att gcc agc ggc gca ctt tgg gat atg      2304
Arg Gly Ala Asp Gly His Val Ile Ala Ser Gly Ala Leu Trp Asp Met
    755                 760                 765 gtc gaa cat atc ggc acg ttc aga cgt gaa ggc aag aat cgt cgt gat      2352
Val Glu His Ile Gly Thr Phe Arg Arg Glu Gly Lys Asn Arg Arg Asp
770                 775                 780 aac gcc aca gtt tcc tcc cgt gtc ctg cgg ttt gca gag gtc gtc gcg      2400
Asn Ala Thr Val Ser Ser Arg Val Leu Arg Phe Ala Glu Val Val Ala
785                 790                 795                 800 aac gct cca gct ccg gtt aag gta ccc ttg ccc aat ccg gca ccc aaa      2448
Asn Ala Pro Ala Pro Val Lys Val Pro Leu Pro Asn Pro Ala Pro Lys
            805                 810                 815 agg aca ggc gat ggc gcc ccg aaa tta                                  2475
Arg Thr Gly Asp Gly Ala Pro Lys Leu
        820                 825

<210> SEQ ID NO 2
<211> LENGTH: 825
<212> TYPE: PRT
<213> ORGANISM: Mortierella alpina

<400> SEQUENCE: 2

Met Pro Ile Val Pro Ala Gln Gln Val Asp Ser Ser Cys Pro Pro
1               5                   10                  15

Ser Gly Glu Ser Ser Pro Leu Ile Pro Ser Leu Gly Glu Gly Val His
                20                  25                  30

Ser Gly His Gly His Val Val Asp Asn Asp Glu Ser Gly Val Glu Asn
            35                  40                  45

Ile Thr Lys Lys His Ala Gly Arg Ile Arg Glu Asp Pro Val Gly Phe
        50                  55                  60

Val Val Gln Thr Ala Ala Phe Tyr Gln Gly Thr Gly Trp Arg Ser Tyr
65                  70                  75                  80

Ser Asn Tyr Val Gly Thr Arg Ile Leu Tyr Glu Gly Phe Ser Ala Thr
                85                  90                  95

Phe Lys Glu Arg Ile Leu Ala Ser Ser Lys Val Asn Asp Leu Ile Lys
            100                 105                 110

Asp Met Ala Asn Lys Gln Leu Asp Val Leu Ile Lys Gln Arg Gln Asp
        115                 120                 125

Ala Tyr Asp Ala Glu Arg Thr Ala Asn Ala Gly Lys Lys Asn Phe Lys
    130                 135                 140
```

-continued

```
Pro Lys Val Arg Leu Leu Arg Pro Glu Asp Ile Glu Ala Arg Arg Lys
145                 150                 155                 160

Thr Leu Glu Ala Glu Leu Val Ala Val Ala Lys Ser Asn Ile Asp Lys
            165                 170                 175

Leu Val Cys Asp Met Asn Ser Met Lys Phe Ile Arg Phe Phe Ala Phe
        180                 185                 190

Leu Ile Asn Asn Ile Leu Val Arg Met Tyr His Gln Gly Ile His Ile
    195                 200                 205

Lys Glu Ser Glu Phe Leu Glu Leu Arg Arg Ile Ala Glu Tyr Cys Ala
210                 215                 220

Glu Lys Lys Tyr Ser Met Val Val Leu Pro Cys His Lys Ser His Ile
225                 230                 235                 240

Asp Tyr Leu Val Val Ser Tyr Ile Phe Phe Arg Met Gly Leu Ala Leu
            245                 250                 255

Pro His Ile Ala Ala Gly Asp Asn Leu Asp Met Pro Ile Val Gly Lys
        260                 265                 270

Ala Leu Lys Gly Ala Gly Ala Phe Phe Ile Arg Arg Ser Trp Ala Asp
    275                 280                 285

Asp Gln Leu Tyr Thr Ser Ile Val Gln Glu Tyr Val Gln Glu Leu Leu
290                 295                 300

Glu Gly Gly Tyr Asn Ile Glu Cys Phe Ile Glu Gly Thr Arg Ser Arg
305                 310                 315                 320

Thr Gly Lys Leu Leu Pro Pro Lys Leu Gly Val Leu Lys Ile Ile Met
            325                 330                 335

Asp Ala Met Leu Ser Asn Arg Ile Gln Asp Cys Tyr Ile Val Pro Ile
        340                 345                 350

Ser Ile Gly Tyr Asp Lys Val Ile Glu Thr Glu Thr Tyr Ile Asn Glu
    355                 360                 365

Leu Leu Gly Ile Pro Lys Glu Lys Glu Ser Leu Trp Gly Val Ile Thr
370                 375                 380

Asn Ser Arg Leu Leu Gln Leu Lys Met Gly Arg Ile Asp Val Arg Phe
385                 390                 395                 400

Ala Lys Pro Tyr Ser Leu Arg Asn Phe Met Asn His Glu Ile Glu Arg
            405                 410                 415

Arg Glu Ile Ile Asn Lys Arg Glu Asp Thr Asp Ser Val Ala Lys Ser
        420                 425                 430

Gln Leu Leu Lys Ala Leu Gly Tyr Lys Val Leu Ala Asp Ile Asn Ser
    435                 440                 445

Val Ser Val Val Met Pro Thr Ala Leu Val Gly Thr Val Ile Leu Thr
450                 455                 460

Leu Arg Gly Arg Gly Val Gly Arg Asn Glu Leu Ile Arg Arg Val Glu
465                 470                 475                 480

Trp Leu Lys Arg Glu Ile Leu Ser Lys Gly Gly Arg Val Ala Asn Phe
            485                 490                 495

Ser Gly Met Glu Thr Gly Glu Val Asp Arg Ala Leu Gly Val Leu
        500                 505                 510

Lys Asp Leu Val Ala Leu Gln Lys Asn Leu Leu Glu Pro Val Phe Tyr
    515                 520                 525

Ala Val Lys Arg Phe Glu Leu Ser Phe Tyr Arg Asn Gln Leu Ile His
530                 535                 540

Leu Phe Val His Glu Ala Ile Ile Ala Val Thr Met Tyr Thr Arg Ile
545                 550                 555                 560

Lys Ile Gly Gly Ala Lys Ser Thr Gln His Ile Ser Gln Asn Glu Leu
```

```
                          565                 570                 575
Leu Asn Glu Val Thr Phe Leu Ser Arg Leu Leu Lys Thr Asp Phe Ile
                580                 585                 590

Tyr Asn Pro Gly Asp Ile Glu Ser Asn Leu Glu His Thr Leu Asp Tyr
            595                 600                 605

Leu Lys Lys Ser Asn Val Ile Glu Val Asp Ser Glu Gly Tyr Val Gly
        610                 615                 620

Leu Ser Asp Ala Glu Arg Ser Lys Gly Arg Glu Asn Tyr Asp Phe Tyr
625                 630                 635                 640

Cys Phe Leu Leu Trp Pro Phe Val Glu Thr Tyr Trp Leu Ala Ala Val
                645                 650                 655

Ser Leu Tyr Thr Leu Ile Pro Thr Ala Lys Glu Leu Thr Gln Gln Leu
                660                 665                 670

Asp Ser Asn Gly Glu Pro Gln Val His Trp Val Glu Glu Arg Val Phe
            675                 680                 685

Met Glu Lys Thr Gln Met Phe Gly Lys Thr Leu Tyr Tyr Gln Gly Asp
        690                 695                 700

Leu Ser Tyr Phe Glu Ser Val Asn Met Glu Thr Leu Lys Asn Gly Phe
705                 710                 715                 720

Asn Arg Leu Cys Asp Tyr Gly Ile Leu Met Met Lys Arg Pro Thr Asn
                725                 730                 735

Ala Lys Glu Lys Thr Lys Val Ala Leu His Pro Asp Phe Met Pro Ser
                740                 745                 750

Arg Gly Ala Asp Gly His Val Ile Ala Ser Gly Ala Leu Trp Asp Met
            755                 760                 765

Val Glu His Ile Gly Thr Phe Arg Arg Glu Gly Lys Asn Arg Arg Asp
        770                 775                 780

Asn Ala Thr Val Ser Ser Arg Val Leu Arg Phe Ala Glu Val Val Ala
785                 790                 795                 800

Asn Ala Pro Ala Pro Val Lys Val Pro Leu Pro Asn Pro Ala Pro Lys
                805                 810                 815

Arg Thr Gly Asp Gly Ala Pro Lys Leu
            820                 825

<210> SEQ ID NO 3
<211> LENGTH: 2478
<212> TYPE: DNA
<213> ORGANISM: Mortierella alpina

<400> SEQUENCE: 3
atgcccatcg ttccagctca gcaagtcgac tcctcctcgt gccctccctc tggtgaatct     60
agcccgttga ttcccagttt gggcgaagga gtgcattcgg tcatggaca  cgttgtcgac    120 aatgacgagt ccggcgtgga gaacattacc aaaaagcacg caggacgaat tagagaagat    180
ccggtcggct tcgtggtgca gactgcagct ttctatcagg gcacggggtt gagaagctac    240
agcaactatg ttggaacgcg cattctttac gaaggcttct ctgcaaccct caaggagcga    300
attctcgcca gttcaaaagt gaatgatctc atcaaggaca tggccaacaa gcagttggat    360
gtcctgatca gcaaagaca  agatgcgtat gacgcagaga ggactgcaaa tgcaggaaaa    420
aagaacttca gcccaaagt  tcgactcctt cgcccagaag atatcgaggc tcgtcgcaaa    480
acattagaag ccgagcttgt tgcggtggca aagtcaaata tcgacaaact tgtttgtgat    540
atgaacagta tgaaattcat caggttcttc gccttcctca tcaacaacat ccttgtgaga    600
atgtaccatc aaggaattca catcaaggag tccgagttct tggagctgcg gaggatagct    660
```

```
gagtactgcg cagagaaaaa gtattcgatg gtggtgttgc catgccacaa gtcacacatc      720
gactacctcg tcgtctcgta cattttcttc cgcatgggat tagctttacc tcacattgct      780
gctggcgata acctggacat gcccattgtc ggaaaggcac tcaaaggagc aggcgcgttc      840
ttcattcgcc gttcttgggc tgacgatcaa ctttacacca gcattgttca ggaatatgtt      900
caggagcttt tggagggagg atacaatatc gagtgcttca tcgagggcac ccgaagcaga      960
acaggaaaac ttttgccacc aaagctggga gtcctaaaga ttatcatgga tgctatgctt     1020
tcgaaccgca tccaagactg ctacatcgtg cccatctcta tcggttatga caaggtcatc     1080
gaaaccgaga cttatatcaa tgagcttctc ggaatcccca aggaaaagga gagtttgtgg     1140
ggtgttatta cgaattcgag gctgctccag ctcaagatgg gccgcattga tgtccgattt     1200
gcaaagccgt acagtttgcg aaactttatg aatcatgaga tcgagcgcag agagatcatc     1260
aataagcggg aagacaccga tagtgtggcg aaatctcagc tgctaaaggc attgggctac     1320
aaggtcttgg cagacatcaa ctcggtctct gtagtaatgc ccacggccct cgtgggtact     1380
gtcatcctta cactccgagg acgaggtgtt ggccgtaatg agctgatccg tcgtgttgag     1440
tggctgaagc gcgagattct ttccaagggt ggtcgcgttg ccaactttag cgggatggaa     1500
actggcgagg ttgtagatcg agcattgggc gttcttaagg accttgtggc gctgcagaag     1560
aatttgctcg agcccgtctt ctatgcggtc aagcgcttcg agctttcgtt ctacaggaat     1620
cagctcatcc acctctttgt ccatgaggcc atcatcgccg tgacgatgta cacccgcatc     1680
aagattggtg cgccaagtc tacacaacac attagtcaga atgagctgct gaacgaggtc      1740
accttcctga gccgcctgct caagaccgac tttatctaca accctggcga tattgagagt     1800
aacttggagc atacattgga ttacctcaag aaatccaatg tgatcgaggt tgacagtgaa     1860
ggatatgtcg gactctctga tgctgaacgc agcaagggcc gagagaacta tgactttat      1920 tgtttcctgc tctggccctt cgtggagaca tactggctcg cagccgtgtc cctgtatacc     1980
ctgattccca ccgccaaaga gttgactcag cagttggaca gcaacggaga gcctcaggtt     2040
cactgggttg aggagcgcgt gttcatggag aagacgcaaa tgttcggaaa gacgctttac     2100
taccagggag acctctccta ctttgagtct gtcaacatgg agacgctcaa gaatggtttt     2160
aatcgtctgt gcgattatgg catccttatg atgaagcgac ccaccaatgc caaggagaag     2220
acaaaggttg ctctccaccc tgattttatg ccaagccgag gtgctgacgg tcatgtcatt     2280
gccagcggcg cactttggga tatggtcgaa catatcggca cgttcagacg tgaaggcaag     2340
aatcgtcgtg ataacgccac agtttcctcc cgtgtcctgc ggtttgcaga ggtcgtcgcg     2400
aacgctccag ctccggttaa ggtaccttg cccaatccgg cacccaaaag gacaggcgat      2460
ggcgccccga aattataa                                                  2478
```

<210> SEQ ID NO 4
<211> LENGTH: 2643
<212> TYPE: DNA
<213> ORGANISM: Mortierella alpina
<220> FEATURE:
<221> NAME/KEY: CDS
<222> LOCATION: (1)..(2643)
<223> OTHER INFORMATION:

<400> SEQUENCE: 4

```
atg aca acc ggc gac agt acc gct gct gac ggt agc agc agc agt agc        48
Met Thr Thr Gly Asp Ser Thr Ala Ala Asp Gly Ser Ser Ser Ser Ser
1               5                   10                  15
```

|     |     |     |     |     |     |     |     |     |     |     |     |     |     |     |     |     |
|---|---|---|---|---|---|---|---|---|---|---|---|---|---|---|---|---|
| agc | aac | aac | agc | acc | aac | att | gcc | agt | act | agt | aac | ggc | aag | gct | gct | 96 |
| Ser | Asn | Asn | Ser | Thr | Asn | Ile | Ala | Ser | Thr | Ser | Asn | Gly | Lys | Ala | Ala | |
| | | | 20 | | | | 25 | | | | | 30 | | | | |
| ccc | cac | cca | ctc | caa | ggg | gga | tca | ccc | gct | cct | gta | gct | cca | gtt | ttg | 144 |
| Pro | His | Pro | Leu | Gln | Gly | Gly | Ser | Pro | Ala | Pro | Val | Ala | Pro | Val | Leu | |
| | | 35 | | | | | 40 | | | | | 45 | | | | |
| gaa | ttg | aag | cct | ctc | aag | aat | gtt | atg | ccc | atc | gtt | cca | gct | cag | caa | 192 |
| Glu | Leu | Lys | Pro | Leu | Lys | Asn | Val | Met | Pro | Ile | Val | Pro | Ala | Gln | Gln | |
| | 50 | | | | | 55 | | | | | 60 | | | | | |
| gtc | gac | tcc | tcc | tcg | tgc | cct | ccc | tct | ggt | gaa | tct | agc | ccg | ttg | att | 240 |
| Val | Asp | Ser | Ser | Ser | Cys | Pro | Pro | Ser | Gly | Glu | Ser | Ser | Pro | Leu | Ile | |
| 65 | | | | | 70 | | | | | 75 | | | | | 80 | |
| ccc | agt | ttg | ggc | gaa | gga | gtg | cat | tcg | ggt | cat | gga | cac | gtt | gtc | gac | 288 |
| Pro | Ser | Leu | Gly | Glu | Gly | Val | His | Ser | Gly | His | Gly | His | Val | Val | Asp | |
| | | | | 85 | | | | | 90 | | | | | 95 | | |
| aat | gac | gag | tcc | ggc | gtg | gag | aac | att | acc | aaa | aag | cac | gca | gga | cga | 336 |
| Asn | Asp | Glu | Ser | Gly | Val | Glu | Asn | Ile | Thr | Lys | Lys | His | Ala | Gly | Arg | |
| | | | | 100 | | | | | 105 | | | | | 110 | | |
| att | aga | gaa | gat | ccg | gtc | ggc | ttc | gtg | gtg | cag | act | gca | gct | ttc | tat | 384 |
| Ile | Arg | Glu | Asp | Pro | Val | Gly | Phe | Val | Val | Gln | Thr | Ala | Ala | Phe | Tyr | |
| | | | 115 | | | | | 120 | | | | | 125 | | | |
| cag | ggc | acg | ggt | tgg | aga | agc | tac | agc | aac | tat | gtt | gga | acg | cgc | att | 432 |
| Gln | Gly | Thr | Gly | Trp | Arg | Ser | Tyr | Ser | Asn | Tyr | Val | Gly | Thr | Arg | Ile | |
| | 130 | | | | | 135 | | | | | 140 | | | | | |
| ctt | tac | gaa | ggc | ttc | tct | gca | acc | ttc | aag | gag | cga | att | ctc | gcc | agt | 480 |
| Leu | Tyr | Glu | Gly | Phe | Ser | Ala | Thr | Phe | Lys | Glu | Arg | Ile | Leu | Ala | Ser | |
| 145 | | | | | 150 | | | | | 155 | | | | | 160 | |
| tca | aaa | gtg | aat | gat | ctc | atc | aag | gac | atg | gcc | aac | aag | cag | ttg | gat | 528 |
| Ser | Lys | Val | Asn | Asp | Leu | Ile | Lys | Asp | Met | Ala | Asn | Lys | Gln | Leu | Asp | |
| | | | | 165 | | | | | 170 | | | | | 175 | | |
| gtc | ctg | atc | aag | caa | aga | caa | gat | gcg | tat | gac | gca | gag | agg | act | gca | 576 |
| Val | Leu | Ile | Lys | Gln | Arg | Gln | Asp | Ala | Tyr | Asp | Ala | Glu | Arg | Thr | Ala | |
| | | | 180 | | | | | 185 | | | | | 190 | | | |
| aat | gca | gga | aaa | aag | aac | ttc | aag | ccc | aaa | gtt | cga | ctc | ctt | cgc | cca | 624 |
| Asn | Ala | Gly | Lys | Lys | Asn | Phe | Lys | Pro | Lys | Val | Arg | Leu | Leu | Arg | Pro | |
| | 195 | | | | | 200 | | | | | 205 | | | | | |
| gaa | gat | atc | gag | gct | cgt | cgc | aaa | aca | tta | gaa | gcc | gag | ctt | gtt | gcg | 672 |
| Glu | Asp | Ile | Glu | Ala | Arg | Arg | Lys | Thr | Leu | Glu | Ala | Glu | Leu | Val | Ala | |
| 210 | | | | | 215 | | | | | 220 | | | | | | |
| gtg | gca | aag | tca | aat | atc | gac | aaa | ctt | gtt | tgt | gat | atg | aac | agt | atg | 720 |
| Val | Ala | Lys | Ser | Asn | Ile | Asp | Lys | Leu | Val | Cys | Asp | Met | Asn | Ser | Met | |
| 225 | | | | 230 | | | | | 235 | | | | | 240 | | |
| aaa | ttc | atc | agg | ttc | ttc | gcc | ttc | ctc | atc | aac | aac | atc | ctt | gtg | aga | 768 |
| Lys | Phe | Ile | Arg | Phe | Phe | Ala | Phe | Leu | Ile | Asn | Asn | Ile | Leu | Val | Arg | |
| | | | 245 | | | | | 250 | | | | | 255 | | | |
| atg | tac | cat | caa | gga | att | cac | atc | aag | gag | tcc | gag | ttc | ttg | gag | ctg | 816 |
| Met | Tyr | His | Gln | Gly | Ile | His | Ile | Lys | Glu | Ser | Glu | Phe | Leu | Glu | Leu | |
| | | 260 | | | | | 265 | | | | | 270 | | | | |
| cgg | agg | ata | gct | gag | tac | tgc | gca | gag | aaa | aag | tat | tcg | atg | gtg | gtg | 864 |
| Arg | Arg | Ile | Ala | Glu | Tyr | Cys | Ala | Glu | Lys | Lys | Tyr | Ser | Met | Val | Val | |
| | 275 | | | | | 280 | | | | | 285 | | | | | |
| ttg | cca | tgc | cac | aag | tca | cac | atc | gac | tac | ctc | gtc | gtc | tcg | tac | att | 912 |
| Leu | Pro | Cys | His | Lys | Ser | His | Ile | Asp | Tyr | Leu | Val | Val | Ser | Tyr | Ile | |
| 290 | | | | | 295 | | | | | 300 | | | | | | |
| ttc | ttc | cgc | atg | gga | tta | gct | tta | cct | cac | att | gct | gct | ggc | gat | aac | 960 |
| Phe | Phe | Arg | Met | Gly | Leu | Ala | Leu | Pro | His | Ile | Ala | Ala | Gly | Asp | Asn | |
| 305 | | | | 310 | | | | | 315 | | | | | 320 | | |
| ctg | gac | atg | ccc | att | gtc | gga | aag | gca | ctc | aaa | gga | gca | ggc | gcg | ttc | 1008 |
| Leu | Asp | Met | Pro | Ile | Val | Gly | Lys | Ala | Leu | Lys | Gly | Ala | Gly | Ala | Phe | |
| | | | 325 | | | | | 330 | | | | | 335 | | | |

```
ttc att cgc cgt tct tgg gct gac gat caa ctt tac acc agc att gtt    1056
Phe Ile Arg Arg Ser Trp Ala Asp Asp Gln Leu Tyr Thr Ser Ile Val
        340                 345                 350 cag gaa tat gtt cag gag ctt ttg gag gga gga tac aat atc gag tgc    1104
Gln Glu Tyr Val Gln Glu Leu Leu Glu Gly Gly Tyr Asn Ile Glu Cys
            355                 360                 365 ttc atc gag ggc acc cga agc aga aca gga aaa ctt ttg cca cca aag    1152
Phe Ile Glu Gly Thr Arg Ser Arg Thr Gly Lys Leu Leu Pro Pro Lys
370                 375                 380 ctg gga gtc cta aag att atc atg gat gct atg ctt tcg aac cgc atc    1200
Leu Gly Val Leu Lys Ile Ile Met Asp Ala Met Leu Ser Asn Arg Ile
385                 390                 395                 400 caa gac tgc tac atc gtg ccc atc tct atc ggt tat gac aag gtc atc    1248
Gln Asp Cys Tyr Ile Val Pro Ile Ser Ile Gly Tyr Asp Lys Val Ile
                405                 410                 415 gaa acc gag act tat atc aat gag ctt ctc gga atc ccc aag gaa aag    1296
Glu Thr Glu Thr Tyr Ile Asn Glu Leu Leu Gly Ile Pro Lys Glu Lys
            420                 425                 430 gag agt ttg tgg ggt gtt att acg aat tcg agg ctg ctc cag ctc aag    1344
Glu Ser Leu Trp Gly Val Ile Thr Asn Ser Arg Leu Leu Gln Leu Lys
        435                 440                 445 atg ggc cgc att gat gtc cga ttt gca aag ccg tac agt ttg cga aac    1392
Met Gly Arg Ile Asp Val Arg Phe Ala Lys Pro Tyr Ser Leu Arg Asn
    450                 455                 460 ttt atg aat cat gag atc gag cgc aga gag atc atc aat aag cgg gaa    1440
Phe Met Asn His Glu Ile Glu Arg Arg Glu Ile Ile Asn Lys Arg Glu
465                 470                 475                 480 gac acc gat agt gtg gcg aaa tct cag ctg cta aag gca ttg ggc tac    1488
Asp Thr Asp Ser Val Ala Lys Ser Gln Leu Leu Lys Ala Leu Gly Tyr
                485                 490                 495 aag gtc ttg gca gac atc aac tcg gtc tct gta gta atg ccc acg gcc    1536
Lys Val Leu Ala Asp Ile Asn Ser Val Ser Val Val Met Pro Thr Ala
            500                 505                 510 ctc gtg ggt act gtc atc ctt aca ctc cga gga cga ggt gtt ggc cgt    1584
Leu Val Gly Thr Val Ile Leu Thr Leu Arg Gly Arg Gly Val Gly Arg
        515                 520                 525 aat gag ctg atc cgt cgt gtt gag tgg ctg aag cgc gag att ctt tcc    1632
Asn Glu Leu Ile Arg Arg Val Glu Trp Leu Lys Arg Glu Ile Leu Ser
530                 535                 540 aag ggt ggt cgc gtt gcc aac ttt agc ggg atg gaa act ggc gag gtt    1680
Lys Gly Gly Arg Val Ala Asn Phe Ser Gly Met Glu Thr Gly Glu Val
545                 550                 555                 560 gta gat cga gca ttg ggc gtt ctt aag gac ctt gtg gcg ctg cag aag    1728
Val Asp Arg Ala Leu Gly Val Leu Lys Asp Leu Val Ala Leu Gln Lys
                565                 570                 575 aat ttg ctc gag ccc gtc ttc tat gcg gtc aag cgc ttc gag ctt tcg    1776
Asn Leu Leu Glu Pro Val Phe Tyr Ala Val Lys Arg Phe Glu Leu Ser
            580                 585                 590 ttc tac agg aat cag ctc atc cac ctc ttt gtc cat gag gcc atc atc    1824
Phe Tyr Arg Asn Gln Leu Ile His Leu Phe Val His Glu Ala Ile Ile
        595                 600                 605 gcc gtg acg atg tac acc cgc atc aag att ggt ggc gcc aag tct aca    1872
Ala Val Thr Met Tyr Thr Arg Ile Lys Ile Gly Gly Ala Lys Ser Thr
    610                 615                 620 caa cac att agt cag aat gag ctg ctg aac gag gtc acc ttc ctg agc    1920
Gln His Ile Ser Gln Asn Glu Leu Leu Asn Glu Val Thr Phe Leu Ser
625                 630                 635                 640 cgc ctg ctc aag acc gac ttt atc tac aac cct ggc gat att gag agt    1968
Arg Leu Leu Lys Thr Asp Phe Ile Tyr Asn Pro Gly Asp Ile Glu Ser
```

```
                        645                 650                 655
aac ttg gag cat aca ttg gat tac ctc aag aaa tcc aat gtg atc gag      2016
Asn Leu Glu His Thr Leu Asp Tyr Leu Lys Lys Ser Asn Val Ile Glu
        660                 665                 670 gtt gac agt gaa gga tat gtc gga ctc tct gat gct gaa cgc agc aag      2064
Val Asp Ser Glu Gly Tyr Val Gly Leu Ser Asp Ala Glu Arg Ser Lys
675                 680                 685 ggc cga gag aac tat gac ttt tat tgt ttc ctg ctc tgg ccc ttc gtg      2112
Gly Arg Glu Asn Tyr Asp Phe Tyr Cys Phe Leu Leu Trp Pro Phe Val
    690                 695                 700 gag aca tac tgg ctc gca gcc gtg tcc ctg tat acc ctg att ccc acc      2160
Glu Thr Tyr Trp Leu Ala Ala Val Ser Leu Tyr Thr Leu Ile Pro Thr
705                 710                 715                 720 gcc aaa gag ttg act cag cag ttg gac agc aac gga gag cct cag gtt      2208
Ala Lys Glu Leu Thr Gln Gln Leu Asp Ser Asn Gly Glu Pro Gln Val
                725                 730                 735 cac tgg gtt gag gag cgc gtg ttc atg gag aag acg caa atg ttc gga      2256
His Trp Val Glu Glu Arg Val Phe Met Glu Lys Thr Gln Met Phe Gly
            740                 745                 750 aag acg ctt tac tac cag gga gac ctc tcc tac ttt gag tct gtc aac      2304
Lys Thr Leu Tyr Tyr Gln Gly Asp Leu Ser Tyr Phe Glu Ser Val Asn
        755                 760                 765 atg gag acg ctc aag aat ggt ttt aat cgt ctg tgc gat tat ggc atc      2352
Met Glu Thr Leu Lys Asn Gly Phe Asn Arg Leu Cys Asp Tyr Gly Ile
    770                 775                 780 ctt atg atg aag cga ccc acc aat gcc aag gag aag aca aag gtt gct      2400
Leu Met Met Lys Arg Pro Thr Asn Ala Lys Glu Lys Thr Lys Val Ala
785                 790                 795                 800 ctc cac cct gat ttt atg cca agc cga ggt gct gac ggt cat gtc att      2448
Leu His Pro Asp Phe Met Pro Ser Arg Gly Ala Asp Gly His Val Ile
                805                 810                 815 gcc agc ggc gca ctt tgg gat atg gtc gaa cat atc ggc acg ttc aga      2496
Ala Ser Gly Ala Leu Trp Asp Met Val Glu His Ile Gly Thr Phe Arg
            820                 825                 830 cgt gaa ggc aag aat cgt cgt gat aac gcc aca gtt tcc tcc cgt gtc      2544
Arg Glu Gly Lys Asn Arg Arg Asp Asn Ala Thr Val Ser Ser Arg Val
        835                 840                 845 ctg cgg ttt gca gag gtc gtc gcg aac gct cca gct ccg gtt aag gta      2592
Leu Arg Phe Ala Glu Val Val Ala Asn Ala Pro Ala Pro Val Lys Val
    850                 855                 860 ccc ttg ccc aat ccg gca ccc aaa agg aca ggc gat ggc gcc ccg aaa      2640
Pro Leu Pro Asn Pro Ala Pro Lys Arg Thr Gly Asp Gly Ala Pro Lys
865                 870                 875                 880 tta                                                                   2643
Leu

<210> SEQ ID NO 5
<211> LENGTH: 881
<212> TYPE: PRT
<213> ORGANISM: Mortierella alpina

<400> SEQUENCE: 5

Met Thr Thr Gly Asp Ser Thr Ala Ala Asp Gly Ser Ser Ser Ser Ser
1               5                   10                  15

Ser Asn Asn Ser Thr Asn Ile Ala Ser Thr Ser Asn Gly Lys Ala Ala
            20                  25                  30

Pro His Pro Leu Gln Gly Gly Ser Pro Ala Pro Val Ala Pro Val Leu
        35                  40                  45

Glu Leu Lys Pro Leu Lys Asn Val Met Pro Ile Val Pro Ala Gln Gln
```

-continued

```
             50                  55                  60
Val Asp Ser Ser Cys Pro Pro Ser Gly Glu Ser Ser Pro Leu Ile
 65                  70                  75                  80

Pro Ser Leu Gly Glu Gly Val His Ser Gly His Gly His Val Val Asp
                     85                  90                  95

Asn Asp Glu Ser Gly Val Glu Asn Ile Thr Lys Lys His Ala Gly Arg
                100                 105                 110

Ile Arg Glu Asp Pro Val Gly Phe Val Gln Thr Ala Ala Phe Tyr
            115                 120                 125

Gln Gly Thr Gly Trp Arg Ser Tyr Ser Asn Tyr Val Gly Thr Arg Ile
            130                 135                 140

Leu Tyr Glu Gly Phe Ser Ala Thr Phe Lys Glu Arg Ile Leu Ala Ser
145                 150                 155                 160

Ser Lys Val Asn Asp Leu Ile Lys Asp Met Ala Asn Lys Gln Leu Asp
                165                 170                 175

Val Leu Ile Lys Gln Arg Gln Asp Ala Tyr Asp Ala Glu Arg Thr Ala
            180                 185                 190

Asn Ala Gly Lys Lys Asn Phe Lys Pro Lys Val Arg Leu Leu Arg Pro
            195                 200                 205

Glu Asp Ile Glu Ala Arg Arg Lys Thr Leu Glu Ala Glu Leu Val Ala
210                 215                 220

Val Ala Lys Ser Asn Ile Asp Lys Leu Val Cys Asp Met Asn Ser Met
225                 230                 235                 240

Lys Phe Ile Arg Phe Phe Ala Phe Leu Ile Asn Asn Ile Leu Val Arg
                245                 250                 255

Met Tyr His Gln Gly Ile His Ile Lys Glu Ser Glu Phe Leu Glu Leu
                260                 265                 270

Arg Arg Ile Ala Glu Tyr Cys Ala Glu Lys Lys Tyr Ser Met Val Val
            275                 280                 285

Leu Pro Cys His Lys Ser His Ile Asp Tyr Leu Val Val Ser Tyr Ile
            290                 295                 300

Phe Phe Arg Met Gly Leu Ala Leu Pro His Ile Ala Ala Gly Asp Asn
305                 310                 315                 320

Leu Asp Met Pro Ile Val Gly Lys Ala Leu Lys Gly Ala Gly Ala Phe
                325                 330                 335

Phe Ile Arg Arg Ser Trp Ala Asp Asp Gln Leu Tyr Thr Ser Ile Val
            340                 345                 350

Gln Glu Tyr Val Gln Glu Leu Leu Glu Gly Gly Tyr Asn Ile Glu Cys
            355                 360                 365

Phe Ile Glu Gly Thr Arg Ser Arg Thr Gly Lys Leu Leu Pro Pro Lys
            370                 375                 380

Leu Gly Val Leu Lys Ile Ile Met Asp Ala Met Leu Ser Asn Arg Ile
385                 390                 395                 400

Gln Asp Cys Tyr Ile Val Pro Ile Ser Ile Gly Tyr Asp Lys Val Ile
                405                 410                 415

Glu Thr Glu Thr Tyr Ile Asn Glu Leu Leu Gly Ile Pro Lys Glu Lys
            420                 425                 430

Glu Ser Leu Trp Gly Val Ile Thr Asn Ser Arg Leu Leu Gln Leu Lys
            435                 440                 445

Met Gly Arg Ile Asp Val Arg Phe Ala Lys Pro Tyr Ser Leu Arg Asn
            450                 455                 460

Phe Met Asn His Glu Ile Glu Arg Arg Glu Ile Ile Asn Lys Arg Glu
465                 470                 475                 480
```

```
Asp Thr Asp Ser Val Ala Lys Ser Gln Leu Leu Lys Ala Leu Gly Tyr
                485                 490                 495
Lys Val Leu Ala Asp Ile Asn Ser Val Ser Val Met Pro Thr Ala
            500                 505                 510
Leu Val Gly Thr Val Ile Leu Thr Leu Arg Gly Arg Gly Val Gly Arg
                515                 520                 525
Asn Glu Leu Ile Arg Arg Val Glu Trp Leu Lys Arg Glu Ile Leu Ser
            530                 535                 540
Lys Gly Gly Arg Val Ala Asn Phe Ser Gly Met Glu Thr Gly Glu Val
545                 550                 555                 560
Val Asp Arg Ala Leu Gly Val Leu Lys Asp Leu Val Ala Leu Gln Lys
                565                 570                 575
Asn Leu Leu Glu Pro Val Phe Tyr Ala Val Lys Arg Phe Glu Leu Ser
            580                 585                 590
Phe Tyr Arg Asn Gln Leu Ile His Leu Phe Val His Glu Ala Ile Ile
        595                 600                 605
Ala Val Thr Met Tyr Thr Arg Ile Lys Ile Gly Gly Ala Lys Ser Thr
        610                 615                 620
Gln His Ile Ser Gln Asn Glu Leu Leu Asn Glu Val Thr Phe Leu Ser
625                 630                 635                 640
Arg Leu Leu Lys Thr Asp Phe Ile Tyr Asn Pro Gly Asp Ile Glu Ser
                645                 650                 655
Asn Leu Glu His Thr Leu Asp Tyr Leu Lys Lys Ser Asn Val Ile Glu
            660                 665                 670
Val Asp Ser Glu Gly Tyr Val Gly Leu Ser Asp Ala Glu Arg Ser Lys
        675                 680                 685
Gly Arg Glu Asn Tyr Asp Phe Tyr Cys Phe Leu Leu Trp Pro Phe Val
690                 695                 700
Glu Thr Tyr Trp Leu Ala Ala Val Ser Leu Tyr Thr Leu Ile Pro Thr
705                 710                 715                 720
Ala Lys Glu Leu Thr Gln Gln Leu Asp Ser Asn Gly Glu Pro Gln Val
                725                 730                 735
His Trp Val Glu Glu Arg Val Phe Met Glu Lys Thr Gln Met Phe Gly
            740                 745                 750
Lys Thr Leu Tyr Tyr Gln Gly Asp Leu Ser Tyr Phe Glu Ser Val Asn
        755                 760                 765
Met Glu Thr Leu Lys Asn Gly Phe Asn Arg Leu Cys Asp Tyr Gly Ile
        770                 775                 780
Leu Met Met Lys Arg Pro Thr Asn Ala Lys Glu Lys Thr Lys Val Ala
785                 790                 795                 800
Leu His Pro Asp Phe Met Pro Ser Arg Gly Ala Asp Gly His Val Ile
                805                 810                 815
Ala Ser Gly Ala Leu Trp Asp Met Val Glu His Ile Gly Thr Phe Arg
            820                 825                 830
Arg Glu Gly Lys Asn Arg Arg Asp Asn Ala Thr Val Ser Ser Arg Val
        835                 840                 845
Leu Arg Phe Ala Glu Val Val Ala Asn Ala Pro Ala Pro Val Lys Val
        850                 855                 860
Pro Leu Pro Asn Pro Ala Pro Lys Arg Thr Gly Asp Gly Ala Pro Lys
865                 870                 875                 880
Leu
```

<210> SEQ ID NO 6
<211> LENGTH: 2646
<212> TYPE: DNA
<213> ORGANISM: Mortierella alpina

<400> SEQUENCE: 6

| | | | | | |
|---|---|---|---|---|---|
| atgacaaccg | cgacagtac | cgctgctgac | ggtagcagca | gcagtagcag | caacaacagc | 60 |
| accaacattg | ccagtactag | taacggcaag | gctgctcccc | acccactcca | aggggggatca | 120 |
| cccgctcctg | tagctccagt | tttggaattg | aagcctctca | agaatgttat | gcccatcgtt | 180 |
| ccagctcagc | aagtcgactc | ctcctcgtgc | cctccctctg | gtgaatctag | cccgttgatt | 240 |
| cccagtttgg | gcgaaggagt | gcattcgggt | catggacacg | ttgtcgacaa | tgacgagtcc | 300 |
| ggcgtggaga | acattaccaa | aaagcacgca | ggacgaatta | gagaagatcc | ggtcggcttc | 360 |
| gtggtgcaga | ctgcagcttt | ctatcagggc | acggggttgga | gaagctacag | caactatgtt | 420 |
| ggaacgcgca | ttctttacga | aggcttctct | gcaaccttca | aggagcgaat | tctcgccagt | 480 |
| tcaaaagtga | atgatctcat | caaggacatg | gccaacaagc | agttggatgt | cctgatcaag | 540 |
| caaagacaag | atgcgtatga | cgcagagagg | actgcaaatg | caggaaaaaa | gaacttcaag | 600 |
| cccaaagttc | gactccttcg | cccagaagat | atcgaggctc | gtcgcaaaac | attagaagcc | 660 |
| gagcttgttg | cggtggcaaa | gtcaaatatc | gacaaacttg | tttgtgatat | gaacagtatg | 720 |
| aaattcatca | ggttcttcgc | cttcctcatc | aacaacatcc | ttgtgagaat | gtaccatcaa | 780 |
| ggaattcaca | tcaaggagtc | cgagttcttg | gagctgcgga | ggatagctga | gtactgcgca | 840 |
| gagaaaaagt | attcgatggt | ggtgttgcca | tgccacaagt | cacacatcga | ctacctcgtc | 900 |
| gtctcgtaca | ttttcttccg | catgggatta | gctttacctc | acattgctgc | tggcgataac | 960 |
| ctggacatgc | ccattgtcgg | aaaggcactc | aaaggagcag | gcgcgttctt | cattcgccgt | 1020 |
| tcttgggctg | acgatcaact | ttacaccagc | attgttcagg | aatatgttca | ggagcttttg | 1080 |
| gagggaggat | acaatatcga | gtgcttcatc | gagggcaccc | gaagcagaac | aggaaaactt | 1140 |
| ttgccaccaa | agctgggagt | cctaaagatt | atcatggatg | ctatgctttc | gaaccgcatc | 1200 |
| caagactgct | acatcgtgcc | catctctatc | ggttatgaca | aggtcatcga | aaccgagact | 1260 |
| tatatcaatg | agcttctcgg | aatccccaag | gaaaaggaga | gtttgtgggg | tgttattacg | 1320 |
| aattcgaggc | tgctccagct | caagatgggc | cgcattgatg | tccgatttgc | aaagccgtac | 1380 |
| agtttgcgaa | actttatgaa | tcatgagatc | gagcgcagag | agatcatcaa | taagcgggaa | 1440 |
| gacaccgata | gtgtggcgaa | atctcagctg | ctaaaggcat | gggctacaa | ggtcttggca | 1500 |
| gacatcaact | cggtctctgt | agtaatgccc | acggccctcg | tgggtactgt | catccttaca | 1560 |
| ctccgaggac | gaggtgttgg | ccgtaatgag | ctgatccgtc | gtgttgagtg | gctgaagcgc | 1620 |
| gagattcttt | ccaagggtgg | tcgcgttgcc | aactttagcg | ggatggaaac | tggcgaggtt | 1680 |
| gtagatcgag | cattgggcgt | tcttaaggac | cttgtggcgc | tgcagaagaa | tttgctcgag | 1740 |
| cccgtcttct | atgcggtcaa | gcgcttcgag | cttccgttct | acaggaatca | gctcatccac | 1800 |
| ctctttgtcc | atgaggccat | catcgccgtg | acgatgtaca | cccgcatcaa | gattggtggc | 1860 |
| gccaagtcta | cacaacacat | tagtcagaat | gagctgctga | acgaggtcac | cttcctgagc | 1920 |
| cgcctgctca | agaccgactt | tatctacaac | cctggcgata | ttgagagtaa | cttggagcat | 1980 |
| acattggatt | acctcaagaa | atccaatgtg | atcgaggttg | acagtgaagg | atatgtcgga | 2040 |
| ctctctgatg | ctgaacgcag | caagggccga | gagaactatg | acttttattg | tttccctgctc | 2100 |
| tggcccttcg | tggagacata | ctggctcgca | gccgtgtccc | tgtataccct | gattcccacc | 2160 |

```
gccaaagagt tgactcagca gttggacagc aacggagagc ctcaggttca ctgggttgag    2220
gagcgcgtgt tcatggagaa gacgcaaatg ttcggaaaga cgctttacta ccagggagac    2280
ctctcctact ttgagtctgt caacatggag acgctcaaga atggttttaa tcgtctgtgc    2340
gattatggca tccttatgat gaagcgaccc accaatgcca aggagaagac aaaggttgct    2400
ctccaccctg attttatgcc aagccgaggt gctgacggtc atgtcattgc cagcggcgca    2460
cttggggata tggtcgaaca tatcggcacg ttcagacgtg aaggcaagaa tcgtcgtgat    2520
aacgccacag tttcctcccg tgtcctgcgg tttgcagagg tcgtcgcgaa cgctccagct    2580
ccggttaagg taccccttgcc caatccggca cccaaaagga caggcgatgg cgccccgaaa    2640
ttataa                                                              2646

<210> SEQ ID NO 7
<211> LENGTH: 4248
<212> TYPE: DNA
<213> ORGANISM: Mortierella alpina

<400> SEQUENCE: 7
gttgacatag tcttttttggt agcagtagca ttgttgtagt ttctcttact caacggacag      60
cagcagcacg accgccgagg taaagcggtg gatcccatag agactctttt gccctcgtct     120
ccactgtcgc tctccccaca gaaaaacatt tttatttcct ttcccgcatt ttttctttct    180 tttttcctg cctctcttgt ctctcctccc ctaagcacca cctaacccgc tctatcgccc     240
aaccacttca actcagcacc ctcacggagc ctgccaacca acgttgcaag aaggaaaaaa     300
agtacagcgc atcttgtagt ccagcgcgga gcagtggaaa aacctctcca ttccgaccta     360
acagatcacg cagtctgatc agctagtttg ccccacagtt attgcatcac cctttcaacc     420
agtccacatg acaaccggcg acagtaccgc tgctgacggt agcagcagca gtagcagcaa     480
caacagcacc aacattgcca gtactagtaa cggcaaggct gctccccacc cactccaagg     540
gggatcaccc gctcctgtag ctccagtttt ggaattgaag cctctcaaga atgttatgcc     600
catcgttcca gctcagcaag tcgactcctc ctcgtgccct ccctctggtg aatctagccc     660
gttgattccc agtttgggcg aaggagtgca ttcgggtcat ggacacgttg tcgacaatga     720
cgagtccggc gtggagaaca ttacgcaagt tcaaattgaa tattccagcg gctatgaacg     780
agtttggatg cttgtttagt tttgtattaa cacgaacttt cgctcttgtt attgttgtta     840
tcaatgcagc aaaaagcacg caggacgaat tagagaagat ccggtcggct tcgtggtgca     900
gactgcagct ttctatcagg gcacggtacg ttcaatatct gacatcactg ctttagtgga     960
gccgcagagg aaagcacttc ttaacgacaa ctgcagctgg atcggtcggt acctcctgct    1020
caacgagcta tcagcccttc tccgccgcca ttgtgagggt gatttgtctc ataccaggaa    1080
cagcagaaga aaaagaggaa tcgtgttcac aaagcatcgc ttcggggttg cgctcacgct    1140
cggtcctctt gattgctccc tggaagtctc ccttctgcaa actgtcactc tcccacgttc    1200 ccttttttt ttttttttta ctatcctccc atccctgcc tctcgtcatg cttgagctga     1260
ataatgctaa attcttatcc gcatatcgtc tttgcttttt agggttggag aagctacagc    1320
aactatgttg gaacgcgcat tctttacgaa ggcttctctg caaccttcaa ggagcgaatt    1380
ctcgccagtt caaaaggtaa cacaagatag ggtgctgtct gtacttcaac acgattcgtc    1440
aaaatggcat gatctaacga accctaccctt gacctcctag tgaatgatct catcaaggac    1500
atggccaaca agcagttgga tgtcctgatc aagcaaagac aagatgcgta tgacgcagag    1560
aggactgcaa atgcaggaaa aaagaacttc aagcccaaag ttcgactcct tcgcccagaa    1620
```

```
gatatcgagg ctcgtcgcaa aacattagaa gccgagcttg ttgcggtggc aaagtcaaat   1680
atcgacaaac ttgtttgtga tatgaacagt atgaaattca tcaggtatgg accaacacga   1740
gaataacgca gcgtggaact gaacagtgtg gcagaagagg gatggcgaga tatatttgtt   1800
gtttgctaga caccagatgt taacaacttt cctccttggc tgatgtgtta ggttcttcgc   1860
cttcctcatc aacaacatcc ttgtgagaat gtaccatcaa ggaattcaca tcaaggagtc   1920
cgagttcttg gagctgcgga ggatagctga gtactgcgca gagaaaaagt attcgatggt   1980
ggtgttgcca tgccacaagt cacacatcga ctacctcgtc gtctcgtaca ttttcttccg   2040
catgggatta gctttacctc acattgctgc tggcgataac ctggacatgc ccattgtcgg   2100
aaaggcactc aaaggagcag gcgcgttctt cattcgccgt tcttgggctg acgatcaact   2160
ttacaccagc attgttcagg aatatgttca ggagcttttg gagggaggat acaatatcga   2220
gtgcttcatc gagggcaccc gaagcagaac aggaaaactt ttgccaccaa gctgggagg   2280 ttcgttcaca gctttggtct tgtttttgct actgggcacg ctggcgatct ctttgggtat   2340
taaccttcac accaatccac ctttactagt cctaaagatt atcatggatg ctatgctttc   2400
gaaccgcatc caagactgct acatcgtgcc catctctatc ggttatgaca aggtcatcga   2460
aaccgagact tatatcaatg agcttctcgg aatccccaag gaaaaggaga gtttgtgggg   2520
tgttattacg aattcgaggc tgctccagct caagatgggc cgcattgatg tccgatttgc   2580
aaagccgtac agtttgcgaa actttatgaa tcatgagatc gagcgcagag agtaagcaga   2640
acctgtgttt tgttgtgcaa gacgttttca aaactggaga ggaattatgt tgacccaggg   2700
ctatttgttt ttctgcattt aggatcatca ataagcggga agacaccgat agtgtggcga   2760
aatctcagct gctaaaggca ttgggctaca aggtcttggc agacatcaac tcggtctctg   2820
tagtaatgcc cacggccctc gtgggtactg tcatccttac actccgagga cgaggtgttg   2880
gccgtaatga gctgatccgt cgtgttgagt ggctgaagcg cgagattctt ccaagggtg   2940 gtcgcgttgc caactttagc gggatggaaa ctggcgaggt tgtagatcga gcattgggcg   3000
ttcttaagga ccttgtggcg ctgcagaaga atttgctcga gcccgtcttc tatgcggtca   3060
agcgcttcga gctttcgttc tacaggaatc agctcatcca cctctttgtc catgaggcca   3120
tcatcgccgt gacgatgtac acccgcatca agattggtgg cgccaagtct acacaacaca   3180
ttagtcagaa tgagctgctg aacgaggtca ccttcctgag ccgcctgctc aagaccgact   3240
ttatctacaa ccctggcgat attgagagta acttggagca tacattggat tacctcaagg   3300
tgagttatct cgcacaggaa taagggacag ctgcaattcg ctgaaagtag acctgagcgc   3360
aacggtctaa cattatcgtt cttttctaga aatccaatgt gatcgaggtt gacagtgaag   3420
gatatgtcgg actctctgat gctgaacgca gcaagggccg agagaactat ggtaatgggc   3480
tattctattt gtactcacta cagacgtgat gtgcatgttg tatcggccga aaagtcgtt   3540 tctgactgaa cctctcattt tatcattact ctagactttt attgtttcct gctctggccc   3600
ttcgtggaga catactggct cgcagccgtg tccctgtata ccctgattcc caccgccaaa   3660
gagttgactc agcagttgga cagcaacgga gagcctcagg ttcactgggt tgaggagcgc   3720
gtgttcatgg agaagacgca aatgttcgga aagacgcttt actaccaggg agacctctcc   3780
tactttgagt ctgtcaacat ggagacgctc aagaatggtt ttaatcgtct gtgcgattat   3840
ggcatcctta tgatgaagcg acccaccaat gccaaggaga agacaaaggt tgctctccac   3900
cctgatttta tgccaagccg aggtgctgac ggtcatgtca ttgccagcgg cgcactttgg   3960
```

```
gatatggtcg aacatatcgg cacgttcaga cgtgaaggca agaatcgtcg tgataacgcc      4020
acaggtaagg aacatgtgtc ttgacattgc tcgaaacgaa atttgttgct ctgtatgctt      4080
tgtcaccagg ggtactaatg gcttgtgctc ttgcttacac tttccaacct agtttcctcc      4140
cgtgtcctgc ggtttgcaga ggtcgtcgcg aacgctccag ctccggttaa ggtacccttg      4200
cccaatccgg cacccaaaag gacaggcgat ggcgccccga aattataa                   4248
```

<210> SEQ ID NO 8
<211> LENGTH: 2364
<212> TYPE: DNA
<213> ORGANISM: Mortierella alpina
<220> FEATURE:
<221> NAME/KEY: CDS
<222> LOCATION: (1)..(2364)
<223> OTHER INFORMATION:

<400> SEQUENCE: 8

```
atg gaa gga gac gca gta cgg cct gct ttg gcc aga aag atc cct ggt       48
Met Glu Gly Asp Ala Val Arg Pro Ala Leu Ala Arg Lys Ile Pro Gly
1               5                   10                  15 ctc tac agc ttc atc aaa ctc ctt tgc agg acg ctt ttt cac atc ttc       96
Leu Tyr Ser Phe Ile Lys Leu Leu Cys Arg Thr Leu Phe His Ile Phe
            20                  25                  30 ttc agg gat tac gac gcc ttt cat acc cag ttt gtt cca cag gac gaa      144
Phe Arg Asp Tyr Asp Ala Phe His Thr Gln Phe Val Pro Gln Asp Glu
        35                  40                  45 cca ttg cta gtt atc tcc aac cat ggc aac tac ctt ctg gat ggc ctc      192
Pro Leu Leu Val Ile Ser Asn His Gly Asn Tyr Leu Leu Asp Gly Leu
    50                  55                  60 gcc ttg ttg gcc acc ttt cca ggc cag atc tcc ttt ttg atg gca cag      240
Ala Leu Leu Ala Thr Phe Pro Gly Gln Ile Ser Phe Leu Met Ala Gln
65                  70                  75                  80 ccc aat ttc aag act gca att ggt ggc atc gcc agg aag att ggt gcc      288
Pro Asn Phe Lys Thr Ala Ile Gly Gly Ile Ala Arg Lys Ile Gly Ala
                85                  90                  95 att cca gta ctg aga cca cag gac gcg gcc aga tat gac ggt gcg agt      336
Ile Pro Val Leu Arg Pro Gln Asp Ala Ala Arg Tyr Asp Gly Ala Ser
            100                 105                 110 atg gtc aca atc gct cag gat ggc aac tca gtc ctc ggt cag ggg att      384
Met Val Thr Ile Ala Gln Asp Gly Asn Ser Val Leu Gly Gln Gly Ile
        115                 120                 125 ggc aag cag ctg act ttg ggc gat act gtc tat atc gag tgt ggg acg      432
Gly Lys Gln Leu Thr Leu Gly Asp Thr Val Tyr Ile Glu Cys Gly Thr
    130                 135                 140 ttc cag gac gct ggc agg gac aat cgc gtc acg caa tgt tat ggc gtg      480
Phe Gln Asp Ala Gly Arg Asp Asn Arg Val Thr Gln Cys Tyr Gly Val
145                 150                 155                 160 gtc agt gcg atc gtc agt gac aac gag gtg ttg ttc aag gct ccc ggt      528
Val Ser Ala Ile Val Ser Asp Asn Glu Val Leu Phe Lys Ala Pro Gly
                165                 170                 175 ttg aaa tgg att ccc gca tcc ttg aca tcg gaa cgc gac att gcc tat      576
Leu Lys Trp Ile Pro Ala Ser Leu Thr Ser Glu Arg Asp Ile Ala Tyr
            180                 185                 190 atc aaa tcg cga aag att gtt cgg cat ggg tca ctc aag atc aga gtg      624
Ile Lys Ser Arg Lys Ile Val Arg His Gly Ser Leu Lys Ile Arg Val
        195                 200                 205 gaa cgt ggc aac acc tgg gtc gga atc aat gag gcg ctt aaa gca cag      672
Glu Arg Gly Asn Thr Trp Val Gly Ile Asn Glu Ala Leu Lys Ala Gln
    210                 215                 220 gag cag cag aac aat ggc tcg ttg gca agc agc gca acg ggg acg atc      720
Glu Gln Gln Asn Asn Gly Ser Leu Ala Ser Ser Ala Thr Gly Thr Ile
```

```
                Glu Gln Gln Asn Asn Gly Ser Leu Ala Ser Ser Ala Thr Gly Thr Ile
                225                 230                 235                 240 ggc aag ttt gtt cac aag ata ttt tca aag tcg ccg gat gca gac gca            768
Gly Lys Phe Val His Lys Ile Phe Ser Lys Ser Pro Asp Ala Asp Ala
                        245                 250                 255 aga tca gat gat gtg cat ttg gcc gag aat ggg tat tcc gga gca gat            816
Arg Ser Asp Asp Val His Leu Ala Glu Asn Gly Tyr Ser Gly Ala Asp
                260                 265                 270 atc ccc ggg tcc ttg acc gct cca gcc aac ttt cac aca act gag act            864
Ile Pro Gly Ser Leu Thr Ala Pro Ala Asn Phe His Thr Thr Glu Thr
            275                 280                 285 aca cca cta ctc aaa aag gcg cgc tcg tca aac agc tcc agt cat cct            912
Thr Pro Leu Leu Lys Lys Ala Arg Ser Ser Asn Ser Ser Ser His Pro
        290                 295                 300 ata tac aca gta cca aag cgc gca gac tcg aac gcg agg ctt tca tca            960
Ile Tyr Thr Val Pro Lys Arg Ala Asp Ser Asn Ala Arg Leu Ser Ser
305                 310                 315                 320 tac tct acc act cac agc aca aat gca gtg gcc gat gcc gac aac gac           1008
Tyr Ser Thr Thr His Ser Thr Asn Ala Val Ala Asp Ala Asp Asn Asp
                325                 330                 335 gac gag acc acg cgc cct gca aat gga ctt agg aac gcg caa ggc gga           1056
Asp Glu Thr Thr Arg Pro Ala Asn Gly Leu Arg Asn Ala Gln Gly Gly
            340                 345                 350 cac aac ccc gct gga acc aat ggc gtt gtc aat gga ggc gca tcc aca           1104
His Asn Pro Ala Gly Thr Asn Gly Val Val Asn Gly Gly Ala Ser Thr
        355                 360                 365 tcc atg agc cca cga agc act cca ttg acc tcc cct aca ctt cac agc           1152
Ser Met Ser Pro Arg Ser Thr Pro Leu Thr Ser Pro Thr Leu His Ser
370                 375                 380 tcc aca tcg gcc gtg tca cac ttc ccc tcg cga ccc tgc ccc ttc cag           1200
Ser Thr Ser Ala Val Ser His Phe Pro Ser Arg Pro Cys Pro Phe Gln
385                 390                 395                 400 ttc tca cac cca atc gac cat tct gtg atc tac gag agc gtc tgg aag           1248
Phe Ser His Pro Ile Asp His Ser Val Ile Tyr Glu Ser Val Trp Lys
                405                 410                 415 aac ttt gag gat ggt cgc acc gtt gct gta ttc cct gaa ggc gta tcg           1296
Asn Phe Glu Asp Gly Arg Thr Val Ala Val Phe Pro Glu Gly Val Ser
            420                 425                 430 agc gac gat tat cac ttg ctc gac ttc aaa tat ggc tgc acc atc atg           1344
Ser Asp Asp Tyr His Leu Leu Asp Phe Lys Tyr Gly Cys Thr Ile Met
        435                 440                 445 gtt ctt gga tac ctg gct cag cat cgc tct aag act cta agg att ata           1392
Val Leu Gly Tyr Leu Ala Gln His Arg Ser Lys Thr Leu Arg Ile Ile
450                 455                 460 cca tgc gga ctg aac ttc ttt aat cgc cat cga ttt cga tcc cgg ttc           1440
Pro Cys Gly Leu Asn Phe Phe Asn Arg His Arg Phe Arg Ser Arg Phe
465                 470                 475                 480 tac gcc gac tac tcc cat ccg ctc acc gtc ccc gac cac ctt gta gag           1488
Tyr Ala Asp Tyr Ser His Pro Leu Thr Val Pro Asp His Leu Val Glu
                485                 490                 495 atg tat cgc gaa gga gga gaa gcc aag aag caa gcc tgt act gag ctt           1536
Met Tyr Arg Glu Gly Gly Glu Ala Lys Lys Gln Ala Cys Thr Glu Leu
            500                 505                 510 ctg cag atg att cac tcg gct gtg gag ggg ctg act ctt aac gca cca           1584
Leu Gln Met Ile His Ser Ala Val Glu Gly Leu Thr Leu Asn Ala Pro
        515                 520                 525 aac tac gac gag ctg cga ctt tac aag gca acg cga cga ctc tac agc           1632
Asn Tyr Asp Glu Leu Arg Leu Tyr Lys Ala Thr Arg Arg Leu Tyr Ser
530                 535                 540
```

```
act ggg aag aag ctt acc gtg cca cag aaa ttg gag cta act cgc cgt    1680
Thr Gly Lys Lys Leu Thr Val Pro Gln Lys Leu Glu Leu Thr Arg Arg
545                 550                 555                 560 ttt gcg aaa ggt tat caa aat ctg gtc atg acg ccg agc atg gct gca    1728
Phe Ala Lys Gly Tyr Gln Asn Leu Val Met Thr Pro Ser Met Ala Ala
                565                 570                 575 ttg aaa cgc gac att gat gct tat gac aag cat ctc tcc agc agc ggc    1776
Leu Lys Arg Asp Ile Asp Ala Tyr Asp Lys His Leu Ser Ser Ser Gly
        580                 585                 590 gtc cga gac gca caa ctg acc gca aac cca agc att ctg gct gcc ctt    1824
Val Arg Asp Ala Gln Leu Thr Ala Asn Pro Ser Ile Leu Ala Ala Leu
    595                 600                 605 gta ttc ata ttg ccc gcg tta ttc ctc ttg cca gtg ctg ttc ctg ctt    1872
Val Phe Ile Leu Pro Ala Leu Phe Leu Leu Pro Val Leu Phe Leu Leu
610                 615                 620 tcg tta ccc ggg acg ttg ctc ttc gga cct gtt gga ctt ttg gcg tcg    1920
Ser Leu Pro Gly Thr Leu Leu Phe Gly Pro Val Gly Leu Leu Ala Ser
625                 630                 635                 640 tgg gcg gca aag cag aaa gga cag cag gcc atg ctt gcc ttt cag tct    1968
Trp Ala Ala Lys Gln Lys Gly Gln Gln Ala Met Leu Ala Phe Gln Ser
                645                 650                 655 tat ctc cca gtt tca cgt tgg cct ggc cga gat gtg atc gcc acc tgg    2016
Tyr Leu Pro Val Ser Arg Trp Pro Gly Arg Asp Val Ile Ala Thr Trp
        660                 665                 670 aag atc gtg gtg tcc ttg gcg ttg atg ccc gtc tgc ttt att ctg gac    2064
Lys Ile Val Val Ser Leu Ala Leu Met Pro Val Cys Phe Ile Leu Asp
    675                 680                 685 gca aca ctg ctc acg atc cta gca cac cat tgg gaa gca ctg cag gag    2112
Ala Thr Leu Leu Thr Ile Leu Ala His His Trp Glu Ala Leu Gln Glu
690                 695                 700 tac tgg act atg ggt cgt cta gtt gcg ttc tgg ctg ctg tca aca ttt    2160
Tyr Trp Thr Met Gly Arg Leu Val Ala Phe Trp Leu Leu Ser Thr Phe
705                 710                 715                 720 gtg att ttt cca acg atg gcg tat ggt acg gtc tgg ctt tgg gag tgg    2208
Val Ile Phe Pro Thr Met Ala Tyr Gly Thr Val Trp Leu Trp Glu Trp
                725                 730                 735 cag att gat ttg aag atg cag atc tat gta tgg tgg tgg aag ctc tgc    2256
Gln Ile Asp Leu Lys Met Gln Ile Tyr Val Trp Trp Trp Lys Leu Cys
        740                 745                 750 gga ggc aat gca gag atg aag cgc tgg aga cag gat ctt gtc gag aga    2304
Gly Gly Asn Ala Glu Met Lys Arg Trp Arg Gln Asp Leu Val Glu Arg
    755                 760                 765 atg gat gca ctt gtc gaa agg atg ggc ggt aga agg gtg ttt gat gta    2352
Met Asp Ala Leu Val Glu Arg Met Gly Gly Arg Arg Val Phe Asp Val
770                 775                 780 tcg ggc tat tat                                                    2364
Ser Gly Tyr Tyr
785

<210> SEQ ID NO 9
<211> LENGTH: 788
<212> TYPE: PRT
<213> ORGANISM: Mortierella alpina

<400> SEQUENCE: 9

Met Glu Gly Asp Ala Val Arg Pro Ala Leu Ala Arg Lys Ile Pro Gly
1               5                   10                  15

Leu Tyr Ser Phe Ile Lys Leu Leu Cys Arg Thr Leu Phe His Ile Phe
            20                  25                  30

Phe Arg Asp Tyr Asp Ala Phe His Thr Gln Phe Val Pro Gln Asp Glu
```

```
                35                  40                  45
        Pro Leu Leu Val Ile Ser Asn His Gly Asn Tyr Leu Leu Asp Gly Leu
         50                  55                  60

Ala Leu Leu Ala Thr Phe Pro Gly Gln Ile Ser Phe Leu Met Ala Gln
         65                  70                  75                  80

Pro Asn Phe Lys Thr Ala Ile Gly Gly Ile Ala Arg Lys Ile Gly Ala
                             85                  90                  95

Ile Pro Val Leu Arg Pro Gln Asp Ala Ala Arg Tyr Asp Gly Ala Ser
                            100                 105                 110

Met Val Thr Ile Ala Gln Asp Gly Asn Ser Val Leu Gly Gln Gly Ile
                            115                 120                 125

Gly Lys Gln Leu Thr Leu Gly Asp Thr Val Tyr Ile Glu Cys Gly Thr
                            130                 135                 140

Phe Gln Asp Ala Gly Arg Asp Asn Arg Val Thr Gln Cys Tyr Gly Val
        145                 150                 155                 160

Val Ser Ala Ile Val Ser Asp Asn Glu Val Leu Phe Lys Ala Pro Gly
                            165                 170                 175

Leu Lys Trp Ile Pro Ala Ser Leu Thr Ser Glu Arg Asp Ile Ala Tyr
                            180                 185                 190

Ile Lys Ser Arg Lys Ile Val Arg His Gly Ser Leu Lys Ile Arg Val
                            195                 200                 205

Glu Arg Gly Asn Thr Trp Val Gly Ile Asn Glu Ala Leu Lys Ala Gln
                            210                 215                 220

Glu Gln Gln Asn Asn Gly Ser Leu Ala Ser Ser Ala Thr Gly Thr Ile
        225                 230                 235                 240

Gly Lys Phe Val His Lys Ile Phe Ser Lys Ser Pro Asp Ala Asp Ala
                            245                 250                 255

Arg Ser Asp Asp Val His Leu Ala Glu Asn Gly Tyr Ser Gly Ala Asp
                            260                 265                 270

Ile Pro Gly Ser Leu Thr Ala Pro Ala Asn Phe His Thr Thr Glu Thr
                            275                 280                 285

Thr Pro Leu Leu Lys Lys Ala Arg Ser Ser Asn Ser Ser His Pro
        290                 295                 300

Ile Tyr Thr Val Pro Lys Arg Ala Asp Ser Asn Ala Arg Leu Ser Ser
        305                 310                 315                 320

Tyr Ser Thr Thr His Ser Thr Asn Ala Val Ala Asp Ala Asn Asp
                            325                 330                 335

Asp Glu Thr Thr Arg Pro Ala Asn Gly Leu Arg Asn Ala Gln Gly Gly
                            340                 345                 350

His Asn Pro Ala Gly Thr Asn Gly Val Val Asn Gly Gly Ala Ser Thr
                            355                 360                 365

Ser Met Ser Pro Arg Ser Pro Leu Thr Ser Pro Thr Leu His Ser
                            370                 375                 380

Ser Thr Ser Ala Val Ser His Phe Pro Ser Arg Pro Cys Pro Phe Gln
        385                 390                 395                 400

Phe Ser His Pro Ile Asp His Ser Val Ile Tyr Glu Ser Val Trp Lys
                            405                 410                 415

Asn Phe Glu Asp Gly Arg Thr Val Ala Val Phe Pro Glu Gly Val Ser
                            420                 425                 430

Ser Asp Asp Tyr His Leu Leu Asp Phe Lys Tyr Gly Cys Thr Ile Met
                            435                 440                 445

Val Leu Gly Tyr Leu Ala Gln His Arg Ser Lys Thr Leu Arg Ile Ile
                            450                 455                 460
```

| | | | | | | | | | | | | | |
|---|---|---|---|---|---|---|---|---|---|---|---|---|---|
| Pro | Cys | Gly | Leu | Asn | Phe | Phe | Asn | Arg | His | Arg | Phe | Arg | Ser | Arg | Phe |
| 465 | | | | 470 | | | | | 475 | | | | | 480 |
| Tyr | Ala | Asp | Tyr | Ser | His | Pro | Leu | Thr | Val | Pro | Asp | His | Leu | Val | Glu |
| | | | | 485 | | | | | 490 | | | | | 495 |
| Met | Tyr | Arg | Glu | Gly | Gly | Glu | Ala | Lys | Lys | Gln | Ala | Cys | Thr | Glu | Leu |
| | | | 500 | | | | | 505 | | | | | 510 |
| Leu | Gln | Met | Ile | His | Ser | Ala | Val | Glu | Gly | Leu | Thr | Leu | Asn | Ala | Pro |
| | | | 515 | | | | | 520 | | | | | 525 |

```
Pro Cys Gly Leu Asn Phe Phe Asn Arg His Arg Phe Arg Ser Arg Phe
465                 470                 475                 480
Tyr Ala Asp Tyr Ser His Pro Leu Thr Val Pro Asp His Leu Val Glu
                485                 490                 495
Met Tyr Arg Glu Gly Gly Glu Ala Lys Lys Gln Ala Cys Thr Glu Leu
            500                 505                 510
Leu Gln Met Ile His Ser Ala Val Glu Gly Leu Thr Leu Asn Ala Pro
            515                 520                 525
Asn Tyr Asp Glu Leu Arg Leu Tyr Lys Ala Thr Arg Arg Leu Tyr Ser
            530                 535                 540
Thr Gly Lys Lys Leu Thr Val Pro Gln Lys Leu Glu Leu Thr Arg Arg
545                 550                 555                 560
Phe Ala Lys Gly Tyr Gln Asn Leu Val Met Thr Pro Ser Met Ala Ala
                565                 570                 575
Leu Lys Arg Asp Ile Asp Ala Tyr Asp Lys His Leu Ser Ser Ser Gly
            580                 585                 590
Val Arg Asp Ala Gln Leu Thr Ala Asn Pro Ser Ile Leu Ala Ala Leu
            595                 600                 605
Val Phe Ile Leu Pro Ala Leu Phe Leu Pro Val Leu Phe Leu Leu
610                 615                 620
Ser Leu Pro Gly Thr Leu Leu Phe Gly Pro Val Gly Leu Leu Ala Ser
625                 630                 635                 640
Trp Ala Ala Lys Gln Lys Gly Gln Gln Ala Met Leu Ala Phe Gln Ser
                645                 650                 655
Tyr Leu Pro Val Ser Arg Trp Pro Gly Arg Asp Val Ile Ala Thr Trp
                660                 665                 670
Lys Ile Val Val Ser Leu Ala Leu Met Pro Val Cys Phe Ile Leu Asp
            675                 680                 685
Ala Thr Leu Leu Thr Ile Leu Ala His His Trp Glu Ala Leu Gln Glu
690                 695                 700
Tyr Trp Thr Met Gly Arg Leu Val Ala Phe Trp Leu Leu Ser Thr Phe
705                 710                 715                 720
Val Ile Phe Pro Thr Met Ala Tyr Gly Thr Val Trp Leu Trp Glu Trp
                725                 730                 735
Gln Ile Asp Leu Lys Met Gln Ile Tyr Val Trp Trp Lys Leu Cys
            740                 745                 750
Gly Gly Asn Ala Glu Met Lys Arg Trp Arg Gln Asp Leu Val Glu Arg
            755                 760                 765
Met Asp Ala Leu Val Glu Arg Met Gly Gly Arg Arg Val Phe Asp Val
770                 775                 780
Ser Gly Tyr Tyr
785
```

<210> SEQ ID NO 10
<211> LENGTH: 2367
<212> TYPE: DNA
<213> ORGANISM: Mortierella alpina

<400> SEQUENCE: 10

| | |
|---|---|
| atggaaggag acgcagtacg gcctgctttg ccagaaaga tccctggtct ctacagcttc | 60 |
| atcaaactcc tttgcaggac gcttttcac atcttcttca gggattacga cgcctttcat | 120 |
| acccagtttt ttccacagga cgaaccattg ctagttatct ccaaccatgg caactacctt | 180 |
| ctggatggcc tcgccttgtt ggccaccttt ccaggccaga tctccttttt gatggcacag | 240 |

```
cccaattttca agactgcaat tggtggcatc gccaggaaga ttggtgccat tccagtactg    300
agaccacagg acgcggccag atatgacggt gcgagtatgg tcacaatcgc tcaggatggc    360
aactcagtcc tcggtcaggg gattggcaag cagctgactt tgggcgatac tgtctatatc    420
gagtgtggga cgttccagga cgctggcagg acaatcgcg tcacgcaatg ttatggcgtg     480
gtcagtgcga tcgtcagtga caacgaggtg ttgttcaagg ctcccggttt gaaatggatt    540
cccgcatcct tgacatcgga acgcgacatt gcctatatca atcgcgaaa gattgttcgg     600
catgggtcac tcaagatcag agtggaacgt ggcaacacct gggtcggaat caatgaggcg    660
cttaaagcac aggagcagca gaacaatggc tcgttggcaa gcagcgcaac ggggacgatc    720
ggcaagtttg ttcacaagat atttttcaaag tcgccggatg cagacgcaag atcagatgat   780
gtgcatttgg ccgagaatgg gtattccgga gcagatatcc ccgggtcctt gaccgctcca    840
gccaactttc acacaactga gactacacca ctactcaaaa aggcgcgctc gtcaaacagc    900
tccagtcatc ctatatacac agtaccaaag cgcgcagact cgaacgcgag ctttcatca     960
tactctacca ctcacagcac aaatgcagtg gccgatgccg acaacgacga cgagaccacg   1020
cgccctgcaa atggacttag gaacgcgcaa ggcggacaca ccccgctgg aaccaatggc   1080
gttgtcaatg gaggcgcatc cacatccatg agcccacgaa gcactccatt gacctcccct   1140
acacttcaca gctccacatc ggccgtgtca cacttcccct cgcgaccctg ccccttccag   1200
ttctcacacc caatcgacca ttctgtgatc tacgagagcg tctggaagaa ctttgaggat   1260
ggtcgcaccg ttgctgtatt ccctgaaggc gtatcgagcg acgattatca cttgctcgac   1320
ttcaaatatg gctgcaccat catggttctt ggatacctgg ctcagcatcg ctctaagact   1380
ctaaggatta taccatgcgg actgaacttc tttaatcgcc atcgatttcg atcccggttc   1440
tacgccgact actcccatcc gctcaccgtc cccgaccacc ttgtagagat gtatcgcgaa   1500
ggaggagaag ccaagaagca agcctgtact gagcttctgc agatgattca ctcggctgtg   1560
gagggctga ctcttaacgc accaaactac gacgagctgc gactttacaa ggcaacgcga    1620
cgactctaca gcactgggaa gaagcttacc gtgccacaga aattggagct aactcgccgt   1680
tttgcgaaag gttatcaaaa tctggtcatg acgccgagca tggctgcatt gaaacgcgac   1740
attgatgctt atgacaagca tctctccagc agcggcgtcc gagacgcaca actgaccgca   1800
aacccaagca ttctggctgc ccttgtattc atattgcccg cgttattcct cttgccagtg   1860
ctgttcctgc tttcgttacc cgggacgttg ctcttcggac ctgttggact tttggcgtcg   1920
tgggcggcaa agcagaaagg acagcaggcc atgcttgcct tcagtctta tctcccagtt    1980
tcacgttggc ctggccgaga tgtgatcgcc acctggaaga tcgtggtgtc cttggcgttg   2040
atgcccgtct gctttattct ggacgcaaca ctgctcacga tcctagcaca ccattgggaa   2100
gcactgcagg agtactggac tatgggtcgt ctagttgcgt tctggctgct gtcaacattt   2160
gtgattttc caacgatggc gtatggtacg gtctggcttt gggagtggca gattgatttg    2220
aagatgcaga tctatgtatg gtggtggaag ctctgcggag gcaatgcaga gatgaagcgc   2280
tggagacagg atcttgtcga gagaatggat gcacttgtcg aaaggatggg cggtagaagg   2340
gtgtttgatg tatcgggcta ttattga                                       2367
```

<210> SEQ ID NO 11
<211> LENGTH: 2632
<212> TYPE: DNA
<213> ORGANISM: Mortierella alpina

<400> SEQUENCE: 11

```
gtttgtctct cgacctttcg tcatcactct ctcgtcgtca tcccagccag cctttttgctt      60
cttttttcatt tctttgccgc atggactaac ggctgacact ctcacgccct ctcctccatc     120
gcaaagtatt tcttgcactg cttgccctgt ttttaatcga ctcctcgtca agcaatcacc     180
tccagcggat cccaggtggc cgcagcccta taccccaact gccaatggaa ggagacgcag     240
tacggcctgc tttggccaga agatccctg gtctctacag cttcatcaaa ctcctttgca     300
ggacgctttt tcacatcttc ttcagggatt acgacgcctt tcatacccag tttgttccac     360
aggacgaacc attgctagtt atctccaacc atggcaacta ccttctggat ggcctcgcct     420
tgttggccac ctttccaggc cagatctcct ttttgatggc acagcccaat ttcaagactg     480
caattggtgg catcgccagg aagattggtg ccattccagt actgagacca caggacgcgg     540
ccagatatga cggtgcgagt atggtcacaa tcgctcagga tggcaactca gtcctcggtc     600
aggggattgg caagcagctg actttgggcg atactgtcta tatcgagtgt gggacgttcc     660
aggacgctgg cagggacaat cgcgtcacgc aatgttatgg cgtggtcagt gcgatcgtca     720
gtgacaacga ggtgttgttc aaggctcccg gtttgaaatg gattcccgca tccttgacat     780
cggaacgcga cattgcctat atcaaatcgc gaaagattgt tcggcatggg tcactcaaga     840
tcagagtgga acgtggcaac acctgggtcg gaatcaatga ggcgcttaaa gcacaggagc     900
agcagaacaa tggctcgttg gcaagcagcg caacggggac gatcggcaag tttgttcaca     960
agatattttc aaagtcgccg gatgcagacg caagatcaga tgatgtgcat ttggccgaga    1020
atgggtattc cggagcagat atccccgggt ccttgaccgc tccagccaac tttcacacaa    1080
ctgagactac accactactc aaaaaggcgc gctcgtcaaa cagctccagt catcctatat    1140
acacagtacc aaagcgcgca gactcgaacg cgaggctttc atcatactct accactcaca    1200
gcacaaatgc agtggccgat gccgacaacg acgacgagac cacgcgccct gcaaatggac    1260
ttaggaacgc gcaaggcgga cacaaccccg ctggaaccaa tggcgttgtc aatgaggcg    1320
catccacatc catgagccca cgaagcactc cattgacctc ccctacactt cacagctcca    1380
catcggccgt gtcacacttc ccctcgcgac cctgcccctt ccagttctca cacccaatcg    1440
accattctgt gatctacgag agcgtctgga agaactttga ggatggtcgc accgttgctg    1500
tattccctga aggcgtatcg agcgacgatt atcacttgct cgacttcaaa tatggctgca    1560
ccatcatggt tcttggatac ctggctcagc atcgctctaa gactctaagg attataccat    1620
gcggactgaa cttctttaat cgccatcgat ttcgatcccg gttctacgcc gactactccc    1680
atccgctcac cgtccccgac caccttgtag agatgtatcg cgaaggagga gaagccaaga    1740
agcaagcctg tactgagctt ctgcagatga ttcactcggc tgtggagggg ctgactctta    1800
acgcaccaaa ctacgacgag ctgcgacttt acaaggcaac gcgacgactc tacagcactg    1860
ggaagaagct taccgtgcca cagaaattgg agctaactcg ccgttttgcg aaaggttatc    1920
aaaatctggt catgacgccg agcatggctg cattgaaacg cgacattgat gcttatgaca    1980
agcatctctc cagcagcggc gtccgagacg cacaactgac cgcaaaccca agcattctgg    2040
ctgcccttgt attcatattg cccgcgttat tcctcttgcc agtgctgttc ctgctttcgt    2100
taccgggac gttgctcttc ggacctgttg acttttggc gtcgtgggcg gcaaagcaga    2160
aaggacagca ggccatgctt gcctttcagt cttatctccc agtttcacgt tggcctggcc    2220
gagatgtgat cgccacctgg aagatcgtgg tgtccttggc gttgatgccc gtctgcttta    2280
ttctggacgc aacactgctc acgatcctag cacaccattg ggaagcactg caggagtact    2340
```

-continued

| | | |
|---|---|---|
| ggactatggg tcgtctagtt gcgttctggc tgctgtcaac atttgtgatt tttccaacga | 2400 |
| tggcgtatgg tacggtctgg ctttgggagt ggcagattga tttgaagatg cagatctatg | 2460 |
| tatggtggtg gaagctctgc ggaggcaatg cagagatgaa gcgctggaga caggatcttg | 2520 |
| tcgagagaat ggatgcactt gtcgaaagga tgggcggtag aagggtgttt gatgtatcgg | 2580 |
| gctattattg agcaacgttc atgtataaag tcatttggcc caattcttct cc | 2632 |

<210> SEQ ID NO 12
<211> LENGTH: 2598
<212> TYPE: DNA
<213> ORGANISM: Mortierella alpina

<400> SEQUENCE: 12

| | | |
|---|---|---|
| atggaaggag acgcagtacg gcctgctttg gccagaaaga tccctggtct ctacagcttc | 60 |
| atcaaactcc tttgcaggac gcttttttcac atcttcttca gggattacga cgcctttcat | 120 |
| acccagtttg ttccacagga cgaaccattg ctagttatct ccaaccatgg caactacctt | 180 |
| ctggatggcc tcgccttgtt ggccaccttt ccaggccaga tctccttttt gatggcacag | 240 |
| cccaatttca agactgcaat tggtggcatc gccaggaaga ttggtgccat tccagtactg | 300 |
| aggcaagtct ttgaaaaacc acaaaataca gagcgaaata gtgaccatag gctcgacata | 360 |
| tggggtggcg tgatctgcgc atcctgtctt ttcgtcaacc cttttgctt tgcccacttg | 420 |
| ctgaccctgt gattatgctc tttgtccaat ctatagacca caggacgcgg ccagatatga | 480 |
| cggtgcgagt atggtcacaa tcgctcagga tggcaactca gtcctcggtc aggggattgg | 540 |
| caagcagctg actttgggcg atactgtcta tatcgagtgt gggacgttcc aggacgctgg | 600 |
| cagggacaat cgcgtcacgc aatgttatgg cgtggtcagt gcgatcgtca gtgacaacga | 660 |
| ggtgttgttc aaggctcccg gtttgaaatg gattcccgca tccttgacat cggaacgcga | 720 |
| cattgcctat atcaaatcgc gaaagattgt tcggcatggg tcactcaaga tcagagtgga | 780 |
| acgtggcaac acctgggtcg gaatcaatga ggcgcttaaa gcacaggagc agcagaacaa | 840 |
| tggctcgttg gcaagcagcg caacggggac gatcggcaag tttgttcaca agatattttc | 900 |
| aaagtcgccg gatgcagacg caagatcaga tgatgtgcat ttggccgaga atgggtattc | 960 |
| cggagcagat atccccgggt ccttgaccgc tccagccaac tttcacacaa ctgagactac | 1020 |
| accactactc aaaaaggcgc gctcgtcaaa cagctccagt catcctatat acacagtacc | 1080 |
| aaagcgcgca gactcgaacg cgaggctttc atcatactct accactcaca gcacaaatgc | 1140 |
| agtggccgat gccgacaacg acgacgagac cacgcgccct gcaaatggac ttaggaacgc | 1200 |
| gcaaggcgga cacaaccccg ctggaaccaa tggcgttgtc aatggaggcg catccacatc | 1260 |
| catgagccca cgaagcactc cattgacctc ccctacactt cacagctcca catcggccgt | 1320 |
| gtcacacttc ccctcgcgac cctgcccctt ccagttctca cacccaatcg accattctgt | 1380 |
| gatctacgag agcgtctgga agaactttga ggatggtcgc accgttgctg tattccctga | 1440 |
| aggcgtatcg agcgacgatt atcacttgct cgacttcaaa tatggctgca ccatcatggt | 1500 |
| tcttggatac ctggctcagc atcgctctaa gactctaagg attataccat gcggactgaa | 1560 |
| cttctttaat cgccatcgat ttcgatcccg gttctacgcc gactactccc atccgctcac | 1620 |
| cgtccccgac cacttgtag agatgtatcg cgaaggagga gaagccaaga agcaaggtaa | 1680 |
| ggaagaccaa aactgcctcc ctcacatatc gcagtctgtc gaagttttc tcacatatct | 1740 |
| ctttttctct tagcctgtac tgagcttctg cagatgattc actcggctgt ggaggggctg | 1800 |

```
actcttaacg caccaaacta cgacgagctg cgactttaca aggcaacgcg acgactctac   1860
agcactggga agaagcttac cgtgccacag aaattggagc taactcgccg ttttgcgaaa   1920
ggttatcaaa atctggtcat gacgccgagc atggctgcat tgaaacgcga cattgatgct   1980
tatgacaagc atctctccag cagcggcgtc cgagacgcac aactgaccgc aaacccaagc   2040
attctggctg cccttgtatt catattgccc gcgttattcc tcttgccagt gctgttcctg   2100
ctttcgttac ccgggacgtt gctcttcgga cctgttggac ttttggcgtc gtgggcggca   2160
aagcagaaag gacagcaggc catgcttgcc tttcagtctt atctcccagt tcacgttgg    2220 cctggccgag atgtgatcgc cacctggaag atcgtggtgt ccttggcgtt gatgcccgtc   2280
tgctttattc tggacgcaac actgctcacg atcctagcac accattggga agcactgcag   2340
gagtactgga ctatgggtcg tctagttgcg ttctggctgc tgtcaacatt tgtgattttt   2400
ccaacgatgg cgtatggtac ggtctggctt tgggagtggc agattgattt gaagatgcag   2460
atctatgtat ggtggtggaa gctctgcgga ggcaatgcag agatgaagcg ctggagacag   2520
gatcttgtcg agagaatgga tgcacttgtc gaaaggatgg gcggtagaag ggtgtttgat   2580
gtatcgggct attattga                                                 2598
```

<210> SEQ ID NO 13
<211> LENGTH: 3087
<212> TYPE: DNA
<213> ORGANISM: Mortierella alpina

<400> SEQUENCE: 13

```
atggcccttc agatctacga cttcgtgtcg ttcttcttca ctatcctgct cgacatcttc     60
ttcagggaga ttcgtcccag aggcgcacac aaaattccac aaaaaggacc cgtgatcttt   120
gttgccgctc ctcatgccaa tcaggtacgt gcacatgagg gctcgctttt ctcggagcgg   180
gcttcgtcca aaaagctgca caggctgaaa tgagagcgca tattcacctg gacacgggca   240
cagagttcat gcatgataag ccggatagca ggagccgaca ctgcagaaga gaccctctgg   300
accaacaaag aaaaacatca tgacggaact agccttctcc ggaagagcca atggacgtca   360
ttggtagacg caaccgttcc aactaaccgg cgctcttgtc ctcatagttt gtcgatcctc   420
tcgtcttgat gcgtgagtgt ggccgtagag tctcattcct tgcggccaaa aagtctatgg   480
accgccggtg gattggtgct atggcacgct cgatgaatgc gagtaagttg cttggacttt   540
gacacgaaac tgttgccacg tcaagaatat tcccaccctc ccgactcgac cacctccagc   600
tctcacctac acacacaaaa caggaaattt cagtgttctt caaggctttg gtggtgcttc   660
gaatggcgct acaaaaggcc tgctctaggg tgatagagtg ttggctttga tccttccgac   720
attctcggct cccttaccaa gacatttgtc ctgaatgctg attgatccga cactgctgaa   780
ccattcctac tcatagttcc tgttgaacgc ccgcaggatc ttgctaaagc gggttcggga   840
gtcatcaaac ttttggatcg ctatggtgat cctcttcgag tgacaggtgt cggcactaaa   900
ttcacaaagg agctacttgt gggagatcag atatctctcc caaggacgt tggctcctca    960 gccgtggtcg agatcatatc tgataccgag ctgattgtca agaaggaatt caaggagctc  1020
aaggccctcg aattattgac cagccctgat ggaaccaagt ataaatgcct acctcacatg  1080
gaccagacga atgtatacaa aactgtcttt gagcgcctca cgctggaca ttgcgttggc   1140 attttccccg aaggtggatc ccacgatcgc gctgagatgc tgccattgaa aggtacgtgt  1200
gctcgtgctt ctgcacagag cagagtagtt gatatggaac agaagaaaaa agacacgcga  1260
ccagctttga ttaacagcca cgtgtttcct ttacctttgc gaaacattat agctggagtc  1320
```

```
accatcatgg ctctgggcgc gttggccgcc aacccttcgt tggacctcaa gattgtcacc    1380
tgcggcctca actactttca tcctcatcgc ttccgctcgc gtgcagtggt cgagtttggc    1440
gagccactga cggtccctcc tgagctggtc gaaatgtaca agcgaggcgg ggctgagaag    1500
cgtgaagcgt gcggaaagtt gctggataca atctatgagg ctcttcgcgg tgtcactctc    1560
aatgcacctg attacgaaac gttgatggta tggagcaaag gaccatagcg tggatgaagg    1620
aggacgtgga aaggacaagc accgctcaca gatttctcac tcttgtattt gtgattatct    1680
ctaggtcatt caagcggccc gtcgccttta caagcccact catcgcaagc tgcagatctc    1740
acaagtcgtg gagttgaacc gcaggttcgt cgcaggatac atgcacttca aggacaaccc    1800
taaagtcatt gaagccaagg acaaggtcat gcattacaac actcaacttc gataccatgg    1860
actgcgcgat catcaggtga acattcgcac aaccaggaaa cacgctatcg gcatgctcat    1920
ctcacggctc attcagatga tcttttttgag ttgtctggct ctacctgggt aagcacagct    1980
tgaatctcga ccaggtcccg caatgatccc attgcggaga agtcactgac gcttgctctt    2040
cccgtgcttt tttgaataga accctgatga atcttccggt cgctattgtc gctcgtgtca    2100
tcagcaacaa gaaggccaaa ggtacgcctt gcggtttgtt atcttttcgt gtttgctttt    2160
gtgctcgcca ctggaaacta atatttctac atcactctgc aactggtaga ggcgctggct    2220
gcctcgacag tcaagattgc tggaagggat gtcctggcta catggaagct gctggtcgct    2280
ctaggattga tgcctgtcct ctacttcaca tattccgtca tggtctttat ctattgtggc    2340
cgcttcgaca tatcgttcaa gtcgcgtctc ttgatcgctt gggcagcatg ggcgctaatt    2400
cctttcgtaa cgtatgcaag catacgcttc ggtgaagttg gtatcgatat tttcaaatct    2460
atccgcccat tgttcttgtc catcatccca ggtgaagaga gcacgatcaa cgacttgcgc    2520
aaagcccgag cggaactcca gaagactatc accaatctta tcaatgagct ggcgccgcag    2580
atttatcccg actttgattc gaagcgcatc ctcgatccgt ctcctgcaga tcgccccagc    2640
cgctcggcat caggtaccaa ccttgcacag acaatcttca acacggccgc tcagcctttg    2700
aaccaatggc taggcaagga cggccgcttt gaatgggagc gcaccgagga ttcggatgca    2760
gatgatgtgt tcttcttttt ggacccagca agaggaattc ttggacggtc gagggcgtcg    2820
tcctggggag gagggcatt tacacctgcc gccgatgggt cgcgatcccg gaatcggagc    2880
aggacaagca gcttcacgtc gggacagatc cagcttggcg agggcttcaa actcgaggca    2940
ttgacggaac tgccgaggga caagccttt gcagaggtga cgaggcggct gagtgtgagc    3000
cgcatgcaga gatacgggtt ggagggtatg acgcgctcgg acacggacga aaacgaaggc    3060
tctacagcca agtcaaaaga tatctag                                        3087

<210> SEQ ID NO 14
<211> LENGTH: 3280
<212> TYPE: DNA
<213> ORGANISM: Mortierella alpina

<400> SEQUENCE: 14
atgggtctcc agatctatga cttcgtctca ttcttcttca ccctcctgct cgacatcttc      60
ttcagggaaa tccgtcctcg ggggccccac aagatccccc gacaaggacc cgtcattttt     120
gtcgccgccc ctcatgccaa tcaggtaggc cattgtcttt aatttggaag cttaaagtca     180
ccactttatg cgcaagagcc tcatggtccg taaggtacta atcgctgctt gcatgaaact     240
agtttgttga tccactcgtg ttgatgcgcg aatgtggccg acgagtctcg ttcctggctg     300
```

```
ccaaaaagtc aatggaccgt cgctggatag gcgccatggc gcgttccatg aatgccagta    360
agtacaaaaa aaaaaaaaaa aaaaaaaaaa aacgacctat tcggcgtgag agtggcaacg    420
aaggggagag agatacacaa acgggccttt tgagtgcgtg tgtgcgtggg aaaagaatac    480
gagaacattc tcttgccagc aaaacgcgct tcctttctct tttctccgac gttgttgatg    540
gcgccttttg tatacacttc ctatccatcg tccctatccg agagatcaag gttttctgcg    600
tcgtgttatt ttaggccact ccgccgagat aacagacacg agctactgac cgattcaacg    660
agggttcaca caccgtccac aaccacctga gaaatgtgca ggccatgacg agtgtcgtgt    720
gccgtttctt ctttgatacc ataccgctcc tgcagtcatg gccatccgt tatgccctga     780 cctcagcatt ggaatctgac gttttttttct gctcgctctc ttgtcatctg cgttagttcc    840
tgtggagcgt cctcaggact tggctaaggc tggttcggga acgatcaaac tggtggatcg    900
ctatggcgac cctctccgca tcactgggct cggtaccaaa ttcacaaagg aactctttgt    960
cggcgaccag atttcgctcc caaggacgt tggaacctcg gctgtggtcg agatcatctc    1020
ggacactgaa ctgattgtca agaaagagtt caaggagctc aaggcactgg agcttttaac    1080
cagtgctgag ggatccaagt acaagtgcat gcctcacatg gaccagagca aggtctacaa    1140
gactgttttt gaacgcttaa atgctggcca ttgtgttggc atcttcctg aaggaggttc     1200 acacgatcgt gcagagatgc tgcccctgaa aggtaagcgc ccctcgtgag catcccaaca    1260
taacgggaat taccccacac ttgccttgtc cttgcgcatc tctgtatgaa cgtacactga    1320
ttgcattgca tatctccgtt tggattggat agctggtgtc accatcatgg cgcttggcgc    1380
actggccgct aaccctgacc tggaccttaa aattgtgacc tgcggcctga actatttcca    1440
cccccatcga ttccgttctc gcgccgttgt tgagtttggt gagcctttga ccgtgcctcc    1500
agaacttgtc gagatgtaca agagggggtgg agctgagaag cgcgaggcct gcggaaagct    1560
cctcgacacc atctacgatg cactcaagaa tgtcacactg aacgcccccg attacgaaac    1620
actcatggtg aggattggcg tgttttttgc atgcggctta tgtcatttgg agcaattgag    1680
accaacgtta acttaaaggg ctttaatatg gctggactgg atgtaggtta ttcaagctgc    1740
ccgccgtctc tacaagccaa cacatcgcaa gctgcagatc tctcaagttg tggagttgaa    1800
ccgtcgcttc gtcgctggtt atctgcactt tcaggacaac ccaaaggtga ttgatacaaa    1860
ggacaaagtt atgcactaca acactcagct acgctatcat ggacttcgcg accaccaggt    1920
caacatccgc acaactcggc gacatgccat tgaactattg atttggcgag ttgtgcagat    1980
ggtctttttg agtctactag cgcttccagg gtaagaacga atgcagcagt ggtgtcatgt    2040
cacagacttt tgtgtgggcg gttagattga ggctagcact acttcacgcg attggatatt    2100
agactaacgc tttctctact tttagtacca tgatgaatct tccagttgcc atcgttgctc    2160
gcatcatcag caacaagaag gccaagggta tgtaatcgtc gcaatgacag cgacaaatct    2220
tttgattatc gggagaatgg cgtcagagga aaaaggccaa ggctaacgct ataatcattt    2280
tcacaattta acagaggctt tggctgcatc gaccgtgaaa attgcaggaa gggacgttct    2340
agccacatgg aagttgcttg tggccctggg attgatgccc gtcctttact tttcgtactc    2400
gtttgttatc ttttttgctgt gtggacggtt cgacattacg ctcaagaccc gcctcctgat    2460
cgcttgggcg gcttgggcct gcattccgtt tgtgacctac gccagtatcc gtttcggtga    2520
ggtgggtatc gatatcttca agtcgatccg tcctctcttc ttgtcaatca ttcccggcga    2580
ggaaaacacg atcaatgagc tccgcaagtc gcgtgcagag cttcaaaaga ccatcaacga    2640
gctcatcaat gagctggcgc cggaaatata ccccgacttt gattccaaac gaatcttgga    2700
```

```
ccccttcgcca aacgatcgac ccagccgcgg cgcgtcgcgc tccgcctcgg gcaccaacct    2760
tgcgcagacc attttcaaca ccatgaacac ggccacacag ccgctaaacc aatggctcgg    2820
tatggatggg cgcttcgagt gggagcgtgt ggacgactcg gatgcggacg acgtgttctt    2880
tttcctcaac cctgcaggag ccatccaagg gcgatcgagg acgtcttctt ggggtgctgg    2940
agcatggacg ccttcgtctg ctggcgatgg ttctcggtct cggtcaagga gtcgcagtcg    3000
gacgagctcg tttgcgtcag ggcagattca gctgggcgaa gggttcaagc tggaggcatt    3060
gacagagctg ccaaaggata agccttttgg cgaggtgaca cgacgactca gcttgagtcg    3120
caagcagaag catggactgg tgggcgacat gaccaaggat cccgaggaga ttgagaagca    3180
gggcggattt atgcatgagg gacactttgt cagcacaccg cccatcacgg ttcagaacat    3240
ggatgatcct atggatgcag tcaagtctaa ggaggcataa                          3280

<210> SEQ ID NO 15
<211> LENGTH: 2896
<212> TYPE: DNA
<213> ORGANISM: Mortierella alpina

<400> SEQUENCE: 15
atggccaaac ttcggaagcg gacctcccag tcaaaggagg cgccgctga caccaacggc      60 acaaggcgag acagcgtcga tgacacgaac agcgtcggca gctacgatcc acgcccctc     120 tccaacgatc caccaaagat gtacagggcg atccggttct tcttcaagat gtgcctgcac    180
tccttctatg gccatgtgga ggtcgagggc accgagaata ttgcaccaaa caactaccct    240
gctatccttg gtaacgttct taggacaaat attcctttgc aggatgatca cacattatgt    300
catggccttt ggtcttgaaa tgttagtcta accgttcgga tgcacactcg tcgatagttg    360
cgaaccacag caacagtttg acggatgcga ttgccattat gtcgactgtt cctcccaaga    420
gcaggagcat gattaggatg accgcaaagg acacgttttg gcataagcca ggcgtcttca    480
agtatgcact gccagcctag cctgaacaca cctcgtccga tgcctccttt cactgaccgg    540 atatctttt tgtctttgaa tggcgcgccc tcctcgtgca ctcttcgtct ccttctccgt     600
tattgatagt tatgtcatca aaaacgctgg cactgtcccg atcaaaagac gcaaggatta    660
tgagaaccaa aaggtcgaca cactgacgc gatgggtgca ttgatcgata cccttggagc     720
aggaagttgt gtatggtaag tggagggtcc ttgtctgcat accgcgctgc acttgaaggc    780
tttctacact tccaatgaca gggatagctg cactgcatgt tgattgtaa agcgtaacat     840 agagagaaga gggggaagag ggggtgggga aaactgaatc aatatcaagg accatatgaa    900
tatgattcaa agcactggtt gcaatgctgt gttgttttgc atgaaaaacg cagctccttg    960
cctcgactca cccctgcatc ttcatatacc accttccaac cgcaaaaaaa aatcaaagca   1020
tgttcccgga gggcatctcg cgctatcacc cacaacttgc tccgttcaag gccggtgtcg   1080
ccatgattgc cagcgatgta agtgttcgct tgatgaactt ttattatttt tgacgttccg   1140
accgtgctgg ctcctcgcga ctgcaactgt gatttgtcat ggcaaatacc acagcgctct   1200
cactgacatg aattttcatg ctctctttca cgctcctctg tctctcatgc ttgccctaat   1260
attcttttgt acacgaccga tgatacacga ccgatgatac acgacggggg ggtttctcgg   1320
tttgcgacat tgtgccatgg atgtgtttgt ctcaattaga cgctctcccg gtttcaagac   1380
acgcccgatt tttctctcac gctcatgaca gcgtcgatca actatcttca ccgtgaaaag   1440
ttccgatctg atgttctcgt cacgttccat gcacccattg tgctaacccc gcaacaagac   1500
```

```
tcgaagctgt tttcgactga cctggaagtc aagaaggaag cgatccgaaa actgacagag    1560
ttgctcgagg gcaccgtccg atcaactcta ctggatgccg aggactggca aacagtccga    1620
gtgggtcatg ttgccaggaa gctctatgct ggcgatctgg gaactcggat ttcgctggga    1680
cagtacgtgc gttttgaccag gaagtttgtc acggcgttca gtcagcacaa gcaggaggag    1740
gaggcagcgg tcgatgacga gcgttatggt caggagaagc acggggcgg tgccgagagg     1800 aatggtgatt ctttggagat gaggcatcct gagcgcatgg ataaggcgac tagaaagaaa    1860
atcgacgagc tcgccaggga tttggctgta agcatgagta attcattcag tcgtctcaca    1920
cacggcatgc tctttcaaaa gtggacgcta acggatacat tattcttatt tttatttcct    1980
tgacggtgat cataacagga ctaccaaaac cagctggact tctatcacct caaggactat    2040
cgtatcaagc aaggcaagcc aagtgcaaag attcttatcg gacgtctttt ccaaagattc    2100
ttgcttgctt gccttttgtc gaccatttgc attcctggac tgttcctttg ggcacctgtg    2160
tttatcgccg tgaagtacgc aagacattgg gttgacactg ataccttgcc aacaattaag    2220
cacgaactct ccttctcgat acctgctatt tttaacactg atgtaatcgt ctctttttt     2280 ttctctctag gtacaaagag agtcagctta ggcgcaaggg acccttggag gacaacttgg    2340
atgaaattgc ccagtacaag ttgatgatct cgactttctt cttgccgatc atctgggggt    2400
tctggatcgt aatgaccttg ccaattgcgc tctttagcgc gccgggcatc gttgttctga    2460
tgtggctgta agtcaagaga ggaagaagat gcatatcaag acctttttcaa gttatcaaga    2520 cactatgact attgctgcga cgaagactaa cttatatttc cattgtgcgt gtgatagtac    2580
gatccgctgg cttgaggact tgatccacaa cgcgaaatcg atgttgtccc ttttgcgatt    2640
gctgtttatg acggaggata ccatgtactc gttgagagac taccgtcagg ggctggcgca    2700
tcgtgtgcac gattttgcgg tcgatcatct gaagttgcct gaggaccctg aggttctggt    2760
caaggagaac aagaccaaga aggtcgacag tggctggatg ggcaagttgt cgggcagcta    2820
cttctcgatc aagaggagaa gaagaaagga ctgaacgag gttatgcgat tgcacgatgt    2880
ttctcactat gactga                                                    2896
```

<210> SEQ ID NO 16
<211> LENGTH: 29
<212> TYPE: DNA
<213> ORGANISM: Artificial sequence
<220> FEATURE:
<223> OTHER INFORMATION: primer GPAT4-S

<400> SEQUENCE: 16
caaggatgtt gttgatgagg aaggcgaag                                          29

<210> SEQ ID NO 17
<211> LENGTH: 28
<212> TYPE: DNA
<213> ORGANISM: Artificial sequence
<220> FEATURE:
<223> OTHER INFORMATION: primer SacI-GPAT41

<400> SEQUENCE: 17
gagctcatgc ccatcgttcc agctcagc                                           28

<210> SEQ ID NO 18
<211> LENGTH: 29
<212> TYPE: DNA
<213> ORGANISM: Artificial sequence
<220> FEATURE:
<223> OTHER INFORMATION: primer Sal-GPAT4-2

-continued

<400> SEQUENCE: 18
gtcgacttat aatttcgggg cgccatcgc                              29

<210> SEQ ID NO 19
<211> LENGTH: 28
<212> TYPE: DNA
<213> ORGANISM: Artificial sequence
<220> FEATURE:
<223> OTHER INFORMATION: primer GPAT5-1F

<400> SEQUENCE: 19
ttccctgaag gcgtatcgag cgacgatt                               28

<210> SEQ ID NO 20
<211> LENGTH: 24
<212> TYPE: DNA
<213> ORGANISM: Artificial sequence
<220> FEATURE:
<223> OTHER INFORMATION: primer GPAT5-3R

<400> SEQUENCE: 20
caaatgttga cagcagccag aacg                                   24

<210> SEQ ID NO 21
<211> LENGTH: 835
<212> TYPE: PRT
<213> ORGANISM: Chaetomium globosum

<400> SEQUENCE: 21

Met Ala Pro Asp Asp Arg His Asp Ser Ala Pro Asp Leu Arg Ile Leu
1               5                   10                  15

Gly Asp Arg Ile Thr Leu Gln Pro Ser Gly Phe Val Glu Pro Glu His
            20                  25                  30

Thr Gly Glu Gly Lys Glu Glu Ala Leu Met Lys Asn Met Ala Arg Phe
        35                  40                  45

Arg Ser Glu Pro Leu Arg Phe Leu Arg Glu Val Ser Leu Tyr Val Ser
    50                  55                  60

Gly Thr Gly Trp Arg Ala Tyr Asp Asn Val Ile Gly Gln Pro Ile Phe
65                  70                  75                  80

Tyr Ser Gly Phe Ser Glu His Ile Lys Thr Glu Met Met Ser Ala Thr
                85                  90                  95

Leu Leu Gln Thr Lys Ile Ala Gln Leu Ala Asp Met Arg Val Ala Val
            100                 105                 110

Glu Glu Lys Glu Gly Leu Leu Asn Gly Ser Asp Ser Asp Leu Ala Ala
        115                 120                 125

Lys Lys Ala Arg Arg Arg Ala Ala Leu Val Gln Asn Leu Gln Glu Val
    130                 135                 140

Ala Glu Lys Leu Ala Asp Asn Met Ile Cys Lys Phe Asp Ser Lys Pro
145                 150                 155                 160

Phe Ile Arg Gly Ala Tyr Tyr Leu Val Thr Gln Leu Leu Leu Arg Ala
                165                 170                 175

Tyr His Gln Gly Ile His Val Ser Ser Glu Glu Val Leu Arg Leu Arg
            180                 185                 190

Ser Val Ala Glu Glu Ala Ala Arg Lys Lys Gln Ser Ile Ile Phe Leu
        195                 200                 205

Pro Cys His Arg Ser His Val Asp Tyr Val Ser Leu Gln Leu Leu Cys
    210                 215                 220

-continued

```
Tyr Arg Leu Gly Leu Ala Leu Pro Val Val Ala Gly Asp Asn Leu
225                 230                 235                 240

Asn Phe Pro Val Val Gly Ser Phe Leu Gln His Ala Gly Ala Met Tyr
            245                 250                 255

Ile Arg Arg Ser Phe Gly Asp Asp Gln Leu Tyr Ser Thr Leu Val Gln
                260                 265                 270

Thr Tyr Ile Asp Val Met Leu Gln Gly Gly Tyr Asn Leu Glu Cys Phe
        275                 280                 285

Ile Glu Gly Gly Arg Ser Arg Thr Gly Lys Leu Leu Pro Pro Lys Phe
290                 295                 300

Gly Ile Leu Asn Phe Val Leu Asp Ser Leu Leu Ser Gly Arg Val Glu
305                 310                 315                 320

Asp Ala Ile Ile Cys Pro Val Ser Thr Gln Tyr Asp Lys Val Ile Glu
                325                 330                 335

Thr Glu Gly Tyr Val Thr Glu Leu Leu Gly Val Pro Lys Lys Lys Glu
            340                 345                 350

Asn Leu Ala Asp Phe Leu Thr Gly Gly Ser Ser Ile Leu Ser Leu Arg
        355                 360                 365

Leu Gly Arg Val Asp Val Arg Phe His Glu Pro Trp Ser Leu Arg Gly
370                 375                 380

Phe Ile Asp Glu Gln Leu Ser Arg Leu Ser Lys Met Pro Ser Ala Ile
385                 390                 395                 400

Asn Val Asp Trp Arg Asp Met Lys Asn Gln Met Leu Arg Gln Lys Leu
                405                 410                 415

Leu Arg Thr Leu Gly Tyr Lys Val Leu Ala Asp Ile Asn Ala Val Ser
            420                 425                 430

Val Val Met Pro Thr Ala Leu Ile Gly Thr Val Leu Leu Thr Leu Arg
        435                 440                 445

Gly Arg Gly Val Gly Arg Arg Glu Leu Ile Leu Arg Val Glu Trp Leu
450                 455                 460

Thr Asn Arg Val Arg Ala Lys Gly Gly Arg Val Ala His Phe Gly Asn
465                 470                 475                 480

Ala Pro Leu Ser Asp Val Val Gln Arg Gly Leu Asp Val Leu Gly Lys
                485                 490                 495

Asp Leu Val Gly Val Val Glu Gly Leu Pro Glu Pro Thr Tyr Tyr Ala
            500                 505                 510

Val Asp Arg Phe Gln Leu Ser Phe Tyr Arg Asn Met Thr Ile His Leu
        515                 520                 525

Phe Ile Ser Glu Thr Leu Val Ala Thr Ala Leu Tyr Thr Lys Val Lys
530                 535                 540

Gln Gly Gly Gly Pro Ser Ile Gln Asp Ile Pro Tyr Arg Asp Leu Ser
545                 550                 555                 560

Asp Gln Val Leu Phe Leu Ser Ser Leu Phe Arg Gly Glu Phe Ile Tyr
                565                 570                 575

Ser Gly Glu Gly Leu Ala Thr Asn Leu Glu Arg Thr Leu Leu Gly Leu
            580                 585                 590

Glu Ala Asp Asn Val Ile Leu Leu Glu Arg Asp Glu Glu Gly Asn Ile
        595                 600                 605

Thr Lys Val Gly Leu Ser Gly Ala Glu Arg Ala Gly Arg Glu Asn
610                 615                 620

Phe Asp Phe Tyr Cys Phe Leu Ile Trp Pro Phe Ile Glu Ala Ser Trp
625                 630                 635                 640

Leu Ala Ala Val Ser Leu Met Gly Leu Val Pro Pro Ala Gly Gln Lys
```

```
                       645                 650                 655
Asp Asp Ile Trp Val Gln Val Ser Lys Ala Gln Asp Ser Ala Gln Leu
            660                 665                 670

Leu Gly Lys Thr Leu Tyr His Gln Gly Asp Leu Ser Tyr Phe Glu Ala
            675                 680                 685

Val Asn Lys Glu Thr Leu Lys Asn Ser Tyr Gln Arg Phe Ala Glu Glu
            690                 695                 700

Gly Ile Ile Gln Val Val Lys Ser Lys Asp Thr Arg Ile Pro Pro Arg
705                 710                 715                 720

Leu Arg Ile Ala Pro Glu Trp Arg Pro Gly Arg Asp Lys Glu Thr Gly
            725                 730                 735

Glu Leu Leu Pro Ala Gly Arg Leu Trp Asp Phe Thr Glu Lys Ile Ala
            740                 745                 750

Ser Ser Arg Arg Glu Gly Lys Asn Arg Arg Asp Gly Ala Thr Val Ser
            755                 760                 765

Ser Arg Val Leu Arg Leu Thr Asn Glu Leu Gly Arg Lys Leu Phe Glu
            770                 775                 780

Glu Ala Val Glu Gly Thr Gly Lys Gly Lys Gly Lys Gly Lys Gly Lys Gly
785                 790                 795                 800

Lys Ala Ala Val Pro Ala Arg Leu Ser Ser Glu Asp Glu Arg Ser Leu
            805                 810                 815

Ser Arg Thr Val Arg Glu Gln Glu Arg Lys Arg Lys Leu Glu Arg Arg
            820                 825                 830

Ala His Leu
        835

<210> SEQ ID NO 22
<211> LENGTH: 807
<212> TYPE: PRT
<213> ORGANISM: Escherichia coli

<400> SEQUENCE: 22

Met Ser Gly Trp Pro Arg Ile Tyr Tyr Lys Leu Leu Asn Leu Pro Leu
1               5                   10                  15

Ser Ile Leu Val Lys Ser Lys Ser Ile Pro Ala Asp Pro Ala Pro Glu
            20                  25                  30

Leu Gly Leu Asp Thr Ser Arg Pro Ile Met Tyr Val Leu Pro Tyr Asn
        35                  40                  45

Ser Lys Ala Asp Leu Leu Thr Leu Arg Ala Gln Cys Leu Ala His Asp
    50                  55                  60

Leu Pro Asp Pro Leu Glu Pro Leu Glu Ile Asp Gly Thr Leu Leu Pro
65                  70                  75                  80

Arg Tyr Val Phe Ile His Gly Gly Pro Arg Val Phe Thr Tyr Tyr Thr
                85                  90                  95

Pro Lys Glu Glu Ser Ile Lys Leu Phe His Asp Tyr Leu Asp Leu His
            100                 105                 110

Arg Ser Asn Pro Asn Leu Asp Val Gln Met Val Pro Val Ser Val Met
            115                 120                 125

Phe Gly Arg Ala Pro Gly Arg Glu Lys Gly Glu Val Asn Pro Pro Leu
        130                 135                 140

Arg Met Leu Asn Gly Val Gln Lys Phe Phe Ala Val Leu Trp Leu Gly
145                 150                 155                 160

Arg Asp Ser Phe Val Arg Phe Ser Pro Val Ser Leu Arg Arg Met
                165                 170                 175
```

```
Ala Asp Glu His Gly Thr Asp Lys Thr Ile Ala Gln Lys Leu Ala Arg
            180                 185                 190

Val Ala Arg Met His Phe Ala Arg Gln Arg Leu Ala Ala Val Gly Pro
        195                 200                 205

Arg Leu Pro Ala Arg Gln Asp Leu Phe Asn Lys Leu Leu Ala Ser Arg
    210                 215                 220

Ala Ile Ala Lys Ala Val Glu Asp Glu Ala Arg Ser Lys Lys Ile Ser
225                 230                 235                 240

His Glu Lys Ala Gln Gln Asn Ala Ile Ala Leu Met Glu Glu Ile Ala
                245                 250                 255

Ala Asn Phe Ser Tyr Glu Met Ile Arg Leu Thr Asp Arg Ile Leu Gly
            260                 265                 270

Phe Thr Trp Asn Arg Leu Tyr Gln Gly Ile Asn Val His Asn Ala Glu
        275                 280                 285

Arg Val Arg Gln Leu Ala His Asp Gly His Glu Leu Tyr Val Pro
    290                 295                 300

Cys His Arg Ser His Met Asp Tyr Leu Leu Ser Tyr Val Leu Tyr
305                 310                 315                 320

His Gln Gly Leu Val Pro Pro His Ile Ala Ala Gly Ile Asn Leu Asn
                325                 330                 335

Phe Trp Pro Ala Gly Pro Ile Phe Arg Arg Leu Gly Ala Phe Phe Ile
            340                 345                 350

Arg Arg Thr Phe Lys Gly Asn Lys Leu Tyr Ser Thr Val Phe Arg Glu
        355                 360                 365

Tyr Leu Gly Glu Leu Phe Ser Arg Gly Tyr Ser Val Glu Tyr Phe Val
    370                 375                 380

Glu Gly Gly Arg Ser Arg Thr Gly Arg Leu Leu Asp Pro Lys Thr Gly
385                 390                 395                 400

Thr Leu Ser Met Thr Ile Gln Ala Met Leu Arg Gly Gly Thr Arg Pro
                405                 410                 415

Ile Thr Leu Ile Pro Ile Tyr Ile Gly Tyr Glu His Val Met Glu Val
            420                 425                 430

Gly Thr Tyr Ala Lys Glu Leu Arg Gly Ala Thr Lys Glu Lys Glu Ser
        435                 440                 445

Leu Pro Gln Met Leu Arg Gly Leu Ser Lys Leu Arg Asn Leu Gly Gln
    450                 455                 460

Gly Tyr Val Asn Phe Gly Glu Pro Met Pro Leu Met Thr Tyr Leu Asn
465                 470                 475                 480

Gln His Val Pro Asp Trp Arg Glu Ser Ile Asp Pro Ile Glu Ala Val
                485                 490                 495

Arg Pro Ala Trp Leu Thr Pro Thr Val Asn Asn Ile Ala Ala Asp Leu
            500                 505                 510

Met Val Arg Ile Asn Asn Ala Gly Ala Asn Ala Met Asn Leu Cys
        515                 520                 525

Cys Thr Ala Leu Leu Ala Ser Arg Gln Arg Ser Leu Thr Arg Glu Gln
    530                 535                 540

Leu Thr Glu Gln Leu Asn Cys Tyr Leu Asp Leu Met Arg Asn Val Pro
545                 550                 555                 560

Tyr Ser Thr Asp Ser Thr Val Pro Ser Ala Ser Ala Ser Glu Leu Ile
                565                 570                 575

Asp His Ala Leu Gln Met Asn Lys Phe Glu Val Glu Lys Asp Thr Ile
            580                 585                 590

Gly Asp Ile Ile Ile Leu Pro Arg Glu Gln Ala Val Leu Met Thr Tyr
```

```
            595                 600                 605
Tyr Arg Asn Ile Ala His Met Leu Val Leu Pro Ser Leu Met Ala
        610                 615                 620

Ala Ile Val Thr Gln His Arg His Ile Ser Arg Asp Val Leu Met Glu
625                 630                 635                 640

His Val Asn Val Leu Tyr Pro Met Leu Lys Ala Glu Leu Phe Leu Arg
                645                 650                 655

Trp Asp Arg Asp Glu Leu Pro Asp Val Ile Asp Ala Leu Ala Asn Glu
                660                 665                 670

Met Gln Arg Gln Gly Leu Ile Thr Leu Gln Asp Asp Glu Leu His Ile
                675                 680                 685

Asn Pro Ala His Ser Arg Thr Leu Gln Leu Leu Ala Ala Gly Ala Arg
690                 695                 700

Glu Thr Leu Gln Arg Tyr Ala Ile Thr Phe Trp Leu Leu Ser Ala Asn
705                 710                 715                 720

Pro Ser Ile Asn Arg Gly Thr Leu Glu Lys Glu Ser Arg Thr Val Ala
                725                 730                 735

Gln Arg Leu Ser Val Leu His Gly Ile Asn Ala Pro Glu Phe Phe Asp
                740                 745                 750

Lys Ala Val Phe Ser Ser Leu Val Leu Thr Leu Arg Asp Glu Gly Tyr
                755                 760                 765

Ile Ser Asp Ser Gly Asp Ala Glu Pro Ala Glu Thr Met Lys Val Tyr
770                 775                 780

Gln Leu Leu Ala Glu Leu Ile Thr Ser Asp Val Arg Leu Thr Ile Glu
785                 790                 795                 800

Ser Ala Thr Gln Gly Glu Gly
                805

<210> SEQ ID NO 23
<211> LENGTH: 1092
<212> TYPE: PRT
<213> ORGANISM: Ustilago maydis

<400> SEQUENCE: 23

Met Thr Gly Thr Ser Asn Leu Pro Ala Ala Ser Ser Gln Asp Ser Ala
1               5                   10                  15

Val Ile Thr Thr Leu Ser Ser Pro Ser Glu Ala His Leu Ser Thr Ala
                20                  25                  30

Ser His Pro Ser Ala Ala Ala Ser Ser Thr Ala Ser Ala Gln His Pro
            35                  40                  45

Pro Thr Ile Asp Thr His Pro Thr Arg Leu Ser Ser Asn Asp Pro Leu
        50                  55                  60

Lys Lys His Pro Asn Thr Ala Ile Ala Lys Gly Thr Ala Ala Glu Val
65                  70                  75                  80

Gly Ser Lys Gln Lys Glu Phe Gln Arg Ala Gln His Leu Ser Leu
                85                  90                  95

Thr Ser Lys Pro Ile Pro Tyr Ala Arg Gln Gly Asp Ser Pro Arg Leu
                100                 105                 110

Leu Val Val Leu Lys Asp Phe Asp Arg Leu Leu Arg Ser Leu Pro Ile
            115                 120                 125

Pro Leu His His Ile Val Pro Thr Ile Val Ala Arg Phe Ile Cys Arg
        130                 135                 140

Val Phe Arg Ser Gln Asn Ile Met Ala Ser Asn Ile Ala Phe Asp Ile
145                 150                 155                 160
```

```
Ala Leu Phe Phe Trp Arg Ile Ile Ile Asn Leu Phe Phe Arg Glu Ile
                165                 170                 175

Arg Pro Arg Ser Ser Trp Arg Ile Pro Arg Glu Gly Pro Val Ile Phe
            180                 185                 190

Val Ala Ala Pro His His Asn Gln Phe Leu Asp Pro Leu Leu Leu Ala
        195                 200                 205

Ser Glu Val Arg Arg Ala Ser Gly Arg Arg Val Ala Phe Leu Ile Ala
    210                 215                 220

Glu Lys Ser Ile Lys Arg Arg Phe Val Gly Ala Ala Arg Ile Met
225                 230                 235                 240

Gln Ser Ile Pro Val Ala Arg Ala Ala Asp Ser Ala Lys Ala Gly Lys
                245                 250                 255

Gly Tyr Ile Ser Leu His Pro Ser Gly Asp Pro Leu Leu Ile Gln Gly
            260                 265                 270

His Gly Thr Ala Phe Lys Ser Gln Leu Gln Leu Lys Gly Gln Ile Met
        275                 280                 285

Leu Pro Lys Ala Cys Gly His Ala Thr Val Glu Val Val Glu Val Ile
    290                 295                 300

Ser Asp Thr Glu Leu Lys Ile Lys Lys Glu Phe Lys Asp Pro Arg Ala
305                 310                 315                 320

Leu Asp Met Leu Arg Gly Lys Val Pro Gln Pro Glu Pro Thr Lys Ser
                325                 330                 335

Asp Lys Lys Pro Ser Lys Ser Ser Ser Lys Ala Leu Glu Lys Val
            340                 345                 350

Ala Ala Asp Leu Phe Glu Asn Gln Gly Cys Arg Tyr Ser Cys Leu Pro
        355                 360                 365

Phe Val Asp Gln Thr Gln Met Tyr Ala Lys Val Tyr Asp Lys Leu Ala
    370                 375                 380

Glu Gly Gly Cys Leu Gly Ile Phe Pro Glu Gly Gly Ser His Asp Arg
385                 390                 395                 400

Thr Asp Leu Leu Pro Leu Lys Ala Gly Val Val Ile Met Ala Leu Gly
                405                 410                 415

Ala Met Ser Ala Asn Arg Asp Leu Asn Val Arg Ile Val Pro Val Gly
            420                 425                 430

Leu Ser Tyr Phe His Pro His Lys Phe Arg Ser Arg Ala Val Val Glu
        435                 440                 445

Phe Gly Ala Pro Ile Asp Val Pro Arg Gln Leu Val Gly Gln Phe Asp
    450                 455                 460

Glu Gly Gly Glu Gly Lys Arg Lys Ala Val Gly Gln Met Met Asp Ile
465                 470                 475                 480

Val Tyr Asp Gly Leu Lys Gly Val Thr Leu Arg Ala Pro Asp Tyr Glu
                485                 490                 495

Thr Leu Met Val Val Gln Ala Gly Arg Arg Leu Tyr Arg Ala Pro Gly
            500                 505                 510

Gln Ser Leu Ser Leu Gly Gln Thr Val Ala Leu Asn Arg Lys Phe Ile
        515                 520                 525

Met Gly Tyr Leu Gln Phe Lys Asp Glu Pro Arg Val Val Lys Leu Arg
    530                 535                 540

Asp Glu Val Leu Arg Tyr Asn Lys Lys Leu Tyr Ala Gly Leu Arg
545                 550                 555                 560

Asp His Gln Val Glu Arg Ala Thr Arg Ala Gly Trp Arg Ser Leu Gly
                565                 570                 575

Leu Leu Ala Tyr Arg Leu Gly Leu Leu Gly Leu Trp Gly Gly Leu Ala
```

-continued

```
                580                 585                 590
Leu Pro Gly Ala Val Leu Asn Ser Pro Ile Ile Leu Ala Lys Ile
            595                 600                 605
Ile Ser His Lys Lys Ala Lys Glu Ala Leu Ala Ser Gln Val Lys
            610                 615                 620
Val Ala Gly Arg Asp Val Leu Ala Thr Trp Lys Val Leu Val Ser Leu
625                         630                 635                 640
Gly Val Ala Pro Ile Leu Tyr Ser Phe Tyr Ala Ala Leu Ala Thr Tyr
                        645                 650                 655
Leu Ala His Arg Leu Glu Leu Ser Pro Arg Thr Arg Ala Leu Met Pro
                660                 665                 670
Leu Tyr Thr Leu Ile Val Leu Pro Thr Met Ser Tyr Ser Ala Leu Lys
                675                 680                 685
Phe Ala Glu Val Gly Ile Asp Ile Tyr Lys Ser Leu Pro Pro Leu Phe
                690                 695                 700
Ile Ser Leu Ile Pro Gly Asn His Lys Val Ile Leu Asp Leu Gln Gln
705                         710                 715                 720
Thr Arg Thr Lys Ile Ser Ala Asp Met His Ala Leu Ile Asp Glu Leu
                        725                 730                 735
Ala Pro Gln Val Trp Glu Asp Phe Ala Glu Asn Arg Met Leu Pro Ser
                        740                 745                 750
Ala Ser Ala Pro Pro Thr Pro Ser Arg Glu Ala Leu Val Trp Lys Asp
                755                 760                 765
Lys Lys Gln Ser Ser Ser Ala Ala Ser Asp Ala Leu Ser His Pro Leu
            770                 775                 780
Gln Trp Met Asp Glu Arg Leu Phe Gly Trp Gly Arg Arg His Ser
785                         790                 795                 800
Ser Thr Arg Arg Ser Leu Thr Ala Glu Glu Ile Lys His Leu Arg Ser
                        805                 810                 815
Pro Ser Leu Thr Arg Gly Ser Ala Lys Asp Glu Asn Ser Val Leu Asp
                        820                 825                 830
Asp Glu Asp Gly Ala Arg Phe Glu Gly Glu Gly Asp Gly Ser Leu Asp
                835                 840                 845
Asp Val Ser Glu Gly Ser Ser Ser Phe Ile Glu Ser Gly Glu Glu Asp
            850                 855                 860
Glu Gly Asp Tyr Glu Ala Val Phe Ser Met Leu Asn Pro Gln Asn Leu
865                         870                 875                 880
Leu Asn Gly Leu Arg Asn Gly Gly Leu Ser Pro Gly Thr Pro Gly Ser
                        885                 890                 895
Gly Gly Arg Arg Ser Arg Thr His Ser Arg Ser Arg Ser Gly Ser Arg
                        900                 905                 910
Gly Ser Ile Gly Gly Val Ala Ser Gly Glu Thr Phe Ala Glu Lys Arg
            915                 920                 925
Asn Arg Ser Ser Gln Asp Leu Arg Ala Leu Met Arg Glu Gly Gly Ala
            930                 935                 940
Met Ser Pro Thr Thr Thr Arg Ser Ser Gly Ile Leu Glu Gly Ala Gly
945                         950                 955                 960
Ser Lys Gln Ser Ser Arg Thr Ser Ala Leu Pro Ala Ser Leu Ile Thr
                        965                 970                 975
Thr Asn Ile Ser Gly Asn Asp Gly Glu Asn Gly Ala Ser Lys Ala Ser
                        980                 985                 990
Asn Thr Ser Arg Arg Asn Arg Thr His Ser Leu Ser Glu Asp Val His
                995                 1000                1005
```

```
Val Ser Glu Leu Lys Asn Ala Gly Pro Ala Ala Lys Lys Leu Pro
    1010            1015                1020

Phe Ser Ala Ala Ser Gln Ala Phe Glu Met Gln His Glu Ala Ser
    1025            1030                1035

Gly Gly Gln Ala Gly Tyr Arg Pro Lys Leu Glu Asn Met Gln Ser
    1040            1045                1050

Ala Glu Asn Thr Pro Pro Ala Thr Pro Lys His Glu Asp Lys Lys
    1055            1060                1065

Val Leu Thr Ser Ala Ser Ser Val Pro Thr Asp Ser Asn Asp Leu
    1070            1075                1080

Asp Gly Lys Asp Asp Gly Lys Ala Gln
    1085            1090

<210> SEQ ID NO 24
<211> LENGTH: 759
<212> TYPE: PRT
<213> ORGANISM: Saccharomyces cerevisiae

<400> SEQUENCE: 24

Met Pro Ala Pro Lys Leu Thr Glu Lys Phe Ala Ser Ser Lys Ser Thr
1               5                   10                  15

Gln Lys Thr Thr Asn Tyr Ser Ser Ile Glu Ala Lys Ser Val Lys Thr
            20                  25                  30

Ser Ala Asp Gln Ala Tyr Ile Tyr Gln Glu Pro Ser Ala Thr Lys Lys
        35                  40                  45

Ile Leu Tyr Ser Ile Ala Thr Trp Leu Leu Tyr Asn Ile Phe His Cys
    50                  55                  60

Phe Phe Arg Glu Ile Arg Gly Arg Gly Ser Phe Lys Val Pro Gln Gln
65              70                  75                      80

Gly Pro Val Ile Phe Ala Ala Pro His Ala Asn Gln Phe Val Asp
                85                  90                  95

Pro Val Ile Leu Met Gly Glu Val Lys Lys Ser Val Asn Arg Arg Val
                100                 105                 110

Ser Phe Leu Ile Ala Glu Ser Ser Leu Lys Gln Pro Pro Ile Gly Phe
            115                 120                 125

Leu Ala Ser Phe Phe Met Ala Ile Gly Val Val Arg Pro Gln Asp Asn
        130                 135                 140

Leu Lys Pro Ala Glu Gly Thr Ile Arg Val Asp Pro Thr Asp Tyr Lys
145                 150                 155                 160

Arg Val Ile Gly His Asp Thr Phe Leu Thr Asp Cys Met Pro Lys
                165                 170                 175

Gly Leu Ile Gly Leu Pro Lys Ser Met Gly Phe Gly Glu Ile Gln Ser
            180                 185                 190

Ile Glu Ser Asp Thr Ser Leu Thr Leu Arg Lys Glu Phe Lys Met Ala
        195                 200                 205

Lys Pro Glu Ile Lys Thr Ala Leu Leu Thr Gly Thr Thr Tyr Lys Tyr
    210                 215                 220

Ala Ala Lys Val Asp Gln Ser Cys Val Tyr His Arg Val Phe Glu His
225                 230                 235                 240

Leu Ala His Asn Asn Cys Ile Gly Ile Phe Pro Glu Gly Gly Ser His
                245                 250                 255

Asp Arg Thr Asn Leu Leu Pro Leu Lys Ala Gly Val Ala Ile Met Ala
            260                 265                 270

Leu Gly Cys Met Asp Lys His Pro Asp Val Asn Val Lys Ile Val Pro
```

```
            275                 280                 285
Cys Gly Met Asn Tyr Phe His Pro His Lys Phe Arg Ser Arg Ala Val
290                 295                 300
Val Glu Phe Gly Asp Pro Ile Glu Ile Pro Lys Glu Leu Val Ala Lys
305                 310                 315                 320
Tyr His Asn Pro Glu Thr Asn Arg Asp Ala Val Lys Glu Leu Leu Asp
                    325                 330                 335
Thr Ile Ser Lys Gly Leu Gln Ser Val Thr Val Thr Cys Ser Asp Tyr
                340                 345                 350
Glu Thr Leu Met Val Val Gln Thr Ile Arg Arg Leu Tyr Met Thr Gln
                    355                 360                 365
Phe Ser Thr Lys Leu Pro Leu Pro Leu Ile Val Glu Met Asn Arg Arg
                370                 375                 380
Met Val Lys Gly Tyr Glu Phe Tyr Arg Asn Asp Pro Lys Ile Ala Asp
385                 390                 395                 400
Leu Thr Lys Asp Ile Met Ala Tyr Asn Ala Ala Leu Arg His Tyr Asn
                    405                 410                 415
Leu Pro Asp His Leu Val Glu Glu Ala Lys Val Asn Phe Ala Lys Asn
                    420                 425                 430
Leu Gly Leu Val Phe Phe Arg Ser Ile Gly Leu Cys Ile Leu Phe Ser
                435                 440                 445
Leu Ala Met Pro Gly Ile Ile Met Phe Ser Pro Val Phe Ile Leu Ala
                450                 455                 460
Lys Arg Ile Ser Gln Glu Lys Ala Arg Thr Ala Leu Ser Lys Ser Thr
465                 470                 475                 480
Val Lys Ile Lys Ala Asn Asp Val Ile Ala Thr Trp Lys Ile Leu Ile
                    485                 490                 495
Gly Met Gly Phe Ala Pro Leu Leu Tyr Ile Phe Trp Ser Val Leu Ile
                    500                 505                 510
Thr Tyr Tyr Leu Arg His Lys Pro Trp Asn Lys Ile Tyr Val Phe Ser
                515                 520                 525
Gly Ser Tyr Ile Ser Cys Val Ile Val Thr Tyr Ser Ala Leu Ile Val
                530                 535                 540
Gly Asp Ile Gly Met Asp Gly Phe Lys Ser Leu Arg Pro Leu Val Leu
545                 550                 555                 560
Ser Leu Thr Ser Pro Lys Gly Leu Gln Lys Leu Gln Lys Asp Arg Arg
                    565                 570                 575
Asn Leu Ala Glu Arg Ile Ile Glu Val Val Asn Asn Phe Gly Ser Glu
                    580                 585                 590
Leu Phe Pro Asp Phe Asp Ser Ala Ala Leu Arg Glu Glu Phe Asp Val
                    595                 600                 605
Ile Asp Glu Glu Glu Asp Arg Lys Thr Ser Glu Leu Asn Arg Arg
                610                 615                 620
Lys Met Leu Arg Lys Gln Lys Ile Lys Arg Gln Glu Lys Asp Ser Ser
625                 630                 635                 640
Ser Pro Ile Ile Ser Gln Arg Asp Asn His Asp Ala Tyr Glu His His
                    645                 650                 655
Asn Gln Asp Ser Asp Gly Val Ser Leu Val Asn Ser Asn Ser Leu
                    660                 665                 670
Ser Asn Ile Pro Leu Phe Ser Ser Thr Phe His Arg Lys Ser Glu Ser
                675                 680                 685
Ser Leu Ala Ser Thr Ser Val Ala Pro Ser Ser Ser Glu Phe Glu
                690                 695                 700
```

```
Val Glu Asn Glu Ile Leu Glu Glu Lys Asn Gly Leu Ala Ser Lys Ile
705                 710                 715                 720

Ala Gln Ala Val Leu Asn Lys Arg Ile Gly Glu Asn Thr Ala Arg Glu
                725                 730                 735

Glu Glu Glu Glu Glu Glu Glu Glu Glu Glu Glu Glu Glu Glu Glu Glu
                740                 745                 750

Glu Gly Lys Glu Gly Asp Ala
        755
```

<210> SEQ ID NO 25
<211> LENGTH: 743
<212> TYPE: PRT
<213> ORGANISM: Saccharomyces cerevisiae

<400> SEQUENCE: 25

```
Met Ser Ala Pro Ala Ala Asp His Asn Ala Ala Lys Pro Ile Pro His
1               5                   10                  15

Val Pro Gln Ala Ser Arg Arg Tyr Lys Asn Ser Tyr Asn Gly Phe Val
                20                  25                  30

Tyr Asn Ile His Thr Trp Leu Tyr Asp Val Ser Val Phe Leu Phe Asn
                35                  40                  45

Ile Leu Phe Thr Ile Phe Phe Arg Glu Ile Lys Val Arg Gly Ala Tyr
50                  55                  60

Asn Val Pro Glu Val Gly Val Pro Thr Ile Leu Val Cys Ala Pro His
65                  70                  75                  80

Ala Asn Gln Phe Ile Asp Pro Ala Leu Val Met Ser Gln Thr Arg Leu
                85                  90                  95

Leu Lys Thr Ser Ala Gly Lys Ser Arg Ser Arg Met Pro Cys Phe Val
                100                 105                 110

Thr Ala Glu Ser Ser Phe Lys Lys Arg Phe Ile Ser Phe Gly His
                115                 120                 125

Ala Met Gly Gly Ile Pro Val Pro Arg Ile Gln Asp Asn Leu Lys Pro
                130                 135                 140

Val Asp Glu Asn Leu Glu Ile Tyr Ala Pro Asp Leu Lys Asn His Pro
145                 150                 155                 160

Glu Ile Ile Lys Gly Arg Ser Lys Asn Pro Gln Thr Thr Pro Val Asn
                165                 170                 175

Phe Thr Lys Arg Phe Ser Ala Lys Ser Leu Leu Gly Leu Pro Asp Tyr
                180                 185                 190

Leu Ser Asn Ala Gln Ile Lys Glu Ile Pro Asp Glu Thr Ile Ile
                195                 200                 205

Leu Ser Ser Pro Phe Arg Thr Ser Lys Ser Lys Val Val Glu Leu Leu
                210                 215                 220

Thr Asn Gly Thr Asn Phe Lys Tyr Ala Glu Lys Ile Asp Asn Thr Glu
225                 230                 235                 240

Thr Phe Gln Ser Val Phe Asp His Leu His Thr Lys Gly Cys Val Gly
                245                 250                 255

Ile Phe Pro Glu Gly Gly Ser His Asp Arg Pro Ser Leu Leu Pro Ile
                260                 265                 270

Lys Ala Gly Val Ala Ile Met Ala Leu Gly Ala Val Ala Ala Asp Pro
                275                 280                 285

Thr Met Lys Val Ala Val Val Pro Cys Gly Leu His Tyr Phe His Arg
                290                 295                 300

Asn Lys Phe Arg Ser Arg Ala Val Leu Glu Tyr Gly Glu Pro Ile Val
```

-continued

```
            305                 310                 315                 320
Val Asp Gly Lys Tyr Gly Glu Met Tyr Lys Asp Ser Pro Arg Glu Thr
                    325                 330                 335
Val Ser Lys Leu Leu Lys Lys Ile Thr Asn Ser Leu Phe Ser Val Thr
                    340                 345                 350
Glu Asn Ala Pro Asp Tyr Asp Thr Leu Met Val Ile Gln Ala Ala Arg
            355                 360                 365
Arg Leu Tyr Gln Pro Val Lys Val Arg Leu Pro Leu Pro Ala Ile Val
        370                 375                 380
Glu Ile Asn Arg Arg Leu Leu Phe Gly Tyr Ser Lys Phe Lys Asp Asp
385                 390                 395                 400
Pro Arg Ile Ile His Leu Lys Lys Leu Val Tyr Asp Tyr Asn Arg Lys
                405                 410                 415
Leu Asp Ser Val Gly Leu Lys Asp His Gln Val Met Gln Leu Lys Thr
                420                 425                 430
Thr Lys Leu Glu Ala Leu Arg Cys Phe Val Thr Leu Ile Val Arg Leu
        435                 440                 445
Ile Lys Phe Ser Val Phe Ala Ile Leu Ser Leu Pro Gly Ser Ile Leu
    450                 455                 460
Phe Thr Pro Ile Phe Ile Cys Arg Val Tyr Ser Glu Lys Lys Ala
465                 470                 475                 480
Lys Glu Gly Leu Lys Lys Ser Leu Val Lys Ile Lys Gly Thr Asp Leu
                485                 490                 495
Leu Ala Thr Trp Lys Leu Ile Val Ala Leu Ile Leu Ala Pro Ile Leu
                500                 505                 510
Tyr Val Thr Tyr Ser Ile Leu Leu Ile Ile Leu Ala Arg Lys Gln His
            515                 520                 525
Tyr Cys Arg Ile Trp Val Pro Ser Asn Asn Ala Phe Ile Gln Phe Val
        530                 535                 540
Tyr Phe Tyr Ala Leu Leu Val Phe Thr Thr Tyr Ser Ser Leu Lys Thr
545                 550                 555                 560
Gly Glu Ile Gly Val Asp Leu Phe Lys Ser Leu Arg Pro Leu Phe Val
                565                 570                 575
Ser Ile Val Tyr Pro Gly Lys Lys Ile Glu Ile Gln Thr Thr Arg
            580                 585                 590
Lys Asn Leu Ser Leu Glu Leu Thr Ala Val Cys Asn Asp Leu Gly Pro
        595                 600                 605
Leu Val Phe Pro Asp Tyr Asp Lys Leu Ala Thr Glu Ile Phe Ser Lys
    610                 615                 620
Arg Asp Gly Tyr Asp Val Ser Ser Asp Ala Glu Ser Ser Ile Ser Arg
625                 630                 635                 640
Met Ser Val Gln Ser Arg Ser Arg Ser Ser Ile His Ser Ile Gly
                645                 650                 655
Ser Leu Ala Ser Asn Ala Leu Ser Arg Val Asn Ser Arg Gly Ser Leu
                660                 665                 670
Thr Asp Ile Pro Ile Phe Ser Asp Ala Lys Gln Gly Gln Trp Lys Ser
            675                 680                 685
Glu Gly Glu Thr Ser Glu Asp Glu Asp Glu Phe Asp Glu Lys Asn Pro
        690                 695                 700
Ala Ile Val Gln Thr Ala Arg Ser Ser Asp Leu Asn Lys Glu Asn Ser
705                 710                 715                 720
Arg Asn Thr Asn Ile Ser Ser Lys Ile Ala Ser Leu Val Arg Gln Lys
                725                 730                 735
```

-continued

Arg Glu His Glu Lys Lys Glu
                740

<210> SEQ ID NO 26
<211> LENGTH: 35
<212> TYPE: DNA
<213> ORGANISM: Artificial sequence
<220> FEATURE:
<223> OTHER INFORMATION: primer Eco-MaGPAT3-F

<400> SEQUENCE: 26
gaattcatgg gtctccagat ctatgacttc gtctc                              35

<210> SEQ ID NO 27
<211> LENGTH: 34
<212> TYPE: DNA
<213> ORGANISM: Artificial sequence
<220> FEATURE:
<223> OTHER INFORMATION: primer Sal-MaGPAT3-R

<400> SEQUENCE: 27
gtcgacttat gcctccttag acttgactgc atcc                               34

<210> SEQ ID NO 28
<211> LENGTH: 30
<212> TYPE: DNA
<213> ORGANISM: Artificial sequence
<220> FEATURE:
<223> OTHER INFORMATION: primer Not-MaGPAT4-F1

<400> SEQUENCE: 28
gcggccgcat gacaaccggc gacagtaccg                                    30

<210> SEQ ID NO 29
<211> LENGTH: 29
<212> TYPE: DNA
<213> ORGANISM: Artificial sequence
<220> FEATURE:
<223> OTHER INFORMATION: primer Not-MaGPAT4-F2

<400> SEQUENCE: 29
gcggccgcat gcccatcgtt ccagctcag                                     29

<210> SEQ ID NO 30
<211> LENGTH: 28
<212> TYPE: DNA
<213> ORGANISM: Artificial sequence
<220> FEATURE:
<223> OTHER INFORMATION: primer Bam-MaGPAT4-R

<400> SEQUENCE: 30
ggatccttat aatttcgggg cgccatcg                                      28

<210> SEQ ID NO 31
<211> LENGTH: 26
<212> TYPE: DNA
<213> ORGANISM: Artificial sequence
<220> FEATURE:
<223> OTHER INFORMATION: primer Xba1-Des-SCT1-F

<400> SEQUENCE: 31
tctagaatgc ctgcaccaaa actcac                                        26

<210> SEQ ID NO 32
<211> LENGTH: 26

```
<212> TYPE: DNA
<213> ORGANISM: Artificial sequence
<220> FEATURE:
<223> OTHER INFORMATION: primer Xba1-Des-SCT1-R

<400> SEQUENCE: 32
tctagaccac aaggtgatca ggaaga                                          26

<210> SEQ ID NO 33
<211> LENGTH: 20
<212> TYPE: DNA
<213> ORGANISM: Artificial sequence
<220> FEATURE:
<223> OTHER INFORMATION: primer SCT1outORF-F

<400> SEQUENCE: 33
agtgtaggaa gcccggaatt                                                20

<210> SEQ ID NO 34
<211> LENGTH: 20
<212> TYPE: DNA
<213> ORGANISM: Artificial sequence
<220> FEATURE:
<223> OTHER INFORMATION: primer SCT1inORF-R

<400> SEQUENCE: 34
gcgtagatcc aacagactac                                                20

<210> SEQ ID NO 35
<211> LENGTH: 20
<212> TYPE: DNA
<213> ORGANISM: Artificial sequence
<220> FEATURE:
<223> OTHER INFORMATION: primer LEU2inORF-F

<400> SEQUENCE: 35
ttgcctcttc caagagcaca                                                20

<210> SEQ ID NO 36
<211> LENGTH: 54
<212> TYPE: DNA
<213> ORGANISM: Artificial sequence
<220> FEATURE:
<223> OTHER INFORMATION: oligo DNA MCS-for-pUC18-F2

<400> SEQUENCE: 36
aattcataag aatgcggccg ctaaactatt ctagactagg tcgacggcgc gcca          54

<210> SEQ ID NO 37
<211> LENGTH: 54
<212> TYPE: DNA
<213> ORGANISM: Artificial sequence
<220> FEATURE:
<223> OTHER INFORMATION: oligo DNA MCS-for-pUC18-R2

<400> SEQUENCE: 37
agcttggcgc gccgtcgacc tagtctagaa tagtttagcg gccgcattct tatg          54

<210> SEQ ID NO 38
<211> LENGTH: 26
<212> TYPE: DNA
<213> ORGANISM: Artificial sequence
<220> FEATURE:
<223> OTHER INFORMATION: primer Not1-GAPDHt-F

<400> SEQUENCE: 38
```

```
agcggccgca tagggagat cgaacc                                          26
```

<210> SEQ ID NO 39
<211> LENGTH: 33
<212> TYPE: DNA
<213> ORGANISM: Artificial sequence
<220> FEATURE:
<223> OTHER INFORMATION: primer EcoR1-Asc1-GAPDHt-R

<400> SEQUENCE: 39

```
agaattcggc gcgccatgca cgggtccttc tca                                 33
```

<210> SEQ ID NO 40
<211> LENGTH: 20
<212> TYPE: DNA
<213> ORGANISM: Artificial sequence
<220> FEATURE:
<223> OTHER INFORMATION: primer URA5g-F1

<400> SEQUENCE: 40

```
gtcgaccatg acaagtttgc                                                20
```

<210> SEQ ID NO 41
<211> LENGTH: 21
<212> TYPE: DNA
<213> ORGANISM: Artificial sequence
<220> FEATURE:
<223> OTHER INFORMATION: primer URA5g-R1

<400> SEQUENCE: 41

```
gtcgactgga agacgagcac g                                              21
```

<210> SEQ ID NO 42
<211> LENGTH: 43
<212> TYPE: DNA
<213> ORGANISM: Artificial sequence
<220> FEATURE:
<223> OTHER INFORMATION: primer hisHp+URA5-F

<400> SEQUENCE: 42

```
ggcaaacttg tcatgaagcg aaagagagat tatgaaaaca agc                      43
```

<210> SEQ ID NO 43
<211> LENGTH: 42
<212> TYPE: DNA
<213> ORGANISM: Artificial sequence
<220> FEATURE:
<223> OTHER INFORMATION: primer hisHp+MGt-F

<400> SEQUENCE: 43

```
cactcccttt tcttaattgt tgagagagtg ttgggtgaga gt                       42
```

<210> SEQ ID NO 44
<211> LENGTH: 27
<212> TYPE: DNA
<213> ORGANISM: Artificial sequence
<220> FEATURE:
<223> OTHER INFORMATION: primer pDuraSC-GAPt-F

<400> SEQUENCE: 44

```
taagaaaagg gagtgaatcg cataggg                                        27
```

<210> SEQ ID NO 45
<211> LENGTH: 23
<212> TYPE: DNA
<213> ORGANISM: Artificial sequence

```
<220> FEATURE:
<223> OTHER INFORMATION: primer URA5gDNA-F

<400> SEQUENCE: 45
catgacaagt tgccaagat gcg                                              23

<210> SEQ ID NO 46
<211> LENGTH: 28
<212> TYPE: DNA
<213> ORGANISM: Artificial sequence
<220> FEATURE:
<223> OTHER INFORMATION: primer pDurahG-hisp-R

<400> SEQUENCE: 46
attgttgaga gagtgttggg tgagagtg                                        28

<210> SEQ ID NO 47
<211> LENGTH: 38
<212> TYPE: DNA
<213> ORGANISM: Artificial sequence
<220> FEATURE:
<223> OTHER INFORMATION: primer MaGPAT4+hisp-F

<400> SEQUENCE: 47
cactctctca acaatatgac aaccggcgac agtaccgc                             38

<210> SEQ ID NO 48
<211> LENGTH: 38
<212> TYPE: DNA
<213> ORGANISM: Artificial sequence
<220> FEATURE:
<223> OTHER INFORMATION: primer MaGPAT4+MGt-R

<400> SEQUENCE: 48
cactcccttt tcttattata atttcggggc gccatcgc                             38

<210> SEQ ID NO 49
<211> LENGTH: 21
<212> TYPE: DNA
<213> ORGANISM: Artificial sequence
<220> FEATURE:
<223> OTHER INFORMATION: primer GPAT4-RT1

<400> SEQUENCE: 49
gagtgcttca tcgagggcac c                                               21

<210> SEQ ID NO 50
<211> LENGTH: 24
<212> TYPE: DNA
<213> ORGANISM: Artificial sequence
<220> FEATURE:
<223> OTHER INFORMATION: perimer GPAT4-RT2

<400> SEQUENCE: 50
tccttcactg tcaacctcga tcac                                            24
```